US007910100B2

(12) United States Patent
Stühmer et al.

(10) Patent No.: US 7,910,100 B2
(45) Date of Patent: Mar. 22, 2011

(54) ANTIBODIES DIRECTED TO THE MAMMALIAN EAG1 ION CHANNEL PROTEIN

(75) Inventors: Walter Stühmer, Göttingen (DE); Hendrik Knötgen, Penzberg (DE); David Gómez-Varela, Del Mar, CA (US); Luis A. Pardo, Göttingen (DE); Mike Rothe, Krailling (DE); Esther Zwick-Wallasch, Gauting (DE); Kerstin Dehne, München (DE)

(73) Assignee: Max-Planck-Gesellschaft zur Forderung der Wissen, Munich (DE)

( * ) Notice: Subject to any disclaimer, the term of this patent is extended or adjusted under 35 U.S.C. 154(b) by 247 days.

(21) Appl. No.: 11/664,345

(22) PCT Filed: Oct. 4, 2005

(86) PCT No.: PCT/EP2005/010671
§ 371 (c)(1),
(2), (4) Date: Jun. 2, 2008

(87) PCT Pub. No.: WO2006/037604
PCT Pub. Date: Apr. 13, 2006

(65) Prior Publication Data
US 2009/0028851 A1    Jan. 29, 2009

(30) Foreign Application Priority Data

Oct. 1, 2004 (EP) .................................... 04023489

(51) Int. Cl.
*A61K 39/395* (2006.01)
*G01N 33/574* (2006.01)
*G01N 33/53* (2006.01)
*C07K 16/18* (2006.01)

(52) U.S. Cl. ............... 424/133.1; 424/135.1; 424/136.1; 424/139.1; 424/156.1; 424/9.341; 435/7.1; 435/7.23; 530/387.9; 530/387.3; 530/388.15

(58) Field of Classification Search ........................ None
See application file for complete search history.

(56) References Cited

U.S. PATENT DOCUMENTS

| 5,741,957 A | 4/1998 | Deboer |
| 5,750,172 A | 5/1998 | Meade et al. |
| 5,756,687 A | 5/1998 | Denman et al. |
| 5,827,690 A | 10/1998 | Meade et al. |
| 5,877,293 A | 3/1999 | Adair et al. |
| 5,886,152 A | 3/1999 | Nakatani |
| 6,054,297 A | 4/2000 | Carter et al. |
| 2004/0254108 A1 * | 12/2004 | Ma et al. .................. 514/12 |

FOREIGN PATENT DOCUMENTS

| EP | 0239400 | 8/1994 |
| EP | 1073738 | 9/2004 |
| WO | WO 88/09344 | 12/1988 |
| WO | WO 90/07861 | 7/1990 |
| WO | WO 91/10741 | 7/1991 |
| WO | WO 94/02602 | 2/1994 |
| WO | WO 96/33735 | 10/1996 |
| WO | WO 96/34096 | 10/1996 |
| WO | WO 98/09622 | 3/1998 |
| WO | WO 00/09560 | 2/2000 |

OTHER PUBLICATIONS

Padlan EA et al. Structure of an antibody-antigen complex: Crystal structure of the HyHEL-10 Fab-lysozyme complex. Proc Natl Acad Sci USA, 1989; 86:5938-5942.*
Paul WE, Fundamental Immunology, Third Edition. Raven Press, New York, 1993, pp. 292-295.*
H. Ouadid et al., "Changes in the K+ Current-Density of MCF-7 Cells During Progression Through the Cell Cycle: Possible Involvement of a h-ether.a-gogo K+ Channel" *Receptors Channels.*, 7:345-56, (2001).
R. Meyer et al., "Identification of Ether a Go-Go and Calcium-Activated Potassium Channels in Human Melanoma Cells.", *J Membr Biol.*, 171:107-15, (1999).
L. Bianchi et al., "herg encodes a $K^+$ Current Highly Conserved in Tumors of Different Histogenesis: A Selective Advantage for Cancer Cells?[1]", *Cancer Res.* 58:815-22, (1998).
Davies et al., "Affinity improvement of single antibody VH domains: residues of all three hypervariable regions affect antigen binding," *Immunotechnology*, 2(3):169-179 (1996).
Holt et al., "Domain antibodies: proteins for therapy," *Trends in Biotechnology*, 21(11):484-490 (2003).
G. Kohler et al., "Continuous cultures of fused cells secreting antibody of predefined specificity.", *Nature.*, 256(5517):495-7, (1975).
R. Schier et al., "Efficient in vitro affinity maturation of phage antibodies using BIAcore guided selections." *Hum Antibodies Hybridomas*, 7(3):97-105, (1996).
A. Malmborg et al., "BIAcore as a tool in antibody engineering.", *J Immunol Methods*, 183:7-13, (1995).
H. Le Mouellic et al., "Targeted replacement of the homeobox gene Hox-3.1 by the *Escherichia coli lacZ* in mouse chimeric embryos.", *Proc Natl Acad Sci U S A.*, 87:4712-16, (1990).
R. Mandler et al., "Immunoconjugates of Geldanamycin and Anti-HER2 Monoclonal Antibodies: Antiproliferative Activity on Human Breast Carcinoma Cell Lines.", *J Natl Cancer Inst.*, 92(19):1573-81, (2000).
S. Doronina et al., "Development of potent monoclonal antibody auristatin conjugates for cancer therapy.", *Nat Biotechnol*, 21 (7):778-784, (2003).
C. Chothia et al. "Domain Association in Immunoglobulin Molecules The Packing of Variable Domains", *J. Mol, Biol.*, 186:651-63, (1985).

* cited by examiner

*Primary Examiner* — Elizabeth C. Kemmerer
*Assistant Examiner* — Kimberly A. Ballard
(74) *Attorney, Agent, or Firm* — DT Ward, PC

(57) ABSTRACT

The present invention relates to a particularly advantageous antibody, antibody fragment or derivative thereof, which specifically binds to/interacts with at least one epitope of the extracellular or intracellular domain or the mammalian EAG1 ion channel and to nucleic acid molecules encoding these anti-EAG1 antibodies, antibody fragments or derivatives and to vectors comprising such nucleic acid molecules. The invention additionally relates to methods for the preparation of such anti-EAG1 antibodies, antibody fragments or derivatives thereof, pharmaceutical compositions comprising these antibodies, antibody fragments or derivatives, and methods of using the antibodies, antibody fragments or derivatives or the compositions for a variety of purposes, such as diagnosing disease, treating disease, assessing for the presence of EAG1-expressing cells, or blocking EAG1 function in cells.

15 Claims, 33 Drawing Sheets

Fig. 1

Mouse ImAb4 light chain:
CDR1 – rssqslvhsngntylh (SEQ ID Nr. 172)
CDR2 – kvsnrfs (SEQ ID Nr. 173)
CDR3 – sqsthvppt (SEQ ID Nr. 174)

Mouse ImAb4 heavy chain:
CDR1 – gysitsdyawn (SEQ ID Nr. 175)
CDR2 – yisysgstiynpslks (SEQ ID Nr. 176)
CDR3 – fgnygntlny (SEQ ID Nr. 177)

Mouse ImAb3 light chain
CDR1 – kssqsllnsrtrknyla (SEQ ID Nr. 166)
CDR2 – wastres (SEQ ID Nr. 167)
CDR3 – kqsydlrt (SEQ ID Nr. 168)

Mouse ImAb3 heavy chain
CDR1 – gftftdyyms (SEQ ID Nr. 169)
CDR2 – firnkatgytteysasvkg (SEQ ID Nr. 170)
CDR3 – dfgsrwyfdv (SEQ ID Nr. 171)

Mouse ImAb1 light chain
CDR1 – KASQDIKSYLS (SEQ ID Nr. 160)
CDR2 – YATSLAD (SEQ ID Nr. 161)
CDR3 – LQHGESPYT (SEQ ID Nr. 162)

Mouse ImAb1 heavy chain
CDR1 – GFTFSNYAMS (SEQ ID Nr. 163)
CDR2 – SISSDGDTYFPDNVKG (SEQ ID Nr. 164)
CDR3 – GFMITF (SEQ ID Nr. 165)

Mouse ImAb5 light chain
CDR1 – KSSQSLLNSRTRKNYLA (SEQ ID Nr. 178)
CDR2 – WASTRES (SEQ ID Nr. 179)
CDR3 – KQSYDLRT (SEQ ID Nr. 180)

Mouse ImAb5 heavy chain
CDR1 – GFTFTDYYMS (SEQ ID Nr. 181)
CDR2 – FIRNKATGYTTEYSASVKG (SEQ ID Nr. 182)
CDR3 – DTAATWYFDV (SEQ ID Nr. 183)

Fig. 4
| Antibody | Epitope recognized | Bind to spots on the membrane | Net charge | Hydrophobic/-philic |
|---|---|---|---|---|
| ImAb4 | DYEIFDED | 3-8 | Minus 5 | Hydrophilic |
| ImAb3 | GSGKWEG | 21-24 | Zero | More hydrophobic |
| ImAb1 | YQFNGSGSGKWEG | 21-24 | Zero | More hydrophilic |
| ImAb5 | GSGKWEG | 21-24 | Zero | More hydrophobic |
| ImAb2 | NGSGSGKWEGG | 21-24 | Zero | More hydrophobic |
| Ifv001 | MGDYEIFDEDTKT | 3-8 | Minus 4 | More hydrophilic |
ImAb1 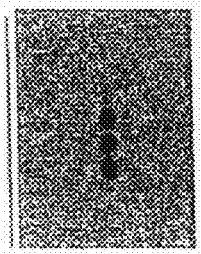
ImAb2 
ImAb4 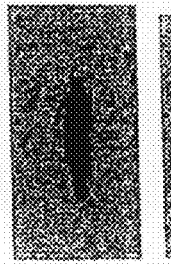
ImAb3 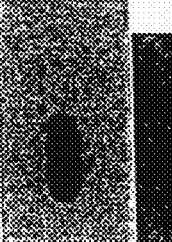
ImAb5 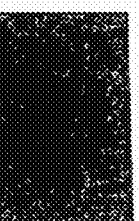

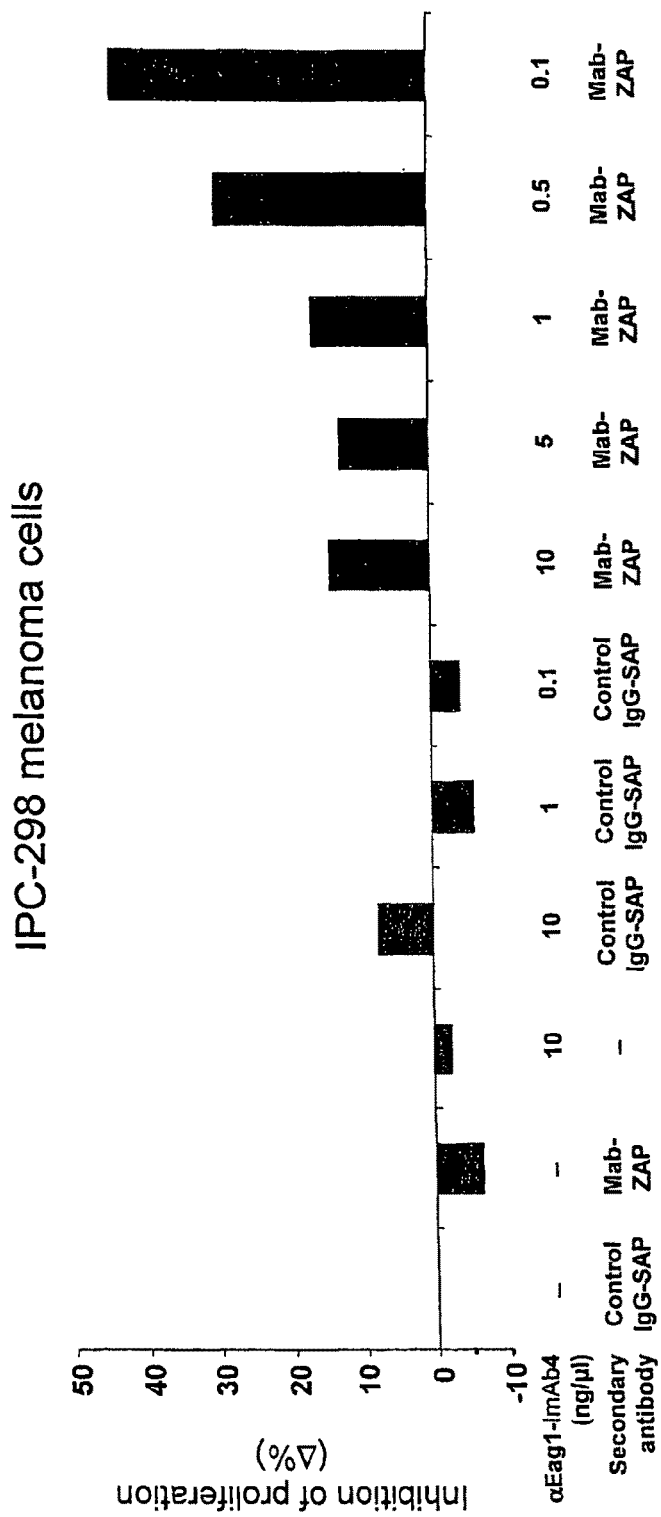

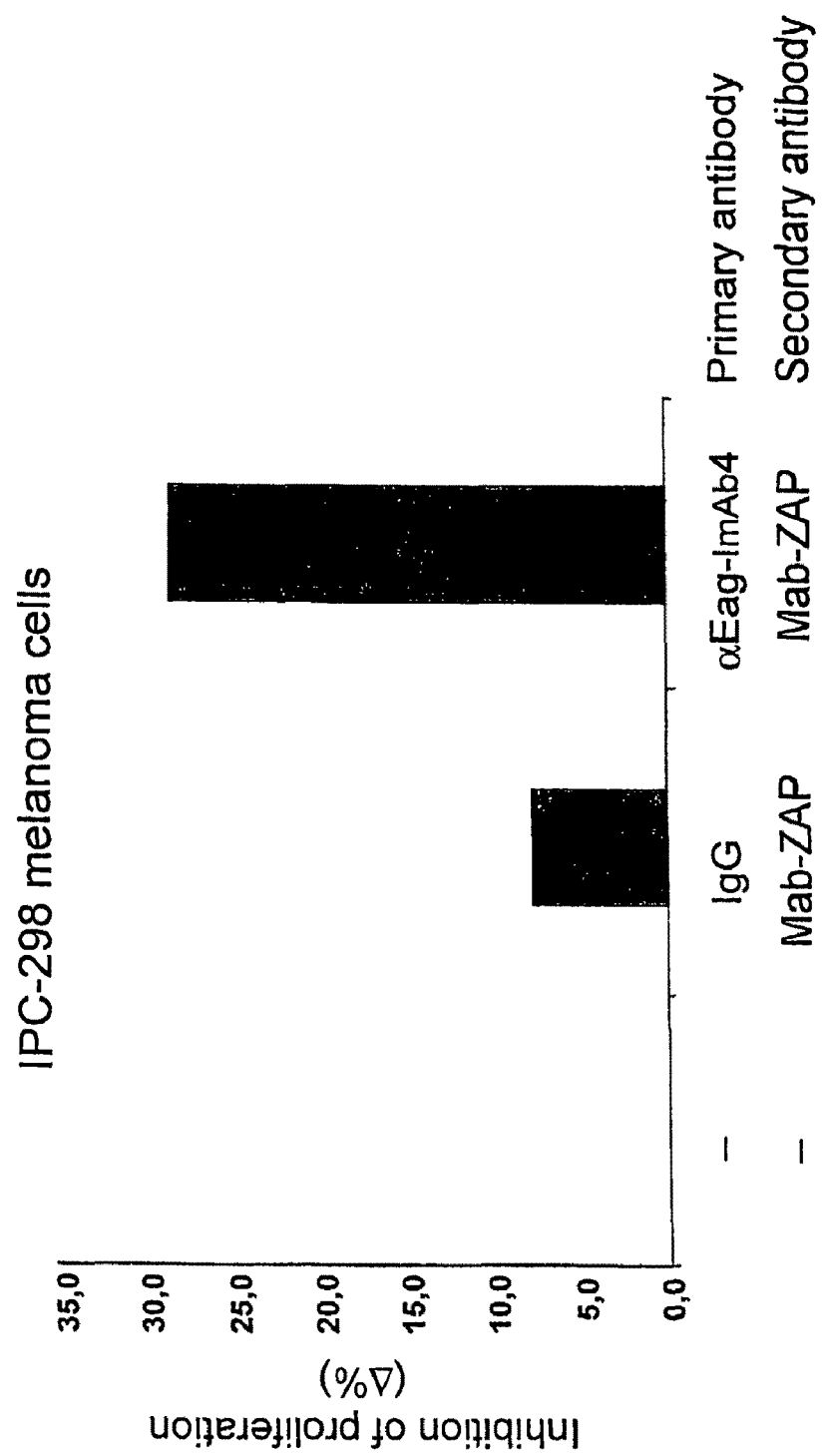

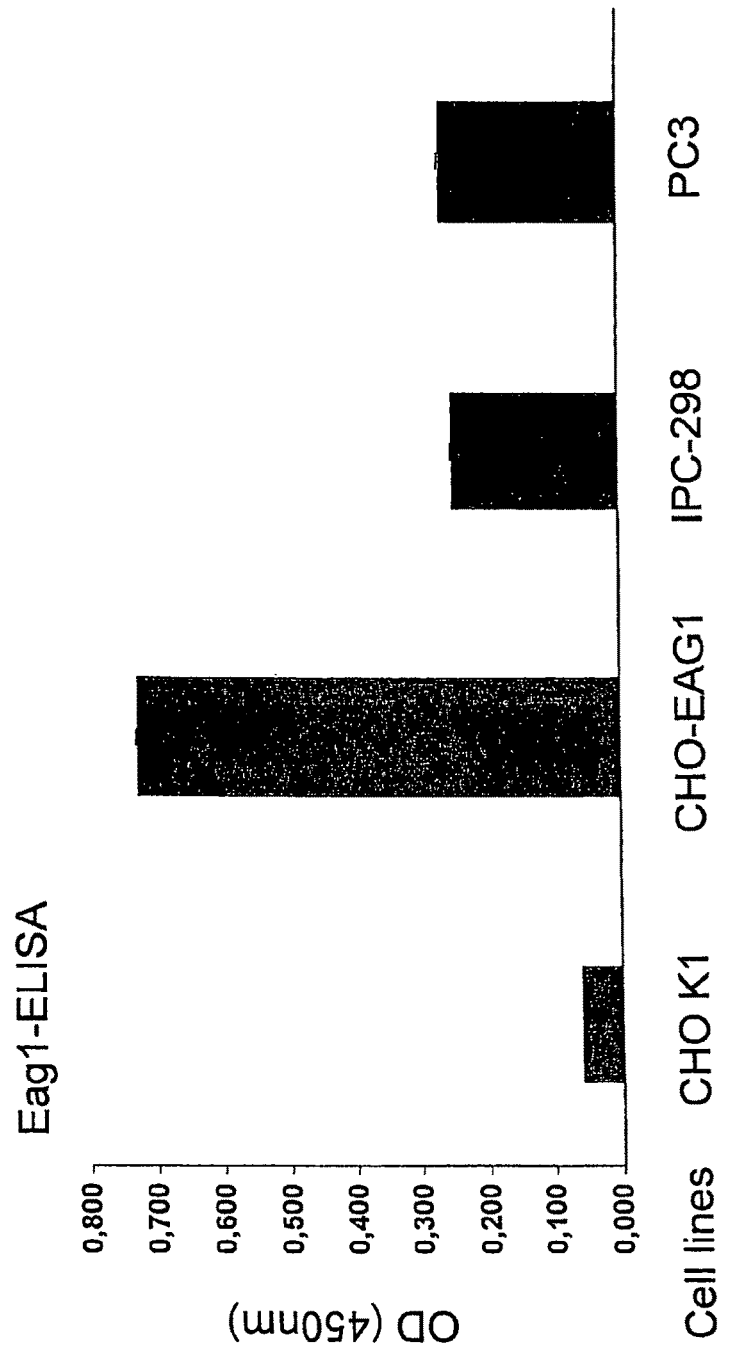

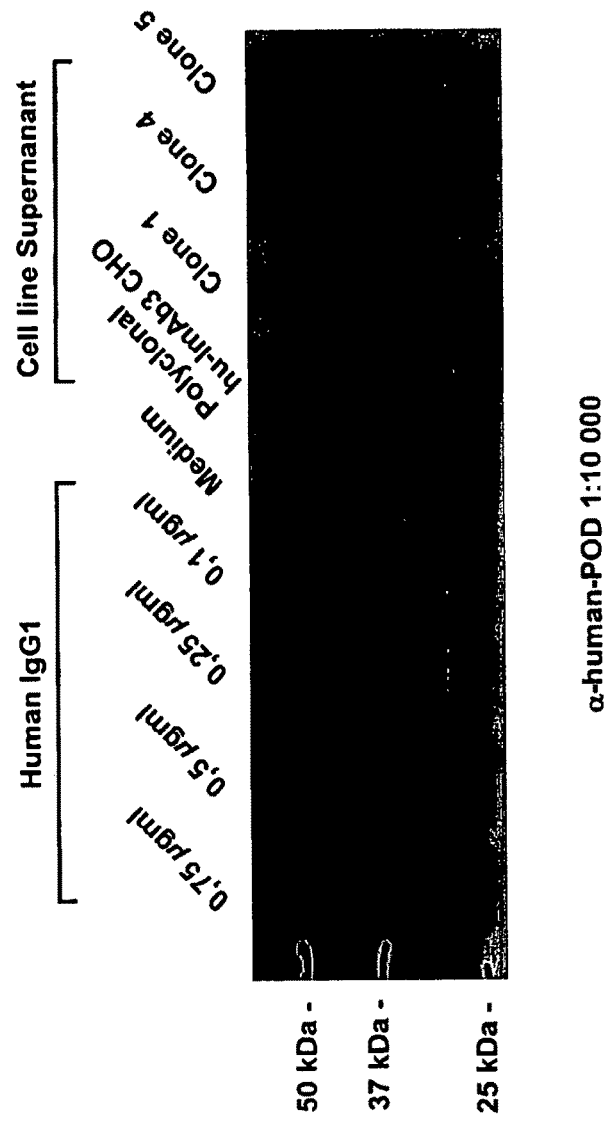

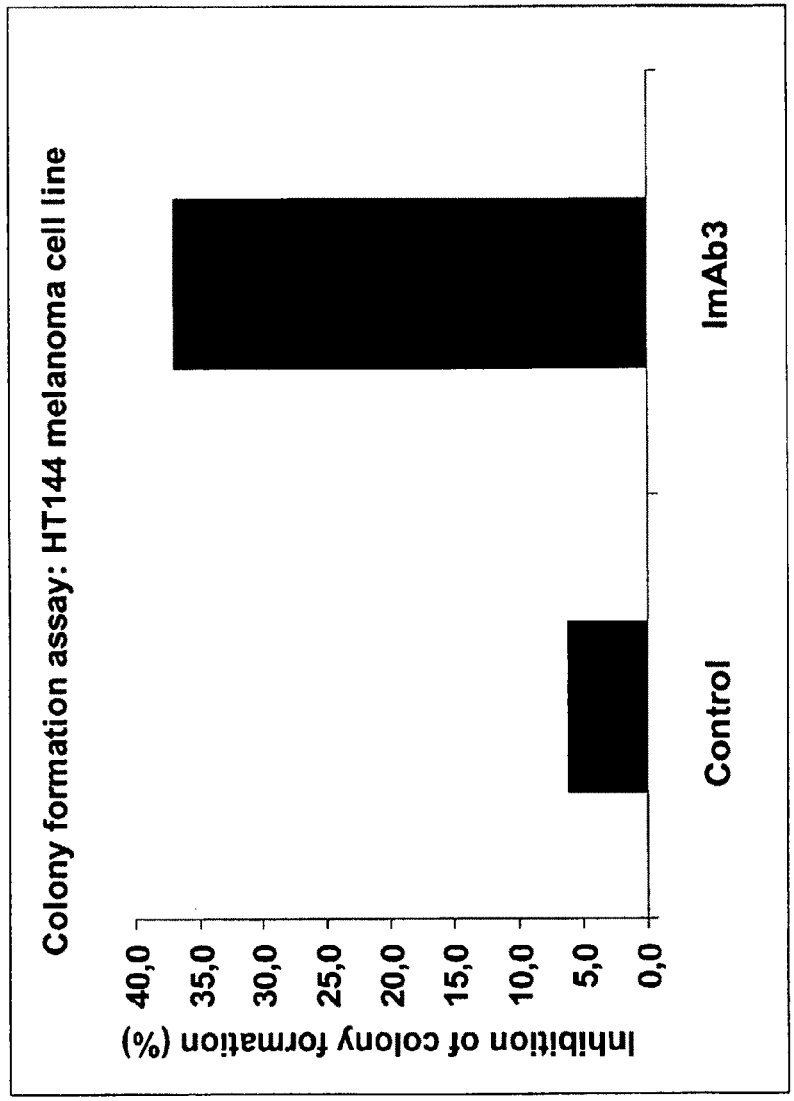
Fig. 12d Inhibition of colony formation of HT144 melanoma cells by anti-EAG1 antibody ImAb3

SEQUENCE LISTING

```
<160> NUMBER OF SEQ ID NOS: 270

<210> SEQ ID NO 1
<211> LENGTH: 786
<212> TYPE: DNA
<213> ORGANISM: Mus musculus

<400> SEQUENCE: 1
gtaacaacgc agagtacgcg ggggactgat cagtctcctc aggctgtctc ctcaggttgc      60
ctcctcaaaa tgaagttgcc tgttaggctg ttggtgctga tgttctggat tcctgcttcc     120
agcagtgatg ttgtgatgac ccaaactcca ctctccctgc ctgtcagtct tggagatcaa     180
gcctccatct cttgcagatc tagtcagagc cttgtacaca gtaatggaaa cacctattta     240
```

```
cattggtacc tgcagaagcc aggccagtct ccaaagctcc tgatctacaa agtttccaac    300 cgatttctg gggtcccaga caggttcagt ggcagtggat cagggacaga tttcacactc     360
aagatcagca gagtggaggc tgaggatctg ggagtttatt tctgctctca aagtacacat    420
gttcctccga cgttcggtgg aggcaccaag ctggaaatca aacgggctga tgctgcacca    480
actgtatcca tcttcccacc atccagtgag cagttaacat ctggaggtgc ctcagtcgtg    540
tgcttcttga caacttcta ccccaaagac atcaatgtca agtggaagat tgatggcagt     600
gaacgacaaa atggcgtcct gaacagttgg actgatcagg acagcaaaga cagcacctac    660
agcatgagca gcaccctcac gttgaccaag gacgagtatg aacgacataa cagctatacc    720
tgtgaggcca ctcacaagac atcaacttca cccattgtca agagcttcaa caggaatgag    780
tgttag                                                               786
```

```
<210> SEQ ID NO 2
<211> LENGTH: 238
<212> TYPE: PRT
<213> ORGANISM: Mus musculus

<400> SEQUENCE: 2

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
                20                  25                  30

Ser Leu Gly Asp Gln Ala Ser Ile Ser Cys Arg Ser Ser Gln Ser Leu
            35                  40                  45

Val His Ser Asn Gly Asn Thr Tyr Leu His Trp Tyr Leu Gln Lys Pro
        50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
                100                 105                 110

Ser Gln Ser Thr His Val Pro Pro Thr Phe Gly Gly Gly Thr Lys Leu
            115                 120                 125

Glu Ile Lys Arg Ala Asp Ala Ala Pro Thr Val Ser Ile Phe Pro Pro
        130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

```
<210> SEQ ID NO 3
<211> LENGTH: 1562
<212> TYPE: DNA
<213> ORGANISM: Mus musculus

<400> SEQUENCE: 3
```

```
gtaacaacgc agagtacgcg gggacatcgc tctcactgga ggctgatctc tgaagataag    60
gaggtgtagc ctaaaagatg agagtgctga ttcttttgtg gctgttcaca gcctttcctg   120
gtatcctgtc tgatgtgcag cttcaggagt cgggacctgg cctggtgaaa ccttctcagt   180
ctctgtccct cacctgcact gtcactggct actcaatcac cagtgattat gcctggaact   240
ggatccggca gtttccagga acaaactgga gtggatgggc tacataagct acagtggtag  300
gcactatcta caacccatct ctcaaaagtc gaatctctat cactcgagac acatccaaga   360
accagttctt cctgcagttg aattctgtga ctactgagga cacagccaca tattactgtg   420
caagatttgg taactacgga atactttgaa ctactgggg tcaaggaacc tcagtcaccg   480
tctcctcagc aaaacaaca cccccatcag tctatccact ggcccctggg tgtggagata   540
caactggttc ctccgtgact ctgggatgcc tggtcaaggg ctacttccct gagtcagtga   600
ctgtgacttg aactctgga tccctgtcca gcagtgtgca caccttccca gctctcctgc   660
agtctggact ctacactatg agcagctcag tgactgtccc ctccagcacc tggccaagtc   720
agaccgtcac ctgcagcgtt gctcacccag ccagcagcac acggtggac aaaaaacttg   780 agcccagcgg gcccatttca acaatcaacc cctgtcctcc atgcaaggag tgtcacaaat   840
gcccagctcc taacctcgag ggtggaccat ccgtcttcat cttccctcca aatatcaagg   900
atgtactcat gatctccctg cacccaaggt cacgtgtgt ggtggtggat gtgagcgagg   960
atgacccaga cgtccagatc agctggtttg tgaacaacgt ggaagtacac acagctcaga  1020
cacaaaccca tagagaggat tacaacagta ctatccgggt ggtcagcacc ctccccatcc  1080
agcaccagga ctggatgagt ggcaaggagt tcaaatgcaa ggtcaacaac aaagacctcc  1140
catcacccat cgagagaacc atctcaaaaa ttaaagggct agtcagagct ccacaagtat  1200
acatcttgcc gccaccagca gagcagttgt ccaggaaaga tgtcagtctc acttgcctgg  1260
tcgtgggctt caacccctgga gacatcagtg tggagtggac cagcaatggg catacagagg  1320
agaactacaa ggacaccgca ccagtcctgg actctgacgg ttcttacttc atatatagca  1380
agctcaatat gaaaacaagc aagtgggaga aacagattc cttctcatgc aacgtgagac  1440
acgagggtct gaaaaattac tacctgaaga agaccatctc ccggtctccg ggtaaatgaa  1500
tcaagcttat cgataccgtc gacctcgagg gggggcccgg tacccagctt ttgttccctt  1560
ta                                                                  1562
```

<210> SEQ ID NO 4
<211> LENGTH: 473
<212> TYPE: PRT
<213> ORGANISM: Mus musculus

<400> SEQUENCE: 4

```
Met Arg Val Leu Ile Leu Leu Trp Leu Phe Thr Ala Phe Pro Gly Ile
1               5                  10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Tyr Ala Trp Asn Trp Ile Arg Gln Phe Pro Gly Asn Lys Leu
    50                  55                  60

Glu Trp Met Gly Tyr Ile Ser Tyr Ser Gly Ser Thr Ile Tyr Asn Pro
65                  70                  75                  80

Ser Leu Lys Ser Arg Ile Ser Ile Thr Arg Asp Thr Ser Lys Asn Gln
                85                  90                  95
```

Phe Phe Leu Gln Leu Asn Ser Val Thr Thr Glu Asp Thr Ala Thr Tyr
            100                 105                 110

Tyr Cys Ala Arg Phe Gly Asn Tyr Gly Asn Thr Leu Asn Tyr Trp Gly
            115                 120                 125

Gln Gly Thr Ser Val Thr Val Ser Ser Ala Lys Thr Thr Pro Pro Ser
130                 135                 140

Val Tyr Pro Leu Ala Pro Gly Cys Gly Asp Thr Thr Gly Ser Ser Val
145                 150                 155                 160

Thr Leu Gly Cys Leu Val Lys Gly Tyr Phe Pro Glu Ser Val Thr Val
            165                 170                 175

Thr Trp Asn Ser Gly Ser Leu Ser Ser Val His Thr Phe Pro Ala
            180                 185                 190

Leu Leu Gln Ser Gly Leu Tyr Thr Met Ser Ser Val Thr Val Pro
            195                 200                 205

Ser Ser Thr Trp Pro Ser Gln Thr Val Thr Cys Ser Val Ala His Pro
210                 215                 220

Ala Ser Ser Thr Thr Val Asp Lys Lys Leu Glu Pro Ser Gly Pro Ile
225                 230                 235                 240

Ser Thr Ile Asn Pro Cys Pro Cys Lys Glu Cys His Lys Cys Pro
            245                 250                 255

Ala Pro Asn Leu Glu Gly Gly Pro Ser Val Phe Ile Phe Pro Pro Asn
            260                 265                 270

Ile Lys Asp Val Leu Met Ile Ser Leu Thr Pro Lys Val Thr Cys Val
            275                 280                 285

Val Val Asp Val Ser Glu Asp Asp Pro Asp Val Gln Ile Ser Trp Phe
            290                 295                 300

Val Asn Asn Val Glu Val His Thr Ala Gln Thr Gln Thr His Arg Glu
305                 310                 315                 320

Asp Tyr Asn Ser Thr Ile Arg Val Val Ser Thr Leu Pro Ile Gln His
            325                 330                 335

Gln Asp Trp Met Ser Gly Lys Glu Phe Lys Cys Lys Val Asn Asn Lys
            340                 345                 350

Asp Leu Pro Ser Pro Ile Glu Arg Thr Ile Ser Lys Ile Lys Gly Leu
            355                 360                 365

Val Arg Ala Pro Gln Val Tyr Ile Leu Pro Pro Ala Glu Gln Leu
            370                 375                 380

Ser Arg Lys Asp Val Ser Leu Thr Cys Leu Val Val Gly Phe Asn Pro
385                 390                 395                 400

Gly Asp Ile Ser Val Glu Trp Thr Ser Asn Gly His Thr Glu Glu Asn
            405                 410                 415

Tyr Lys Asp Thr Ala Pro Val Leu Asp Ser Asp Gly Ser Tyr Phe Ile
            420                 425                 430

Tyr Ser Lys Leu Asn Met Lys Thr Ser Lys Trp Glu Lys Thr Asp Ser
            435                 440                 445

Phe Ser Cys Asn Val Arg His Glu Gly Leu Lys Asn Tyr Tyr Leu Lys
450                 455                 460

Lys Thr Ile Ser Arg Ser Pro Gly Lys
465                 470

<210> SEQ ID NO 5
<211> LENGTH: 763
<212> TYPE: DNA
<213> ORGANISM: Mus musculus

<400> SEQUENCE: 5

```
gtaacaacgc agagtacgcg gggagacagg cagtgggagc aagatggatt cacaggccca    60
ggttcttata ttgctgctgc tatgggtatc tggtacctgt ggggacattg tgatgtcaca   120
gtctccatcc tccctggctg tgtcagcagg agagaaggtc actatgagct gcaaatccag   180
tcagagtctg ctcaacagta aacccgaaa gaactacttg gcttggtacc agcagaaacc   240
agggcagtct cctaaactgc tgatctactg ggcatccact agggaatctg ggtccctga   300 tcgcttcaca ggcagtggat ctgggacaga tttcactctc accatcagca gtgtgcaggc   360
tgaagacctg gcagtttatt actgcaagca atcttatgat cttcggacgt tcggtggagg   420
caccaagctg gaaatcaaac gggctgatgc tgcaccaact gtatccatct cccaccatc   480 cagtgagcag ttaacatctg gaggtgcctc agtcgtgtgc ttcttgaaca acttctaccc   540
caaagacatc aatgtcaagt ggaagattga tggcagtgaa cgacaaaatg gcgtcctgaa   600
cagttggact gatcaggaca gcaaagacag cacctacagc atgagcagca ccctcacgtt   660
gaccaaggac gagtatgaac gacataacag ctatacctgt gaggccactc acaagacatc   720
aacttcaccc attgtcaaga gcttcaacag gaatgagtgt tag                      763
```

<210> SEQ ID NO 6
<211> LENGTH: 239
<212> TYPE: PRT
<213> ORGANISM: Mus musculus

<400> SEQUENCE: 6

```
Met Asp Ser Gln Ala Gln Val Leu Ile Leu Leu Leu Trp Val Ser
1               5                   10                  15

Gly Thr Cys Gly Asp Ile Val Met Ser Gln Ser Pro Ser Ser Leu Ala
                20                  25                  30

Val Ser Ala Gly Glu Lys Val Thr Met Ser Cys Lys Ser Ser Gln Ser
            35                  40                  45

Leu Leu Asn Ser Arg Thr Arg Lys Asn Tyr Leu Ala Trp Tyr Gln Gln
        50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asp Leu Arg Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235
```

<210> SEQ ID NO 7
<211> LENGTH: 1588
<212> TYPE: DNA
<213> ORGANISM: Mus musculus

<400> SEQUENCE: 7

```
gtaacaacgc agagtacgcg ggggcgtatg aacctagccc tgatttcccc agccttcagt      60
tcccagattc agtgatcagc cttgaacaca gacctgtcac catgaagttg tggctgaact     120
ggatttcct tgtaacactt ttaaatggta ccagtgtga ggtgaagctg gtggagtctg      180
gaggaggctt ggtacagcct gggggttctc tgagactctc ctgtgcaact tctgggttca     240
ccttcactga ttactacatg agctgggtcc gccagcctcc aggaaaggca cttgagtggt     300
tgggttttat tagaaacaaa gctactggtt acacaacaga gtacagtgca tctgtgaagg     360
gtcggttcac catctccaga gataattccc aaagcatcct ctatcttcaa atgaacaccc     420
tgagagctga ggacagtgcc acttattact gtgcaagaga tttcggtagt aggtggtact     480
tcgatgtctg gggcgcaggg accacggtca ccgtctcctc agccaaaaca cacccccat     540
cagtctatcc actggcccct gggtgtggag atacaactgg ttcctccgtg actctgggat     600
gcctggtcaa gggctacttc cctgagtcag tgactgtgac ttggaactct ggatccctgt     660
ccagcagtgt gcacaccttc ccagctctcc tgcagtctgg actctacact atgagcagct     720
cagtgactgt cccctccagc acctggccaa gtcagaccgt cacctgcagc gttgctcacc     780
cagccagcag caccacggtg gacaaaaaac ttgagcccag cgggcccatt tcaacaatca     840
accctgtcc tccatgcaag gagtgtcaca atgcccagc tcctaacctc gagggtggac     900
catccgtctt catcttccct ccaaatatca aggatgtact catgatctcc ctgacaccca     960
aggtcacgtg tgtggtggtg gatgtgagcg aggatgaccc agacgtccag atcagctggt    1020
ttgtgaacaa cgtggaagta cacacagctc agacacaaac ccatagagag gattacaaca    1080
gtactatccg ggtggtcagc acccttccca tccagcacca ggactggatg agtggcaagg    1140
agttcaaatg caaggtcaac aacaaagacc tcccatcacc catcgagaga accatctcaa    1200
aaattaaagg gctagtcaga gctccacaag tatacatctt gccgccacca gcagagcagt    1260
tgtccaggaa agatgtcagt ctcacttgcc tggtcgtggg cttcaaccct ggagacatca    1320
gtgtggagtg gaccagcaat gggcatacag aggagaacta caaggacacc gcaccagtcc    1380
tggactctga cggttcttac ttcatatata gcaagctcaa tatgaaaaca gcaagtgggg    1440
agaaaacaga ttccttctca tgcaacgtga gacacgaggg tctgaaaaat tactacctga    1500
agaagaccat ctcccggtct ccgggtaaat gaatcaagct tatcgatacc gtcgacctcg    1560
agggggggcc cggtacccag cttttgtt                                       1588
```

<210> SEQ ID NO 8
<211> LENGTH: 476
<212> TYPE: PRT
<213> ORGANISM: Mus musculus

<400> SEQUENCE: 8

```
Met Lys Leu Trp Leu Asn Trp Ile Phe Leu Val Thr Leu Leu Asn Gly
 1               5                  10                  15

Ile Gln Cys Glu Val Lys Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

Thr Asp Tyr Tyr Met Ser Trp Val Arg Gln Pro Pro Gly Lys Ala Leu
```

-continued

```
                50                  55                  60
Glu Trp Leu Gly Phe Ile Arg Asn Lys Ala Thr Gly Tyr Thr Thr Glu
65                  70                  75                  80

Tyr Ser Ala Ser Val Lys Gly Arg Phe Thr Ile Ser Arg Asp Asn Ser
                85                  90                  95

Gln Ser Ile Leu Tyr Leu Gln Met Asn Thr Leu Arg Ala Glu Asp Ser
            100                 105                 110

Ala Thr Tyr Tyr Cys Ala Arg Asp Phe Gly Ser Arg Trp Tyr Phe Asp
        115                 120                 125

Val Trp Gly Ala Gly Thr Thr Val Thr Val Ser Ser Ala Lys Thr Thr
130                 135                 140

Pro Pro Ser Val Tyr Pro Leu Ala Pro Gly Cys Gly Asp Thr Thr Gly
145                 150                 155                 160

Ser Ser Val Thr Leu Gly Cys Leu Val Lys Gly Tyr Phe Pro Glu Ser
                165                 170                 175

Val Thr Val Thr Trp Asn Ser Gly Ser Leu Ser Ser Val His Thr
            180                 185                 190

Phe Pro Ala Leu Leu Gln Ser Gly Leu Tyr Thr Met Ser Ser Ser Val
        195                 200                 205

Thr Val Pro Ser Ser Thr Trp Pro Ser Gln Thr Val Thr Cys Ser Val
210                 215                 220

Ala His Pro Ala Ser Ser Thr Thr Val Asp Lys Lys Leu Glu Pro Ser
225                 230                 235                 240

Gly Pro Ile Ser Thr Ile Asn Pro Cys Pro Pro Cys Lys Glu Cys His
                245                 250                 255

Lys Cys Pro Ala Pro Asn Leu Glu Gly Gly Pro Ser Val Phe Ile Phe
            260                 265                 270

Pro Pro Asn Ile Lys Asp Val Leu Met Ile Ser Leu Thr Pro Lys Val
        275                 280                 285

Thr Cys Val Val Val Asp Val Ser Glu Asp Asp Pro Asp Val Gln Ile
290                 295                 300

Ser Trp Phe Val Asn Asn Val Glu Val His Thr Ala Gln Thr Gln Thr
305                 310                 315                 320

His Arg Glu Asp Tyr Asn Ser Thr Ile Arg Val Val Ser Thr Leu Pro
                325                 330                 335

Ile Gln His Gln Asp Trp Met Ser Gly Lys Glu Phe Lys Cys Lys Val
            340                 345                 350

Asn Asn Lys Asp Leu Pro Ser Pro Ile Glu Arg Thr Ile Ser Lys Ile
        355                 360                 365

Lys Gly Leu Val Arg Ala Pro Gln Val Tyr Ile Leu Pro Pro Pro Ala
370                 375                 380

Glu Gln Leu Ser Arg Lys Asp Val Ser Leu Thr Cys Leu Val Val Gly
385                 390                 395                 400

Phe Asn Pro Gly Asp Ile Ser Val Glu Trp Thr Ser Asn Gly His Thr
                405                 410                 415

Glu Glu Asn Tyr Lys Asp Thr Ala Pro Val Leu Asp Ser Asp Gly Ser
            420                 425                 430

Tyr Phe Ile Tyr Ser Lys Leu Asn Met Lys Thr Ser Lys Trp Glu Lys
        435                 440                 445

Thr Asp Ser Phe Ser Cys Asn Val Arg His Glu Gly Leu Lys Asn Tyr
450                 455                 460

Tyr Leu Lys Lys Thr Ile Ser Arg Ser Pro Gly Lys
465                 470                 475
```

-continued

<210> SEQ ID NO 9
<211> LENGTH: 794
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 9

```
acgcggggag acaggcagtg ggagcaagat ggattcacag gcccaggttc ttatattgct      60
gctgctatgg gtatctggta cctgtgggga cattgtgatg tcacagtctc catcctccct     120
ggctgtgtca gcaggagaga aggtcactat gagctgcaaa tccagtcaga gtctgctcaa     180
cagtagaacc cgaaagaact acttggcttg gtaccagcag aaaccagggc agtctcctaa     240
actgctgatc tactgggcat ccactaggga atctggggtc cctgatcgct tcacaggcag     300
tggatctggg acagatttca ctctcaccat cagcagtgtg caggctgaag acctggcagt     360
ttattactgc aagcaatctt atgatcttcg gacgttcggc ggagggacca aggtggagat     420
caaacgaact gtggctgcac catctgtctt catcttcccg ccatctgatg agcagttgaa     480
atctggaact gcctctgttg tgtgcctgct gaataacttc tatcccagag aggccaaagt     540
acagtggaag gtggataacg ccctccaatc gggtaactcc caggagagtg tcacagagca     600
ggacagcaag gacagcacct acagcctcag cagcaccctg acgctgagca agcagacta     660
cgagaaacac aaagtctacg cctgcgaagt cacccatcag ggcctgagct cgcccgtcac     720
aaagagcttc aacaggggtg agtgttagct cgagtgatat caagcttatc gataccgtcg     780
acctcgaggg gggg                                                       794
```

<210> SEQ ID NO 10
<211> LENGTH: 239
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 10

```
Met Asp Ser Gln Ala Gln Val Leu Ile Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asp Leu Arg Thr Phe Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160
```

```
Leu Asn Asn Phe Tyr Pro Arg Glu Ala Lys Val Gln Trp Lys Val Asp
            165                 170                 175

Asn Ala Leu Gln Ser Gly Asn Ser Gln Glu Ser Val Thr Glu Gln Asp
        180                 185                 190

Ser Lys Asp Ser Thr Tyr Ser Leu Ser Ser Thr Leu Thr Leu Ser Lys
    195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 11
<211> LENGTH: 1514
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 11
gtaacaacgc agagtacgcg ggggcgtatg aacctagccc tgatttcccc agccttcagt      60
tcccagattc agtgatcagc cttgaacaca gacctgtcac catgaagttg tggctgaact     120
ggatttccct tgtaacactt ttaaatggta tccagtgtga ggtgaagctg gtggagtctg     180
gaggaggctt ggtacagcct gggggttctc tgagactctc ctgtgcaact tctggttca     240
ccttcactga ttactacatg agctgggtcc gccagcctcc aggaaaggca cttgagtggt     300
tgggttttat tagaaacaaa gctactggtt acacaacaga gtacagtgca tctgtgaagg     360
gtcggttcac catctccaga gataattccc aaagcatcct ctatcttcaa atgaacaccc     420
tgagagctga ggacagtgcc acttattact gtgcaagaga tttcggtagt aggtggtact     480
tcgatgtctg ggcccaggga accctggtca ccgtctcctc agcctccacc aagggcccat     540
cggtcttccc cctggcaccc tcctccaaga gcacctctgg gggcacagcg gccctgggct     600
gcctggtcaa ggactacttc cccgaaccgg tgacggtgtc gtggaactca ggcgccctga     660
ccagcggcgt gcacaccttc ccggctgtcc tacagtcctc aggactctac tccctcagca     720
gcgtggtgac cgtgccctcc agcagcttgg cacccagac ctacatctgc aacgtgaatc     780
acaagcccag caacaccaag gtggacaaga agttgagcc caaatcttgt gacaaaactc     840
acacatgccc accgtgccca gcacctgaac tcctgggggg accgtcagtc ttcctcttcc     900
ccccaaaacc caaggacacc ctcatgatct cccggacccc tgaggtcaca tgcgtggtgg     960
tggacgtgag ccacgaagac cctgaggtca agttcaactg gtacgtggac ggcgtggagg    1020
tgcataatgc caagacaaag ccgcgggagg agcagtacaa cagcacgtac cgtgtggtca    1080
gcgtcctcac cgtcctgcac caggactggc tgaatggcaa ggagtacaag tgcaaggtct    1140
ccaacaaagc cctcccagcc cccatcgaga aaaccatctc caaagccaaa gggcagcccc    1200
gagaaccaca ggtgtacacc ctgcccccat cccgggatga gctgaccaag aaccaggtca    1260
gcctgacctg cctggtcaaa ggcttctatc cagcgacat cgccgtggag tgggagagca    1320
atgggcagcc ggagaacaac tacaagacca cgcctcccgt gctggactcc gacggctcct    1380
tcttcctcta tagcaagctc accgtggaca agagcaggtg gcagcagggg aacgtcttct    1440
catgctccgt gatgcatgag gctctgcaca accactacac gcagaagagc ctctccctgt    1500
ctccgggtaa atga                                                      1514

<210> SEQ ID NO 12
```

<211> LENGTH: 470
<212> TYPE: PRT
<213> ORGANISM: Artificial Sequence
<220> FEATURE:
<223> OTHER INFORMATION: Description of Artificial Sequence: Synthetic construct

<400> SEQUENCE: 12

Met Lys Leu Trp Leu Asn Trp Ile Phe Leu Val Thr Leu Leu Asn Gly
1               5                   10                  15

Ile Gln Cys Glu Val Lys Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

Thr Asp Tyr Tyr Met Ser Trp Val Arg Gln Pro Pro Gly Lys Ala Leu
    50                  55                  60

Glu Trp Leu Gly Phe Ile Arg Asn Lys Ala Thr Gly Tyr Thr Thr Glu
65                  70                  75                  80

Tyr Ser Ala Ser Val Lys Gly Arg Phe Thr Ile Ser Arg Asp Asn Ser
                85                  90                  95

Gln Ser Ile Leu Tyr Leu Gln Met Asn Thr Leu Arg Ala Glu Asp Ser
            100                 105                 110

Ala Thr Tyr Tyr Cys Ala Arg Asp Phe Gly Ser Arg Trp Tyr Phe Asp
        115                 120                 125

Val Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

```
Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
        450                 455                 460

Ser Leu Ser Pro Gly Lys
465             470

<210> SEQ ID NO 13
<211> LENGTH: 750
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 13
atgaagttgc ctgttaggct gttggtgctg atgttctgga ttcctgcttc cagcagtgat        60
gttgtgatga cccaaactcc actctccctg cctgtcagtc ttggagatca agcctccatc       120
tcttgcagat ctagtcagag ccttgtacac agtaatggaa acacctattt acattggtac       180
ctgcagaagc caggccagtc tccaaagctc ctgatctaca agtttccaa ccgatttttct       240 ggggtcccag acaggttcag tggcagtgga tcagggacag atttcacact caagatcagc       300
agagtggagg ctgaggatct gggagtttat ttctgctctc aaagtacaca tgttcctccg       360
acgttcggcg agggaccaa ggtggagatc aaacgaactg tggctgcacc atctgtcttc       420
atcttcccgc catctgatga gcagttgaaa tctggaactg cctctgttgt gtgcctgctg       480
aataacttct atcccagaga ggccaaagta cagtggaagg tggataacgc cctccaatcg       540
ggtaactccc aggagagtgt cacagagcag gacagcaagg acagcaccta cagcctcagc       600
agcaccctga cgctgagcaa agcagactac gagaaacaca agtctacgc ctgcgaagtc       660 acccatcagg gcctgagctc gcccgtcaca aagagcttca cagggggtga gtgttagctc       720
gagtgatatc gaattcctgc agcccggggg                                        750

<210> SEQ ID NO 14
<211> LENGTH: 228
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 14

Met Phe Trp Ile Pro Ala Ser Ser Asp Val Val Met Thr Gln Thr
1               5                   10                  15

Pro Leu Ser Leu Pro Val Ser Leu Gly Asp Gln Ala Ser Ile Ser Cys
            20                  25                  30

Arg Ser Ser Gln Ser Leu Val His Ser Asn Gly Asn Thr Tyr Leu His
        35                  40                  45

Trp Tyr Leu Gln Lys Pro Gly Gln Ser Pro Lys Leu Leu Ile Tyr Lys
    50                  55                  60

Val Ser Asn Arg Phe Ser Gly Val Pro Asp Arg Phe Ser Gly Ser Gly
```

```
                65                  70                  75                  80
Ser Gly Thr Asp Phe Thr Leu Lys Ile Ser Arg Val Glu Ala Glu Asp
                    85                  90                  95
Leu Gly Val Tyr Phe Cys Ser Gln Ser Thr His Val Pro Pro Thr Phe
                100                 105                 110
Gly Gly Gly Thr Lys Val Glu Ile Lys Arg Thr Val Ala Ala Pro Ser
                115                 120                 125
Val Phe Ile Phe Pro Pro Ser Asp Glu Gln Leu Lys Ser Gly Thr Ala
    130                 135                 140
Ser Val Val Cys Leu Leu Asn Asn Phe Tyr Pro Arg Glu Ala Lys Val
145                 150                 155                 160
Gln Trp Lys Val Asp Asn Ala Leu Gln Ser Gly Asn Ser Gln Glu Ser
                165                 170                 175
Val Thr Glu Gln Asp Ser Lys Asp Ser Thr Tyr Ser Leu Ser Ser Thr
            180                 185                 190
Leu Thr Leu Ser Lys Ala Asp Tyr Glu Lys His Lys Val Tyr Ala Cys
        195                 200                 205
Glu Val Thr His Gln Gly Leu Ser Ser Pro Val Thr Lys Ser Phe Asn
    210                 215                 220
Arg Gly Glu Cys
225

<210> SEQ ID NO 15
<211> LENGTH: 1481
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 15
gtaacaacgc agagtacgcg gggacatcgc tctcactgga ggctgatctc tgaagataag      60
gaggtgtagc ctaaaagatg agagtgctga ttcttttgtg gctgttcaca gcctttcctg     120
gtatcctgtc tgatgtgcag cttcaggagt cgggacctgg cctggtgaaa ccttctcagt     180
ctctgtccct cacctgcact gtcactggct actcaatcac cagtgattat gcctggaact     240
ggatccggca gtttccagga aacaaactgg agtggatggg ctacataagc tacagtggta     300
gcactatcta caacccatct ctcaaaagtc gaatctctat cactcgagac acatccaaga     360
accagttctt cctgcagttg aattctgtga ctactgagga cacagccaca tattactgtg     420
caagatttgg taactacgga aatactttga actactgggg ccagggaacc ctggtcaccg     480
tctcctcagc ctccaccaag ggcccatcgg tcttccccct ggcaccctcc tccaagagca     540
cctctggggg cacagcggcc ctgggctgcc tggtcaagga ctacttcccc gaaccggtga     600
cggtgtcgtg gaactcaggc gccctgacca gcggcgtgca caccttcccg gctgtcctac     660
agtcctcagg actctactcc ctcagcagcg tggtgaccgt gccctccagc agcttgggca     720
cccagaccta catctgcaac gtgaatcaca agcccagcaa caccaaggtg gacaagaaag     780
ttgagcccaa atcttgtgac aaaactcaca catgcccacc gtgcccagca cctgaactcc     840
tggggggacc gtcagtcttc ctcttccccc caaaacccaa ggacaccctc atgatctccc     900
ggacccctga ggtcacatgc gtggtggtgg acgtgagcca cgaagaccct gaggtcaagt     960
tcaactggta cgtggacggc gtggaggtgc ataatgccaa gacaaagccg cgggaggagc    1020
agtacaacag cacgtaccgt gtggtcagcg tcctcaccgt cctgcaccag gactggctga    1080
atggcaagga gtacaagtgc aaggtctcca acaaagccct cccagccccc atcgagaaaa    1140
```

```
ccatctccaa agccaaaggg cagccccgag aaccacaggt gtacaccctg cccccatccc      1200
gggatgagct gaccaagaac caggtcagcc tgacctgcct ggtcaaaggc ttctatccca      1260
gcgacatcgc cgtggagtgg gagagcaatg ggcagccgga gaacaactac aagaccacgc      1320
ctcccgtgct ggactccgac ggctccttct tcctctatag caagctcacc gtggacaaga      1380
gcaggtggca gcaggggaac gtcttctcat gctccgtgat gcatgaggct ctgcacaacc      1440
actacacgca gaagagcctc tccctgtctc cgggtaaatg a                         1481
```

<210> SEQ ID NO 16
<211> LENGTH: 467
<212> TYPE: PRT
<213> ORGANISM: Artificial Sequence
<220> FEATURE:
<223> OTHER INFORMATION: Description of Artificial Sequence: Synthetic construct

<400> SEQUENCE: 16

```
Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Tyr Ala Trp Asn Trp Ile Arg Gln Phe Pro Gly Asn Lys Leu
    50                  55                  60

Glu Trp Met Gly Tyr Ile Ser Tyr Ser Gly Ser Thr Ile Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Ala Arg Phe Gly Asn Tyr Gly Asn Thr Leu Asn Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300
```

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 17
<211> LENGTH: 763
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 17
gtaacaacgc agagtacgcg gggagacagg cagtgggagc aagatggatt cacaggccca     60
ggttcttata ttgctgctgc tatgggtatc tggtacctgt ggggacattg tgatgacaca    120
gtctccagac tccctggctg tgtcactagg agagagggcc actataaact gcaaatccag    180
tcagagtctg ctcaacagta gaacccgaaa gaactacttg gcttggtacc agcagaaacc    240
agggcagcct cctaaactgc tgatctactg ggcatccact agggaatctg ggtccctga    300 tcgcttctca ggcagtggat ctgggacaga tttcactctc accatcagca gtctgcaggc    360
tgaagacgtg gcagtttatt actgcaagca atcttatgat cttcggacgt tcggcggagg    420
gaccaaggtg gagatcaaac gaactgtggc tgcaccatct gtcttcatct tcccgccatc    480
tgatgagcag ttgaaatctg gaactgcctc tgttgtgtgc ctgctgaata acttctatcc    540
cagagaggcc aaagtacagt ggaaggtgga taacgccctc caatcgggta actcccagga    600
gagtgtcaca gagcaggaca gcaaggacag cacctacagc ctcagcagca ccctgacgct    660
gagcaaagca gactacgaga aacacaaagt ctacgcctgc gaagtcaccc atcagggcct    720
gagctcgccc gtcacaaaga gcttcaacag gggtgagtgt tag                       763

<210> SEQ ID NO 18
<211> LENGTH: 239
<212> TYPE: PRT
<213> ORGANISM: Artificial Sequence
<220> FEATURE:
<223> OTHER INFORMATION: Description of Artificial Sequence: Synthetic
      construct -continued

<400> SEQUENCE: 18

```
Met Asp Ser Gln Ala Gln Val Leu Ile Leu Leu Leu Trp Val Ser
1               5                   10                  15

Gly Thr Cys Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Lys Gln Ser Tyr Asp Leu Arg Thr Phe Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 19
<211> LENGTH: 1514
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 19

```
gtaacaacgc agagtacgcg ggggcgtatg aacctagccc tgatttcccc agccttcagt    60
tcccagattc agtgatcagc cttgaacaca gacctgtcac catgaagttg tggctgaact   120 ggatttttcct tgtaacactt taaatggta ccagtgtga ggtgcagctg gtggagtctg    180
gaggaggctt ggtacagcct gggggttctc tgagactctc ctgtgcagct tctgggttca   240
ccttcactga ttactacatg agctgggtcc gccaggctcc aggaaaggga cttgagtggg   300
tgggttttat tagaaacaaa gctactggtt acacaacaga gtacagtgca tctgtgaagg   360
gtcggttcac catctccaga gatgattcca aaaacagcct ctatcttcaa atgaacagcc   420
tgaaaactga ggacactgcc gtttattact gtgcaagaga tttcggtagt aggtggtact   480
tcgatgtctg gggccaggga accctggtca ccgtctcctc agcctccacc aagggcccat   540
cggtcttccc cctggcaccc tcctccaaga gcacctctgg gggcacagcg gccctgggct   600
gcctggtcaa ggactacttc cccgaaccgg tgacggtgtc gtggaactca ggcgccctga   660
```

-continued

```
ccagcggcgt gcacaccttc ccggctgtcc tacagtcctc aggactctac tccctcagca    720
gcgtggtgac cgtgccctcc agcagcttgg cacccagac ctacatctgc aacgtgaatc     780
acaagcccag caacaccaag gtggacaaga agttgagcc caaatcttgt gacaaaactc     840
acacatgccc accgtgccca gcacctgaac tcctggggg accgtcagtc ttcctcttcc     900
ccccaaaacc caaggacacc ctcatgatct cccggacccc tgaggtcaca tgcgtggtgg    960
tggacgtgag ccacgaagac cctgaggtca agttcaactg gtacgtggac ggcgtggagg   1020
tgcataatgc caagacaaag ccgcgggagg agcagtacaa cagcacgtac cgtgtggtca   1080
gcgtcctcac cgtcctgcac caggactggc tgaatggcaa ggagtacaag tgcaaggtct   1140
ccaacaaagc cctcccagcc cccatcgaga aaaccatctc caaagccaaa gggcagcccc   1200
gagaaccaca ggtgtacacc ctgcccccat cccgggatga gctgaccaag aaccaggtca   1260
gcctgacctg cctggtcaaa ggcttctatc ccagcgacat cgccgtggag tgggagagca   1320
atgggcagcc ggagaacaac tacaagacca cgcctcccgt gctggactcc gacggctcct   1380
tcttcctcta tagcaagctc accgtggaca agagcaggtg gcagcagggg aacgtcttct   1440
catgctccgt gatgcatgag gctctgcaca accactacac gcagaagagc ctctcccgtgt  1500 ctccgggtaa atga                                                     1514
```

<210> SEQ ID NO 20
<211> LENGTH: 470
<212> TYPE: PRT
<213> ORGANISM: Artificial Sequence
<220> FEATURE:
<223> OTHER INFORMATION: Description of Artificial Sequence: Synthetic construct

<400> SEQUENCE: 20

```
Met Lys Leu Trp Leu Asn Trp Ile Phe Leu Val Thr Leu Leu Asn Gly
1               5                   10                  15

Ile Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Tyr Tyr Met Ser Trp Val Arg Gln Ala Pro Gly Lys Gly Leu
    50                  55                  60

Glu Trp Val Gly Phe Ile Arg Asn Lys Ala Thr Gly Tyr Thr Thr Glu
65                  70                  75                  80

Tyr Ser Ala Ser Val Lys Gly Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Ala Arg Asp Phe Gly Ser Arg Trp Tyr Phe Asp
        115                 120                 125

Val Trp Gly Gln Gly Thr Leu Val Thr Val Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205
```

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 21
<211> LENGTH: 898
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 21
aacgggccct ctatactcga gcggccgcca ctgtgctgga tgtaacaacg cagagtacgc      60
gggggactga tcagtctcct caggctgtct cctcaggttg cctcctcaaa atgaagttgc     120
ctgttaggct gttggtgctg atgttctgga ttcctgcttc cagcagtgat gttgtgatga     180
cccaaagtcc actctccctg cctgtcactc ttggacaacc agcctccatc tcttgcagat     240
ctagtcagag ccttgtacac agtaatggaa acacctattt acattggttc agcagaggc      300 caggccagtc tccaaggcgc ctgatctaca agtttccaa ccgattttct ggggtcccag     360
acaggttcag tggcagtgga tcagggacag atttcacact caagatcagc agagtggagg     420
ctgaggatgt gggagtttat tactgctctc aaagtacaca tgttcctccg acgttcggcg     480
gagggaccaa ggtggagatc aaacgaactg tggctgcacc atctgtcttc atcttcccgc     540

```
catctgatga gcagttgaaa tctggaactg cctctgttgt gtgcctgctg aataacttct      600
atcccagaga ggccaaagta cagtggaagg tggataacgc cctccaatcg ggtaactccc      660
aggagagtgt cacagagcag gacagcaagg acagcaccta cagcctcagc agcaccctga      720
cgctgagcaa agcagactac gagaaacaca aagtctacgc ctgcgaagtc acccatcagg      780
gcctgagctc gcccgtcaca aagagcttca cagggtga gtgttagatc tgcagaattc       840
caccacactg gactagggat ccgagctcgg taccaagctt aagtttaaac gctagcca       898
```

<210> SEQ ID NO 22
<211> LENGTH: 238
<212> TYPE: PRT
<213> ORGANISM: Artificial Sequence
<220> FEATURE:
<223> OTHER INFORMATION: Description of Artificial Sequence: Synthetic construct

<400> SEQUENCE: 22

```
Met Lys Leu Pro Val Arg Leu Leu Val Leu Met Phe Trp Ile Pro Ala
1               5                   10                  15

Ser Ser Ser Asp Val Val Met Thr Gln Ser Pro Leu Ser Leu Pro Val
            20                  25                  30

Thr Leu Gly Gln Pro Ala Ser Ile Ser Cys Arg Ser Ser Gln Ser Leu
        35                  40                  45

Val His Ser Asn Gly Asn Thr Tyr Leu His Trp Phe Gln Gln Arg Pro
    50                  55                  60

Gly Gln Ser Pro Arg Arg Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Ser Gln Ser Thr His Val Pro Pro Thr Phe Gly Gly Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 23
<211> LENGTH: 1481
<212> TYPE: DNA
<213> ORGANISM: Artificial Sequence
<220> FEATURE:
<223> OTHER INFORMATION: Description of Artificial Sequence: Synthetic construct

<400> SEQUENCE: 23

```
gtaacaacgc agagtacgcg gggacatcgc tctcactgga ggctgatctc tgaagataag      60
```

```
gaggtgtagc ctaaaagatg agagtgctga ttcttttgtg gctgttcaca gcctttcctg      120
gtatcctgtc tgatgtgcag cttcaggagt cgggacctgg cctggtgaaa ccttctgaga      180
ctctgtccct cacctgcact gtctctggct actcaatcac cagtgattat gcctggaact      240
ggatccggca gcctccagga aagggactgg agtggatcgg ctacataagc tacagtggta      300
gcactatcta caacccatct ctcaaaagtc gagtcactat cagtgtagac acatccaaga      360
accagttctc cctgaagttg agttctgtga ctgctgcgga cacagccgta tattactgtg      420
caagatttgg taactacgga atactttga actactgggg ccaggaaacc ctggtcaccg      480
tctcctcagc ctccaccaag ggcccatcgg tcttccccct ggcaccctcc tccaagagca      540
cctctggggg cacagcggcc ctgggctgcc tggtcaagga ctacttcccc gaaccggtga      600
cggtgtcgtg gaactcaggc gccctgacca gcggcgtgca caccttcccg gctgtcctac      660
agtcctcagg actctactcc ctcagcagcg tggtgaccgt gccctccagc agcttgggca      720
cccagaccta catctgcaac gtgaatcaca agcccagcaa caccaaggtg gacaagaaag      780
ttgagcccaa atcttgtgac aaaactcaca catgcccacc gtgcccagca cctgaactcc      840
tggggggacc gtcagtcttc ctcttccccc caaaacccaa ggacaccctc atgatctccc      900
ggacccctga ggtcacatgc gtggtggtgg acgtgagcca cgaagaccct gaggtcaagt      960
tcaactggta cgtggacggc gtggaggtgc ataatgccaa gacaaagccg cgggaggagc     1020
agtacaacag cacgtaccgt gtggtcagcg tcctcaccgt cctgcaccag gactggctga     1080
atggcaagga gtacaagtgc aaggtctcca acaaagccct cccagccccc atcgagaaaa     1140
ccatctccaa agccaaaggg cagccccgag aaccacaggt gtacaccctg cccccatccc     1200
gggatgagct gaccaagaac caggtcagcc tgacctgcct ggtcaaaggc ttctatccca     1260
gcgacatcgc cgtggagtgg gagagcaatg ggcagccgga gaacaactac aagaccacgc     1320
ctcccgtgct ggactccgac ggctccttct tcctctatag caagctcacc gtggacaaga     1380
gcaggtggca gcagggaac gtcttctcat gctccgtgat gcatgaggct ctgcacaacc     1440
actacacgca gaagagcctc tccctgtctc cgggtaaatg a                        1481
```

<210> SEQ ID NO 24
<211> LENGTH: 467
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 24

```
Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
            20                  25                  30

Ser Glu Thr Leu Ser Leu Thr Cys Thr Val Ser Gly Tyr Ser Ile Thr
        35                  40                  45

Ser Asp Tyr Ala Trp Asn Trp Ile Arg Gln Pro Gly Lys Gly Leu
    50                  55                  60

Glu Trp Ile Gly Tyr Ile Ser Tyr Ser Gly Ser Thr Ile Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110
```

Tyr Cys Ala Arg Phe Gly Asn Tyr Gly Asn Thr Leu Asn Tyr Trp Gly
            115                 120                 125

Gln Gly Thr Leu Val Thr Val Ser Ser Ala Ser Thr Lys Gly Pro Ser
            130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
            210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
            290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 25
<211> LENGTH: 813
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 25

```
cttggtaccg agctcggatc cctagtccag tgtggtggaa ttctgcagat gtaacaacgc    60
agagtacgcg gggagacagg cagtgggagc aagatggatt cacaggccca ggttcttata   120
ttgctgctgc tatgggtatc tggtacctgt ggggacattg tgatgacaca gtctccactc   180
tccctgcctg tgacaccagg agagccggcc tctataagct gcaaatccag tcagagtctg   240
ctcaacagta aacccgaaa gaactacttg gcttggtacc tgcagaaacc agggcagtct    300
cctcaactgc tgatctactg ggcatccact agggaatctg gggtcccctga tcgcttctca  360 ggcagtggat ctgggacaga tttcactctc aaaatcagca gagtggaggc tgaagacgtg   420
ggagtttatt actgcaagca atcttatgat cttcggacgt tcggcggagg gaccaaggtg   480
gagatcaaac gaactgtggc tgcaccatct gtcttcatct cccgccatc tgatgagcag    540 ttgaaatctg gaactgcctc tgttgtgtgc ctgctgaata acttctatcc agagaggcc    600 aaagtacagt ggaaggtgga taacgccctc caatcgggta actcccagga gagtgtcaca   660
gagcaggaca gcaaggacag cacctacagc ctcagcagca ccctgacgct gagcaaagca   720
gactacgaga aacacaaagt ctacgcctgc gaagtcaccc atcagggcct gagctcgccc   780
gtcacaaaga gcttcaacag gggtgagtgt tag                                813
```

<210> SEQ ID NO 26
<211> LENGTH: 239
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 26

```
Met Asp Ser Gln Ala Gln Val Leu Ile Leu Leu Leu Leu Trp Val Ser
1               5                   10                  15

Gly Thr Cys Gly Asp Ile Val Met Thr Gln Ser Pro Leu Ser Leu Pro
            20                  25                  30

Val Thr Pro Gly Glu Pro Ala Ser Ile Ser Cys Lys Ser Ser Gln Ser
        35                  40                  45

Leu Leu Asn Ser Arg Thr Arg Lys Asn Tyr Leu Ala Trp Tyr Leu Gln
    50                  55                  60

Lys Pro Gly Gln Ser Pro Gln Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Lys Gln Ser Tyr Asp Leu Arg Thr Phe Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
```

```
            210                 215                 220
Gly Leu Ser Ser Pro Val Thr Lys Ser Phe Asn Arg Gly Glu Cys
        225                 230                 235

<210> SEQ ID NO 27
<211> LENGTH: 1558
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 27
tcgacggtat cgataagctt gatatcaaag cttacaacgc agagtacgcg ggggcgtatg     60
aacctagccc tgatttcccc agccttcagt tcccagattc agtgatcagc cttgaacaca    120
gacctgtcac catgaagttg tggctgaact ggattttcct tgtaacactt ttaaatggta    180
tccagtgtga ggtgcagctg ttggagtctg gaggaggctt ggtacagcct ggggggttctc    240 tgagactctc ctgtgcagct tctgggttca ccttcactga ttactacatg agctgggtcc    300
gccaggctcc aggaaaggga cttgagtggg tgagttttat tagaaacaaa gctactggtt    360
acacaacaga gtacagtgca tctgtgaagg gtcggttcac catctccaga gataattcca    420
aaaacaccct ctatcttcaa atgaacagcc tgagagctga ggacactgcc gtttattact    480
gtgcaaagga ttttggtagt aggtggtact cgatgtctg gggccaggga accctggtca    540
ccgtctcctc agcctccacc aagggcccat cggtcttccc cctggcaccc tcctccaaga    600
gcacctctgg gggcacagcg gccctgggct gcctggtcaa ggactacttc cccgaaccgg    660
tgacggtgtc gtggaactca ggcgccctga ccagcggcgt gcacaccttc ccggctgtcc    720
tacagtcctc aggactctac tccctcagca gcgtggtgac cgtgccctcc agcagcttgg    780
gcacccagac ctacatctgc aacgtgaatc acaagcccag caacaccaag gtggacaaga    840
aagttgagcc caaatcttgt gacaaaactc acacatgccc accgtgccca gcacctgaac    900
tcctgggggg accgtcagtc ttcctcttcc ccccaaaacc caaggacacc ctcatgatct    960
cccggacccc tgaggtcaca tgcgtggtgg tggacgtgag ccacgaagac cctgaggtca   1020
agttcaactg gtacgtggac ggcgtggagg tgcataatgc caagacaaag ccgcgggagg   1080
agcagtacaa cagcacgtac cgtgtggtca gcgtcctcac cgtcctgcac caggactggc   1140
tgaatggcaa ggagtacaag tgcaaggtct ccaacaaagc cctcccagcc cccatcgaga   1200
aaaccatctc caaagccaaa gggcagcccc gagaaccaca ggtgtacacc ctgcccccat   1260
cccgggatga gctgaccaag aaccaggtca gcctgacctg cctggtcaaa ggcttctatc   1320
ccagcgacat cgccgtggag tgggagagca atgggcagcc ggagaacaac tacaagacca   1380
cgcctcccgt gctggactcc gacggctcct tcttcctcta tagcaagctc accgtggaca   1440
agagcaggtg gcagcagggg aacgtcttct catgctccgt gatgcatgag gctctgcaca   1500
accactacac gcagaagagc ctctccctgt ctccgggtaa atgatctaga tgatatcg    1558

<210> SEQ ID NO 28
<211> LENGTH: 470
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 28

Met Lys Leu Trp Leu Asn Trp Ile Phe Leu Val Thr Leu Leu Asn Gly
```

```
  1               5                  10                 15
Ile Gln Cys Glu Val Gln Leu Leu Glu Ser Gly Gly Gly Leu Val Gln
                 20                 25                 30

Pro Gly Gly Ser Leu Arg Leu Ser Cys Ala Ala Ser Gly Phe Thr Phe
             35                 40                 45

Thr Asp Tyr Tyr Met Ser Trp Val Arg Gln Ala Pro Gly Lys Gly Leu
         50                 55                 60

Glu Trp Val Ser Phe Ile Arg Asn Lys Ala Thr Gly Tyr Thr Thr Glu
 65                 70                 75                 80

Tyr Ser Ala Ser Val Lys Gly Arg Phe Thr Ile Ser Arg Asp Asn Ser
                 85                 90                 95

Lys Asn Thr Leu Tyr Leu Gln Met Asn Ser Leu Arg Ala Glu Asp Thr
             100                105                110

Ala Val Tyr Tyr Cys Ala Lys Asp Phe Gly Ser Arg Trp Tyr Phe Asp
         115                120                125

Val Trp Gly Gln Gly Thr Leu Val Thr Val Ser Ser Ala Ser Thr Lys
             130                135                140

Gly Pro Ser Val Phe Pro Leu Ala Pro Ser Ser Lys Ser Thr Ser Gly
145                150                155                160

Gly Thr Ala Ala Leu Gly Cys Leu Val Lys Asp Tyr Phe Pro Glu Pro
             165                170                175

Val Thr Val Ser Trp Asn Ser Gly Ala Leu Thr Ser Gly Val His Thr
             180                185                190

Phe Pro Ala Val Leu Gln Ser Ser Gly Leu Tyr Ser Leu Ser Ser Val
         195                200                205

Val Thr Val Pro Ser Ser Ser Leu Gly Thr Gln Thr Tyr Ile Cys Asn
         210                215                220

Val Asn His Lys Pro Ser Asn Thr Lys Val Asp Lys Lys Val Glu Pro
225                230                235                240

Lys Ser Cys Asp Lys Thr His Thr Cys Pro Pro Cys Pro Ala Pro Glu
             245                250                255

Leu Leu Gly Gly Pro Ser Val Phe Leu Phe Pro Pro Lys Pro Lys Asp
             260                265                270

Thr Leu Met Ile Ser Arg Thr Pro Glu Val Thr Cys Val Val Val Asp
         275                280                285

Val Ser His Glu Asp Pro Glu Val Lys Phe Asn Trp Tyr Val Asp Gly
         290                295                300

Val Glu Val His Asn Ala Lys Thr Lys Pro Arg Glu Glu Gln Tyr Asn
305                310                315                320

Ser Thr Tyr Arg Val Val Ser Val Leu Thr Val Leu His Gln Asp Trp
                 325                330                335

Leu Asn Gly Lys Glu Tyr Lys Cys Lys Val Ser Asn Lys Ala Leu Pro
             340                345                350

Ala Pro Ile Glu Lys Thr Ile Ser Lys Ala Lys Gly Gln Pro Arg Glu
         355                360                365

Pro Gln Val Tyr Thr Leu Pro Pro Ser Arg Asp Glu Leu Thr Lys Asn
     370                375                380

Gln Val Ser Leu Thr Cys Leu Val Lys Gly Phe Tyr Pro Ser Asp Ile
385                390                395                400

Ala Val Glu Trp Glu Ser Asn Gly Gln Pro Glu Asn Asn Tyr Lys Thr
             405                410                415

Thr Pro Pro Val Leu Asp Ser Asp Gly Ser Phe Phe Leu Tyr Ser Lys
             420                425                430
```

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465             470

<210> SEQ ID NO 29
<211> LENGTH: 772
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 29
atcagcggcc gcacaacgca gagtacgcgg ggagacaggc agtgggagca agatggattc      60
acaggcccag gttcttatat tgctgctgct atgggtatct ggtacctgtg gggacgttgt     120
gatgacacag tctccactct ccctgcctgt gacactagga cagccggcct ctataagctg     180
caaatccagt cagagtctgc tcaacagtag aacccgaaag aactacttgg cttggttcca     240
gcagagacca gggcagtctc ctagactgcg gatctactgg gcatccacta gggaatctgg     300
ggtccctgat cgcttctcag gcagtggatc tgggacagat ttcactctca ccatcagcag     360
agtggaggct gaagacgtgg gagtttatta ctgcaagcaa tcttatgatc ttcggacgtt     420
cggcggaggg accaaggtgg agatcaaacg aactgtggct gcaccatctg tcttcatctt     480
cccgccatct gatgagcagt tgaaatctgg aactgcctct gttgtgtgcc tgctgaataa     540
cttctatccc agagaggcca agtacagtg gaaggtggat aacgccctcc aatcgggtaa     600
ctcccaggag agtgtcacag agcaggacag caaggacagc acctacagcc tcagcagcac     660
cctgacgctg agcaaagcag actacgagaa acacaaagtc tacgcctgcg aagtcaccca     720
tcagggcctg agctcgcccg tcacaaagag cttcaacagg ggtgagtgtt ag             772

<210> SEQ ID NO 30
<211> LENGTH: 239
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 30

Met Asp Ser Gln Ala Gln Val Leu Ile Leu Leu Leu Leu Trp Val Ser
1               5                   10                  15

Gly Thr Cys Gly Asp Val Val Met Thr Gln Ser Pro Leu Ser Leu Pro
            20                  25                  30

Val Thr Leu Gly Gln Pro Ala Ser Ile Ser Cys Lys Ser Ser Gln Ser
        35                  40                  45

Leu Leu Asn Ser Arg Thr Arg Lys Asn Tyr Leu Ala Trp Phe Gln Gln
    50                  55                  60

Arg Pro Gly Gln Ser Pro Arg Leu Arg Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Arg Val Glu Ala Glu Asp Val Gly Val Tyr
            100                 105                 110

Tyr Cys Lys Gln Ser Tyr Asp Leu Arg Thr Phe Gly Gly Gly Thr Lys
        115                 120                 125

```
Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 31
<211> LENGTH: 1513
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 31

```
taacaacgca gagtacgcgg gggcgtatga acctagccct gatttcccca gccttcagtt    60
cccagattca gtgatcagcc ttgaacacag acctgtcacc atgaagttgt ggctgaactg   120
gattttcctt gtaacacttt taaatggtat ccagtgtcag gtgacgctga aggagtctgg   180
accagtcttg gtaaagccta cggagactct gacactcacc tgtacagttt ctgggttcac   240
cttcactgat tactacatga gctggatccg ccagcctcca ggaaaggcac ttgagtggct   300
ggcttttatt cgaaacaaag ctactggtta cacaacagag tacagtgcat ctgtgaaggg   360
tcggctcacc atctccaaag atacttccaa atcccaggtc gttcttacaa tgaccaacat   420
ggatcctgtg gacactgcca cttattactg tgcaagagat tttggtagta ggtggtactt   480
cgatgtctgg ggccagggaa ccctggtcac cgtctcctca gcctccacca agggcccatc   540
ggtcttcccc ctggcaccct cctccaagag cacctctggg ggcacagcgg ccctgggctg   600
cctggtcaag gactacttcc ccgaaccggt gacggtgtcg tggaactcag gcgccctgac   660
cagcggcgtg cacaccttcc cggctgtcct acagtcctca ggactctact ccctcagcag   720
cgtggtgacc gtgccctcca gcagcttggg cacccagacc tacatctgca acgtgaatca   780
caagcccagc aacaccaagg tggacaagaa agttgagccc aaatcttgtg acaaaactca   840
cacatgccca ccgtgcccag cacctgaact cctggggggg accgtcagtct tcctcttccc   900
cccaaaaccc aaggacaccc tcatgatctc ccggacccct gaggtcacat gcgtggtggt   960
ggacgtgagc cacgaagacc ctgaggtcaa gttcaactgg tacgtggacg gcgtggaggt  1020
gcataatgcc aagacaaagc cgcgggagga gcagtacaac agcacgtacc gtgtggtcag  1080
cgtcctcacc gtcctgcacc aggactggct gaatggcaag gagtacaagt gcaaggtctc  1140
caacaaagcc ctcccagccc ccatcgagaa aaccatctcc aaagccaaag ggcagccccg  1200
agaaccacag gtgtacaccc tgcccccatc ccgggatgag ctgaccaaga accaggtcag  1260
cctgacctgc ctggtcaaag gcttctatcc cagcgacatc gccgtggagt gggagagcaa  1320
tgggcagccg gagaacaact acaagaccac gcctcccgtg ctggactccg acggctcctt  1380
cttcctctat agcaagctca ccgtggacaa gagcaggtgg cagcagggga acgtcttctc  1440
```

```
atgctccgtg atgcatgagg ctctgcacaa ccactacacg cagaagagcc tctccctgtc   1500
tccgggtaaa tga                                                      1513
```

<210> SEQ ID NO 32
<211> LENGTH: 470
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 32

```
Met Lys Leu Trp Leu Asn Trp Ile Phe Leu Val Thr Leu Leu Asn Gly
1               5                   10                  15

Ile Gln Cys Gln Val Thr Leu Lys Glu Ser Gly Pro Val Leu Val Lys
            20                  25                  30

Pro Thr Glu Thr Leu Thr Leu Thr Cys Thr Val Ser Gly Phe Thr Phe
        35                  40                  45

Thr Asp Tyr Tyr Met Ser Trp Ile Arg Gln Pro Pro Gly Lys Ala Leu
    50                  55                  60

Glu Trp Leu Ala Phe Ile Arg Asn Lys Ala Thr Gly Tyr Thr Thr Glu
65                  70                  75                  80

Tyr Ser Ala Ser Val Lys Gly Arg Leu Thr Ile Ser Lys Asp Thr Ser
                85                  90                  95

Lys Ser Gln Val Val Leu Thr Met Thr Asn Met Asp Pro Val Asp Thr
            100                 105                 110

Ala Thr Tyr Tyr Cys Ala Arg Asp Phe Gly Ser Arg Trp Tyr Phe Asp
        115                 120                 125

Val Trp Gly Gln Gly Thr Leu Val Thr Val Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
```

```
                    340                 345                 350
Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 33
<211> LENGTH: 913
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 33
ggccccccct cgaggtcgac ggtatcgata agcttgatat cagcggccgc acaacgcaga      60
gtacgcgggg gactgatcag tctcctcagg ctgtctcctc aggttgcctc ctcaaaatga    120
agttgcctgt taggctgttg gtgctgatgt tctggattcc tgcttccagc agtgaaattg    180
tgatgaccca aactccactc tccctgtcta tcactcctgg agaacaagcc tccatctctt    240
gcagatctag tcagagcctt gtacacagta atggaaacac ctatttacat tggttcctgc    300
agaaggcacg cccggtttca acgctcctga tctacaaagt ttccaaccga ttttctgggg    360
tcccagacag gttcagtggc agtggatcag ggacagattt cacactcaag atcagcagag    420
tggaggctga ggatttcgga gtttattact gctctcaaag tacacatgtt cctccgacgt    480
tcggcggagg gaccaaggtg gagatcaaac gaactgtggc tgcaccatct gtcttcatct    540
tcccgccatc tgatgagcag ttgaaatctg gaactgcctc tgttgtgtgc ctgctgaata    600
acttctatcc cagagaggcc aaagtacagt ggaaggtgga taacgccctc caatcgggta    660
actcccagga gagtgtcaca gagcaggaca gcaaggacag cacctacagc ctcagcagca    720
ccctgacgct gagcaaagca gactacgaga aacacaaagt ctacgcctgc gaagtcaccc    780
atcagggcct gagctcgccc gtcacaaaga gcttcaacag gggtgagtgt tagctcgagt    840
gatatcgaat tcctgcagcc cggggatcc actagttcta gagcggccgc caccgcgagt    900
ggagctccaa ttc                                                        913

<210> SEQ ID NO 34
<211> LENGTH: 238
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 34
```

```
Met Lys Leu Pro Val Arg Leu Leu Val Leu Met Phe Trp Ile Pro Ala
1               5                   10                  15

Ser Ser Ser Glu Ile Val Met Thr Gln Thr Pro Leu Ser Leu Ser Ile
            20                  25                  30

Thr Pro Gly Glu Gln Ala Ser Ile Ser Cys Arg Ser Ser Gln Ser Leu
        35                  40                  45

Val His Ser Asn Gly Asn Thr Tyr Leu His Trp Phe Leu Gln Lys Ala
50                  55                  60

Arg Pro Val Ser Thr Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Phe Gly Val Tyr Tyr Cys
            100                 105                 110

Ser Gln Ser Thr His Val Pro Pro Thr Phe Gly Gly Gly Thr Lys Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 35
<211> LENGTH: 1517
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 35
tagtaacggc cgccagtgtg ctggaattct gcagatgtaa caacgcagag tacgcgggga      60
catcgctctc actggaggct gatctctgaa gataaggagg tgtagcctaa aagatgagag     120
tgctgattct tttgtggctg ttcacagcct tcctggtat  cctgtctcaa gtgcagcttg     180
tgcagtcggg agctgaagtg aagaaacctg gtgcgtctgt gaaagtcagc tgcaaggcct     240
ctggctactc aatcaccagt gattatgcct ggaactgggt ccggcaggct ccaggacaga     300
gactggagtg gatgggctac ataagctaca gtggtagcac tatctacaac ccatctctca     360
aaagtcgagt cactatcact agagacacat ccgcgagcac ggcctacatg gagttgagtt     420
ctctgagatc tgaggacatg gccgtatatt actgtgcaag atttggtaac tacgaaata     480 ctttgaacta ctggggccag ggaaccctgg tcaccgtctc ctcagcctcc accaagggcc     540
catcggtctt ccccctggca ccctcctcca agagcacctc tgggggcaca gcggccctgg     600
gctgcctggt caaggactac ttccccgaac cggtgacggt gtcgtggaac tcaggcgccc     660
tgaccagcgg cgtgcacacc ttcccggctg tcctacagtc ctcaggactc tactccctca     720
```

-continued

```
gcagcgtggt gaccgtgccc tccagcagct tgggcaccca gacctacatc tgcaacgtga        780
atcacaagcc cagcaacacc aaggtggaca agaaagttga gcccaaatct tgtgacaaaa        840
ctcacacatg cccaccgtgc ccagcacctg aactcctggg gggaccgtca gtcttcctct        900
tccccccaaa acccaaggac accctcatga tctcccggac ccctgaggtc acatgcgtgg        960
tggtggacgt gagccacgaa gaccctgagg tcaagttcaa ctggtacgtg gacggcgtgg       1020
aggtgcataa tgccaagaca aagccgcggg aggagcagta caacagcacg taccgtgtgg       1080
tcagcgtcct caccgtcctg caccaggact ggctgaatgg caaggagtac aagtgcaagg       1140
tctccaacaa agccctccca gcccccatcg agaaaaccat ctccaaagcc aaagggcagc       1200
cccgagaacc acaggtgtac accctgcccc catcccggga tgagctgacc aagaaccagg       1260
tcagcctgac ctgcctggtc aaaggcttct atcccagcga catcgccgtg gagtgggaga       1320
gcaatgggca gccggagaac aactacaaga ccacgcctcc cgtgctggac tccgacggct       1380
ccttcttcct ctatagcaag ctcaccgtgg acaagagcag gtggcagcag gggaacgtct       1440
tctcatgctc cgtgatgcat gaggctctgc acaaccacta cacgcagaag agcctctccc       1500
tgtctccggg taaatga                                                     1517
```

<210> SEQ ID NO 36
<211> LENGTH: 467
<212> TYPE: PRT
<213> ORGANISM: Artificial Sequence
<220> FEATURE:
<223> OTHER INFORMATION: Description of Artificial Sequence: Synthetic construct

<400> SEQUENCE: 36

```
Met Arg Val Leu Ile Leu Leu Trp Leu Phe Thr Ala Phe Pro Gly Ile
1               5                   10                  15

Leu Ser Gln Val Gln Leu Val Gln Ser Gly Ala Glu Val Lys Lys Pro
                20                  25                  30

Gly Ala Ser Val Lys Val Ser Cys Lys Ala Ser Gly Tyr Ser Ile Thr
            35                  40                  45

Ser Asp Tyr Ala Trp Asn Trp Val Arg Gln Ala Pro Gly Gln Arg Leu
        50                  55                  60

Glu Trp Met Gly Tyr Ile Ser Tyr Ser Gly Ser Thr Ile Tyr Asn Pro
65                  70                  75                  80

Ser Leu Lys Ser Arg Val Thr Ile Thr Arg Asp Thr Ser Ala Ser Thr
                85                  90                  95

Ala Tyr Met Glu Leu Ser Ser Leu Arg Ser Glu Asp Met Ala Val Tyr
                100                 105                 110

Tyr Cys Ala Arg Phe Gly Asn Tyr Gly Asn Thr Leu Asn Tyr Trp Gly
            115                 120                 125

Gln Gly Thr Leu Val Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220
```

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 37
<211> LENGTH: 895
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 37
ggccgctcta gaactagtgg atcccccggg ctgcaggaat tcgatatcag cggccgcaca      60
acgcagagta cgcgggggac tgatcagtct cctcaggctg tctcctcagg ttgcctcctc     120
aaaatgaagt tgcctgttag ctgttggtg ctgatgttct ggattcctgc ttccagcagt     180
gatattgtga tgacccaaac tccactctcc ctgcctgtca ctcctggaga accagcctcc     240
atctcttgca gatctagtca gagccttgta cacagtaatg aaacaccta tttacattgg     300 tacctgcaga agccaggcca gtctccacag ctcctgatct acaaagtttc caaccgattt     360
tctggggtcc cagacaggtt cagtggcagt ggatcaggga cagatttcac actcaagatc     420
agcagagtgg aggctgagga tgtgggagtt tattactgct ctcaaagtac acatgttcct     480
ccgacgttcg gcgagggac caaggtggag atcaaacgaa ctgtggctgc accatctgtc     540
ttcatcttcc cgccatctga tgagcagttg aaatctggaa ctgcctctgt tgtgtgcctg     600

```
ctgaataact tctatcccag agaggccaaa gtacagtgga aggtggataa cgccctccaa    660
tcgggtaact cccaggagag tgtcacagag caggacagca aggacagcac ctacagcctc    720
agcagcaccc tgacgctgag caaagcagac tacgagaaac acaaagtcta cgcctgcgaa    780
gtcacccatc agggcctgag ctcgcccgtc acaaagagct caacaggggg tgagtgttag    840
ctcgagtgaa tcaagcttat cgataccgtc gacctcgagg ggggccccgg taccc          895
```

<210> SEQ ID NO 38
<211> LENGTH: 238
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 38

```
Met Lys Leu Pro Val Arg Leu Leu Val Leu Met Phe Trp Ile Pro Ala
1               5                  10                  15

Ser Ser Ser Asp Ile Val Met Thr Gln Thr Pro Leu Ser Leu Pro Val
            20                  25                  30

Thr Pro Gly Glu Pro Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Gln Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Ser Gln Ser Thr His Val Pro Pro Thr Phe Gly Gly Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 39
<211> LENGTH: 1587
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 39

```
ttggagctcc ccgcggtggc ggtcgctcta gaactttgga tccccgggc tgcaggaatt     60 cgatatcaaa gctaacaacg cagagtacgc ggggacatcg ctctcactgg aggctgatct    120
```

```
ctgaagataa ggaggtgtag cctaaaagat gagagtgctg attcttttgt ggctgttcac      180
agcctttcct ggtatcctgt ctcaagtgca gcttcaggag tcgggacctg gcctggtgaa      240
accttctcag actctgtccc tcacctgcac tgtctctggc tactcaatca ccagtgatta      300
tgcctggaac tggatccggc agcatccagg aaagggactg gagtggatcg gctacataag      360
ctacagtggt agcactatct acaacccatc tctcaaaagt cgagtcacta tcagtgtaga      420
cacatccaag aaccagttct ccctgaagtt gagttctgtg actgctgcgg acacagccgt      480
atattactgt gcaagatttg gtaactacgg aaatactttg aactactggg gccagggaac      540
cctggtcacc gtctcctcag cctccaccaa gggcccatcg gtcttccccc tggcaccctc      600
ctccaagagc acctctgggg gcacagcggc cctgggctgc ctggtcaagg actacttccc      660
cgaaccggtg acggtgtcgt ggaactcagg cgccctgacc agcggcgtgc acaccttccc      720
ggctgtccta cagtcctcag gactctactc cctcagcagc gtggtgaccg tgccctccag      780
cagcttgggc acccagacct acatctgcaa cgtgaatcac aagcccagca acaccaaggt      840
ggacaagaaa gttgagccca aatcttgtga caaaactcac acatgcccac cgtgcccagc      900
acctgaactc ctggggggac cgtcagtctt cctcttcccc ccaaaaccca aggacaccct      960
catgatctcc cggacccctg aggtcacatg cgtggtggtg gacgtgagcc acgaagaccc     1020
tgaggtcaag ttcaactggt acgtggacgg cgtggaggtg cataatgcca agacaaagcc     1080
gcgggaggag cagtacaaca gcacgtaccg tgtggtcagc gtcctcaccg tcctgcacca     1140
ggactggctg aatggcaagg agtacaagtg caaggtctcc aacaaagccc tcccagcccc     1200
catcgagaaa accatctcca aagccaaagg gcagccccga gaaccacagg tgtacaccct     1260
gcccccatcc cgggatgagc tgaccaagaa ccaggtcagc ctgacctgcc tggtcaaagg     1320
cttctatccc agcgacatcg ccgtggagtg ggagagcaat gggcagccgg agaacaacta     1380
caagaccacg cctcccgtgc tggactccga cggctccttc ttcctctata gcaagctcac     1440
cgtggacaag agcaggtggc agcaggggaa cgtcttctca tgctccgtga tgcatgaggc     1500
tctgcacaac cactacacgc agaagagcct ctccctgtct ccgggtaaat gatctagatg     1560
atatcaagct tatcgatacc gtcgacc                                         1587
```

<210> SEQ ID NO 40
<211> LENGTH: 467
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 40

```
Met Arg Val Leu Ile Leu Leu Trp Leu Phe Thr Ala Phe Pro Gly Ile
1               5                   10                  15

Leu Ser Gln Val Gln Leu Gln Glu Ser Gly Pro Gly Leu Val Lys Pro
            20                  25                  30

Ser Gln Thr Leu Ser Leu Thr Cys Thr Val Ser Gly Tyr Ser Ile Thr
        35                  40                  45

Ser Asp Tyr Ala Trp Asn Trp Ile Arg Gln His Pro Gly Lys Gly Leu
    50                  55                  60

Glu Trp Ile Gly Tyr Ile Ser Tyr Ser Gly Ser Thr Ile Tyr Asn Pro
65                  70                  75                  80

Ser Leu Lys Ser Arg Val Thr Ile Ser Val Asp Thr Ser Lys Asn Gln
                85                  90                  95
```

```
Phe Ser Leu Lys Leu Ser Ser Val Thr Ala Asp Thr Ala Val Tyr
                100                 105                 110
Tyr Cys Ala Arg Phe Gly Asn Tyr Gly Asn Thr Leu Asn Tyr Trp Gly
            115                 120                 125
Gln Gly Thr Leu Val Thr Val Ser Ser Ala Ser Thr Lys Gly Pro Ser
130                 135                 140
Val Phe Pro Leu Ala Pro Ser Ser Lys Ser Thr Ser Gly Gly Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Ser Leu Gly Thr Gln Thr Tyr Ile Cys Asn Val Asn His
    210                 215                 220
Lys Pro Ser Asn Thr Lys Val Asp Lys Lys Val Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 41
<211> LENGTH: 384
<212> TYPE: DNA
<213> ORGANISM: Mus musculus

<400> SEQUENCE: 41
```

```
atggacatga gggcccctgc tcagttttt gggatcttgt tgctctggtt tccaggtatc      60
agatgtgaca tcaagatgac ccagtctcca tcctccatgt atgcatcgct gggagagaga    120
gtcactatca cttgcaaggc gagtcaggac attaaaagct atttaagctg gtaccagcag    180
aaaccatgga atctcctaa gattttgatc tattatgcaa caagcttggc agatggggtc    240
ccatcaagaa tcagtggcag tggatctggg caagattatt ctctaaccat cagcagcctg    300
gagtctgacg atacagcaac ttattactgt ctacagcatg gtgagagccc gtacacgttc    360
ggagggggga ccaagctgga aata                                            384

<210> SEQ ID NO 42
<211> LENGTH: 399
<212> TYPE: DNA
<213> ORGANISM: Mus musculus

<400> SEQUENCE: 42
atgaacttcg ggttcagctt gattttcctt gtccttgttt taaaaggtgt ccagtgtgaa     60
gtgaagctgg tggagtctgg gggaggctta gtgaagcctg gagggtccct gaaactctcc    120
tgtgcagcct ctggattcac tttcagtaac atgccatgt cttgggttcg ccagactcca    180
gagaagaggc tggagtgggt cgcctccatt agtagtgatg gtgacaccta ctttccagac    240
aatgtgaagg gccgattcac catctccaga gaaaatgccg ggaacatcct gttcctgcaa    300
atgagcagtc tgaggtctga ggacacggcc atgtattact gtgcaagagg atttatgatt    360
acgttctggg gccaagggac tctggtcact gtctctgca                           399

<210> SEQ ID NO 43
<211> LENGTH: 236
<212> TYPE: PRT
<213> ORGANISM: Mus musculus

<400> SEQUENCE: 43

Met Asp Met Arg Ala Pro Ala Gln Phe Phe Gly Ile Leu Leu Leu Trp
1               5                  10                  15

Phe Pro Gly Ile Arg Cys Asp Ile Lys Met Thr Gln Ser Pro Ser Ser
            20                  25                  30

Met Tyr Ala Ser Leu Gly Glu Arg Val Thr Ile Thr Cys Lys Ala Ser
        35                  40                  45

Gln Asp Ile Lys Ser Tyr Leu Ser Trp Tyr Gln Gln Lys Pro Trp Lys
    50                  55                  60

Ser Pro Lys Ile Leu Ile Tyr Tyr Ala Thr Ser Leu Ala Asp Gly Val
65                  70                  75                  80

Pro Ser Arg Ile Ser Gly Ser Gly Ser Gly Gln Asp Tyr Ser Leu Thr
                85                  90                  95

Ile Ser Ser Leu Glu Ser Asp Asp Thr Ala Thr Tyr Tyr Cys Leu Gln
            100                 105                 110

His Gly Glu Ser Pro Tyr Thr Phe Gly Gly Gly Thr Lys Leu Glu Ile
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190
```

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235

<210> SEQ ID NO 44
<211> LENGTH: 227
<212> TYPE: PRT
<213> ORGANISM: Mus musculus

<400> SEQUENCE: 44

Met Asn Phe Gly Phe Ser Leu Ile Phe Leu Val Leu Val Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asn Tyr Ala Met Ser Trp Val Arg Gln Thr Pro Glu Lys Arg Leu
    50                  55                  60

Glu Trp Val Ala Ser Ile Ser Ser Asp Gly Asp Thr Tyr Phe Pro Asp
65                  70                  75                  80

Asn Val Lys Gly Arg Phe Thr Ile Ser Arg Glu Asn Ala Gly Asn Ile
                85                  90                  95

Leu Phe Leu Gln Met Ser Ser Leu Arg Ser Glu Asp Thr Ala Met Tyr
            100                 105                 110

Tyr Cys Ala Arg Gly Phe Met Ile Thr Phe Trp Gly Gln Gly Thr Leu
        115                 120                 125

Val Thr Val Ser Ala Ala Lys Thr Thr Pro Pro Ser Val Tyr Pro Leu
    130                 135                 140

Ala Pro Gly Cys Gly Asp Thr Thr Gly Ser Ser Val Thr Leu Gly Cys
145                 150                 155                 160

Leu Val Lys Gly Tyr Phe Pro Glu Ser Val Thr Val Thr Trp Asn Ser
                165                 170                 175

Gly Ser Leu Ser Ser Ser Val His Thr Phe Pro Ala Leu Leu Gln Ser
            180                 185                 190

Gly Leu Tyr Thr Met Ser Ser Ser Val Thr Val Pro Ser Ser Thr Trp
        195                 200                 205

Pro Ser Gln Thr Val Thr Cys Ser Val Ala His Pro Ala Ser Ser Thr
    210                 215                 220

Thr Val Asp
225

<210> SEQ ID NO 45
<211> LENGTH: 399
<212> TYPE: DNA
<213> ORGANISM: Mus musculus

<400> SEQUENCE: 45
atggattcac aggcccaggt tcttatattg ctgctgctat gggtatctgg tacctgtggg     60
gacattgtga tgtcacagtc tccatcctcc ctggctgtgt cagcaggaga gaaggtcact    120
atgagctgca atccagtca gagtctgctc aacagtagaa cccgaaagaa ctacttggct    180
tggtatcagc agaaaccagg gcagtctcct aaactgctga tctactgggc atccactagg    240
gaatctgggg tccctgatcg cttcacaggc agtggatctg ggacagattt cactctcacc    300

```
atcagcagtg tgcaggctga agacctggca gtttattact gcaagcaatc ttatgatctt    360
cggacgttcg gtggaggcac caagctggaa atcaaacgg                           399

<210> SEQ ID NO 46
<211> LENGTH: 420
<212> TYPE: DNA
<213> ORGANISM: Mus musculus

<400> SEQUENCE: 46
atgaagttgt ggctgaactg gattttcctt gtaacacttt taaatggtat ccagtgtgag     60
gtgaagctgg tggagtctgg aggaggcttg gtacagcctg ggggttctct gagactctcc    120
tgtgcaactt ctgggttcac cttcactgat tactacatga gctgggtccg ccagcctcca    180
ggaaaggcac ttgagtggtt gggttttatt agaaacaaag ctactggtta cacaacagag    240
tacagtgcat ctgtgaaggg tcggttcacc atctccagag ataattccca aagcatcctc    300
tatcttcaaa tgaacaccct gagagctgag gacagtgcca cttattactg tgcaagagat    360
acggcggcta cgtggtactt cgatgtctgg ggcgcaggga ccacggtcac cgtctcctca    420

<210> SEQ ID NO 47
<211> LENGTH: 239
<212> TYPE: PRT
<213> ORGANISM: Mus musculus

<400> SEQUENCE: 47
```

Met Asp Ser Gln Ala Gln Val Leu Ile Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asp Leu Arg Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

```
<210> SEQ ID NO 48
<211> LENGTH: 177
<212> TYPE: PRT
<213> ORGANISM: Mus musculus

<400> SEQUENCE: 48

Met Lys Leu Trp Leu Asn Trp Ile Phe Leu Val Thr Leu Leu Asn Gly
1               5                   10                  15

Ile Gln Cys Glu Val Lys Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

Thr Asp Tyr Tyr Met Ser Trp Val Arg Gln Pro Pro Gly Lys Ala Leu
    50                  55                  60

Glu Trp Leu Gly Phe Ile Arg Asn Lys Ala Thr Gly Tyr Thr Thr Glu
65                  70                  75                  80

Tyr Ser Ala Ser Val Lys Gly Arg Phe Thr Ile Ser Arg Asp Asn Ser
                85                  90                  95

Gln Ser Ile Leu Tyr Leu Gln Met Asn Thr Leu Arg Ala Glu Asp Ser
            100                 105                 110

Ala Thr Tyr Tyr Cys Ala Arg Asp Thr Ala Ala Thr Trp Tyr Phe Asp
        115                 120                 125

Val Trp Gly Ala Gly Thr Thr Val Thr Val Ser Ser Ala Lys Thr Thr
    130                 135                 140

Pro Pro Ser Val Tyr Pro Leu Ala Pro Gly Cys Gly Asp Thr Thr Gly
145                 150                 155                 160

Ser Ser Val Thr Leu Gly Cys Leu Gly Gln Gly Ala Thr Ser Leu Ser
                165                 170                 175

Gln

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtaacaacgc agagtacgcg gg                                          22

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tcatttaccc ggagaccgg                                              19

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ctaacactca ttcctgttga agctc                                       25
```

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
tcatttaccc ggagacaggg agaggc                                    26

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
cgtccgaaga tcataagatt gcttgc                                    26

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
ctaacactca ccccbgttga ag                                        22

<210> SEQ ID NO 55
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
gcaatcttat gatcttcgga cgttcggcgg agggaccaag gtg                 43

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
acaacgcaga gtacgcggg                                            19

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
atcagcggcc gcacaacgca gagtacgcgg g                              31

<210> SEQ ID NO 58
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
atcactcgag ctaacactca cccctgttga ag        32

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
gacatcgaag taccacctac tacc        24

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
tcatttaccc ggagacaggg agaggc        26

<210> SEQ ID NO 61
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
ggtagtaggt ggtacttcga tgtctggggc cagggaaccc tggtcacc        48

<210> SEQ ID NO 62
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
atcaaagctt acaacgcaga gtacgcgggg gcgtatg        37

<210> SEQ ID NO 63
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
atcatctaga tcatttaccc ggagacaggg agaggctctt c        41

<210> SEQ ID NO 64
<211> LENGTH: 29

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cgtcggagga acatgtgtac tttgagagc                                     29

<210> SEQ ID NO 65
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
caaagtacac atgttcctcc gacgttcggc ggagggacca aggtg                   45

<210> SEQ ID NO 66
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
atcagcggcc gcacaacgca gagtacgcgg g                                  31

<210> SEQ ID NO 67
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
atcactcgag ctaacactca ccctgttga ag                                  32

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gtagttcaaa gtatttccgt agttacc                                       27

<210> SEQ ID NO 69
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ggtaactacg gaaatacttt gaactactgg ggccagggaa ccctggtcac c             51

<210> SEQ ID NO 70
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 70
aaagcttaca acgcagagta cgcgggg                                          27

<210> SEQ ID NO 71
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
atctagatca tttacccgga gacagggaga g                                     31

<210> SEQ ID NO 72
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ggggacattg tgatgacaca gtctccagac tccctggctg tgtcag                     46

<210> SEQ ID NO 73
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gtgtcagcag gagagagggc cactataaac tgcaaatcca gtcag                      45

<210> SEQ ID NO 74
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gacattgtga tgtcacagcc tccatcctcc ctggctgtg                             39

<210> SEQ ID NO 75
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ggggtccctg atcgcttctc aggcagtgga tctgggaca                             39

<210> SEQ ID NO 76
<211> LENGTH: 48
<212> TYPE: DNA
<213> ORGANISM: Artificial Sequence
<220> FEATURE:
<223> OTHER INFORMATION: Description of Artificial Sequence: Synthetic
```

```
                                    primer

<400> SEQUENCE: 76
ctcaccatca gcagtctgca ggctgaagac gtggcagttt attactgc                       48

<210> SEQ ID NO 77
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
agactccctg gctgtgtcac taggagagag ggccactata aactgc                         46

<210> SEQ ID NO 78
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
accagcagaa accagggcag cctcctaaac tgctgatcta c                              41

<210> SEQ ID NO 79
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
caccatctcc agagatgatt ccaaaaacag cctctatctt caaatgaac                      49

<210> SEQ ID NO 80
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ggtatccagt gtgaggtgca gctggtggag tctggagga                                 39

<210> SEQ ID NO 81
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ctgagactct cctgtgcagc ttctgggttc accttcact                                 39

<210> SEQ ID NO 82
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 82
cgccagcctc caggaaaggg acttgagtgg gtgggtttta ttagaaac                48

<210> SEQ ID NO 83
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tatcttcaaa tgaacagcct gaaaactgag gacagtgcca cttattactg              50

<210> SEQ ID NO 84
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
acatgagctg ggtccgccag gctccaggaa agggacttga g                       41

<210> SEQ ID NO 85
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cctgaaaact gaggacactg ccgtttatta ctgtgcaaga gatttcg                 47

<210> SEQ ID NO 86
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gtgatgttgt gatgacccaa agtccactct ccctgcctgt cag                     43

<210> SEQ ID NO 87
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ctctccctgc ctgtcactct tggacaacca gcctccatct cttgc                   45

<210> SEQ ID NO 88
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
aagccaggcc agtctccaag gcgcctgatc tacaaagttt cc        42

<210> SEQ ID NO 89
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ggaggctgag gatgtgggag tttattactg ctctcaaagt acac        44

<210> SEQ ID NO 90
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
acacctattt acattggttc cagcagaggc caggccagtc tccaaggc        48

<210> SEQ ID NO 91
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gagtggaggc tgaggatgtg ggagtttatt actgctctca aagtacacat g        51

<210> SEQ ID NO 92
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
catctctcaa aagtcgagtc tctatcagtg tagacacatc caagaacc        48

<210> SEQ ID NO 93
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gcctggtgaa accttctgag actctgtccc tcacctgcac        40

<210> SEQ ID NO 94
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
aactggatcc ggcagcctcc aggaaaagga ctggagtgga tgggc        45

<210> SEQ ID NO 95
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
tccaagaacc agttctccct gaagttgagt tctgtgacta ctgag          45

<210> SEQ ID NO 96
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ggaactggat ccggcagcct ccaggaaagg gactggagtg gatgggctac          50

<210> SEQ ID NO 97
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gttgagttct gtgactgctg cggacacagc cgtatattac tgtgcaagat ttgg          54

<210> SEQ ID NO 98
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tccctcacct gcactgtctc tggctactca atc          33

<210> SEQ ID NO 99
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
acaaactgga gtggatcggc tacataagct acag          34

<210> SEQ ID NO 100
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
tcaaaagtcg agtcactatc agtgtagaca catccaag          38

<210> SEQ ID NO 101

```
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gacacagtct ccactctccc tgcctgtgac actaggagag agggccac                    48

<210> SEQ ID NO 102
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ctctcaccat cagcagagtg gaggctgaag acgtggc                               37

<210> SEQ ID NO 103
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
aggctgaaga cgtgggagtt tattactgca agc                                   33

<210> SEQ ID NO 104
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
cagaaaccag ggcagtctcc tcaactgctg atctactggg c                          41

<210> SEQ ID NO 105
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
cttggcttgg tacctgcaga aaccagggc                                        29

<210> SEQ ID NO 106
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gacaccagga gagccggcct ctataagctg caaatccagt c                          41

<210> SEQ ID NO 107
<211> LENGTH: 29
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 107
cttggcttgg tacctgcaga aaccagggc                                     29

<210> SEQ ID NO 108
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ggacagattt cactctcaaa atcagcagag tggaggctg                          39

<210> SEQ ID NO 109
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
tgtgaggtgc agctgttgga gtctggagga ggc                                33

<210> SEQ ID NO 110
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gacttgagtg ggtgagtttt attagaaaca aagc                               34

<210> SEQ ID NO 111
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
catctccaga gataattcca aaaacaccct ctatcttcaa atg                     43

<210> SEQ ID NO 112
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
aatgaacagc ctgagagctg aggacactgc cg                                 32

<210> SEQ ID NO 113
<211> LENGTH: 33
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 113
gtttattact gtgcaaagga ttttggtagt agg                                          33

<210> SEQ ID NO 114
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
acctgtgggg acgttgtgat gacacagtct cc                                           32

<210> SEQ ID NO 115
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gacacagtct ccactctccc tgcctgtgac actaggagag agggccac                          48

<210> SEQ ID NO 116
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
ctacttggct tggttccagc agagaccagg gcagcctcc                                    39

<210> SEQ ID NO 117
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ctctcaccat cagcagagtg gaggctgaag acgtggc                                      37

<210> SEQ ID NO 118
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
aggctgaaga cgtgggagtt tattactgca agc                                          33

<210> SEQ ID NO 119
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
ctgtgacact aggacagccg gcctctataa gctgcaaatc cagtcagag        49

<210> SEQ ID NO 120
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
agaccagggc agtctcctag actgcggatc tactgggcat cc        42

<210> SEQ ID NO 121
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
cagatttcac tctcaaaatc agcagagtgg aggc        34

<210> SEQ ID NO 122
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
aatggtatcc agtgtcaggt gacgctgaag gagtctggag gaggc        45

<210> SEQ ID NO 123
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gaccagtctt ggtaaagcct acggagactc tgagactctc ctg        43

<210> SEQ ID NO 124
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ctacggagac tctgacactc acctgtacag tttctgggtt caccttc        47

<210> SEQ ID NO 125
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
tacatgagct ggatccgcca gcctccagga aagggacttg                            40

<210> SEQ ID NO 126
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gcctccagga aaggcacttg agtggctggc ttttattaga aacaaagc                  48

<210> SEQ ID NO 127
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tgtgaagggt cggctcacca tctccaaaga tacttccaaa aacagcctc                 49

<210> SEQ ID NO 128
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
cgttcttaca atgaccaaca tggatcctgt ggacactgcc gtttattac                 49

<210> SEQ ID NO 129
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
gtggacactg ccacttatta ctgtgcaag                                       29

<210> SEQ ID NO 130
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
caaagatact tccaaatccc aggt                                            24

<210> SEQ ID NO 131
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
ctggaccagt cttggtaaag cctacggaga ctctgagact ctcctg                    46

<210> SEQ ID NO 132
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cctgcttcca gcagtgaaat tgtgatgacc caaagtcc                           38

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gtccactctc cctgtctatc actc                                          24

<210> SEQ ID NO 134
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
tatttacatt ggttcctgca gaaggcaggc cagtctccaa ggc                     43

<210> SEQ ID NO 135
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
gtggaggctg aggatttcgg agtttattac tgc                                33

<210> SEQ ID NO 136
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
attgtgatga cccaaactcc actctccctg tc                                 32

<210> SEQ ID NO 137
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
tctatcactc ctggagaaca agcctccatc tcttgc                             36

```
<210> SEQ ID NO 138
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ttcctgcaga aggcacgccc ggttccaagg cgcctgatc                              39

<210> SEQ ID NO 139
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
ccacgcccgg tttcaacgct cctgatctac aaagtttcc                              39

<210> SEQ ID NO 140
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
ggtatcctgt ctcaagtgca gcttcagg                                          28

<210> SEQ ID NO 141
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
tcaagtgcag cttgtgcagt cgggacctgg cctgg                                  35

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
cttgtgcagt cgggagctga a                                                 21

<210> SEQ ID NO 143
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gcgtctgtga aagtcagctg caaggcctct ggctactcaa tc                          42

<210> SEQ ID NO 144
<211> LENGTH: 37
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
gcctggaact gggtccggca ggctccagga cagagac                              37

<210> SEQ ID NO 145
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gcagcctcca ggacagagac tggagtggat cg                                   32

<210> SEQ ID NO 146
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
agagactgga gtggatgggc tacataagct ac                                   32

<210> SEQ ID NO 147
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
gtcgagtcac tatcactaga gacacatcca agaacc                               36

<210> SEQ ID NO 148
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
atcactagag acacatccgc gagcacggcc tacatggagt tgag                      44

<210> SEQ ID NO 149
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
aagaaccagt tctacatgga gttgagttct ctg                                  33

<210> SEQ ID NO 150
<211> LENGTH: 41
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 150
gaagttgagt tctctgagat ctgaggacac agccgtatat t                41

<210> SEQ ID NO 151
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
tgagatctga ggacatggcc gtatattact g                           31

<210> SEQ ID NO 152
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
ctggcctggt gaaacctggt gcgtctgtga aactcacctg cactgtctct g      51

<210> SEQ ID NO 153
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
cttccagcag tgatattgtg atgacccaaa ctccactctc cctgcc           46

<210> SEQ ID NO 154
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
ctgcctgtca ctcctggaga accagcctcc atctcttgc                   39

<210> SEQ ID NO 155
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
cctatttaca ttggtacctg cagaagccag gccagtctcc                  40

<210> SEQ ID NO 156
<211> LENGTH: 38
<212> TYPE: DNA
<213> ORGANISM: Artificial Sequence
<220> FEATURE:
<223> OTHER INFORMATION: Description of Artificial Sequence: Synthetic

```
                                  primer

<400> SEQUENCE: 156
caggccagtc tccacagctc ctgatctaca aagtttcc                          38

<210> SEQ ID NO 157
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
ggtatcctgt ctcaagtgca gcttcagg                                     28

<210> SEQ ID NO 158
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gtgaaacctt ctcagactct gtccctc                                      27

<210> SEQ ID NO 159
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
tggatccggc agcatccagg aaaggg                                       26

<210> SEQ ID NO 160
<211> LENGTH: 11
<212> TYPE: PRT
<213> ORGANISM: Mus musculus

<400> SEQUENCE: 160

Lys Ala Ser Gln Asp Ile Lys Ser Tyr Leu Ser
1               5                   10

<210> SEQ ID NO 161
<211> LENGTH: 7
<212> TYPE: PRT
<213> ORGANISM: Mus musculus

<400> SEQUENCE: 161

Tyr Ala Thr Ser Leu Ala Asp
1               5

<210> SEQ ID NO 162
<211> LENGTH: 9
<212> TYPE: PRT
<213> ORGANISM: Mus musculus

<400> SEQUENCE: 162

Leu Gln His Gly Glu Ser Pro Tyr Thr
1               5

<210> SEQ ID NO 163
```

```
<211> LENGTH: 10
<212> TYPE: PRT
<213> ORGANISM: Mus musculus

<400> SEQUENCE: 163

Gly Phe Thr Phe Ser Asn Tyr Ala Met Ser
1               5                   10

<210> SEQ ID NO 164
<211> LENGTH: 16
<212> TYPE: PRT
<213> ORGANISM: Mus musculus

<400> SEQUENCE: 164

Ser Ile Ser Ser Asp Gly Asp Thr Tyr Phe Pro Asp Asn Val Lys Gly
1               5                   10                  15

<210> SEQ ID NO 165
<211> LENGTH: 6
<212> TYPE: PRT
<213> ORGANISM: Mus musculus

<400> SEQUENCE: 165

Gly Phe Met Ile Thr Phe
1               5

<210> SEQ ID NO 166
<211> LENGTH: 17
<212> TYPE: PRT
<213> ORGANISM: Mus musculus

<400> SEQUENCE: 166

Lys Ser Ser Gln Ser Leu Leu Asn Ser Arg Thr Arg Lys Asn Tyr Leu
1               5                   10                  15

Ala

<210> SEQ ID NO 167
<211> LENGTH: 7
<212> TYPE: PRT
<213> ORGANISM: Mus musculus

<400> SEQUENCE: 167

Trp Ala Ser Thr Arg Glu Ser
1               5

<210> SEQ ID NO 168
<211> LENGTH: 8
<212> TYPE: PRT
<213> ORGANISM: Mus musculus

<400> SEQUENCE: 168

Lys Gln Ser Tyr Asp Leu Arg Thr
1               5

<210> SEQ ID NO 169
<211> LENGTH: 10
<212> TYPE: PRT
<213> ORGANISM: Mus musculus

<400> SEQUENCE: 169

Gly Phe Thr Phe Thr Asp Tyr Tyr Met Ser
1               5                   10

<210> SEQ ID NO 170
<211> LENGTH: 19
```

```
<212> TYPE: PRT
<213> ORGANISM: Mus musculus

<400> SEQUENCE: 170

Phe Ile Arg Asn Lys Ala Thr Gly Tyr Thr Thr Glu Tyr Ser Ala Ser
1               5                   10                  15

Val Lys Gly

<210> SEQ ID NO 171
<211> LENGTH: 10
<212> TYPE: PRT
<213> ORGANISM: Mus musculus

<400> SEQUENCE: 171

Asp Phe Gly Ser Arg Trp Tyr Phe Asp Val
1               5                   10

<210> SEQ ID NO 172
<211> LENGTH: 16
<212> TYPE: PRT
<213> ORGANISM: Mus musculus

<400> SEQUENCE: 172

Arg Ser Ser Gln Ser Leu Val His Ser Asn Gly Asn Thr Tyr Leu His
1               5                   10                  15

<210> SEQ ID NO 173
<211> LENGTH: 7
<212> TYPE: PRT
<213> ORGANISM: Mus musculus

<400> SEQUENCE: 173

Lys Val Ser Asn Arg Phe Ser
1               5

<210> SEQ ID NO 174
<211> LENGTH: 9
<212> TYPE: PRT
<213> ORGANISM: Mus musculus

<400> SEQUENCE: 174

Ser Gln Ser Thr His Val Pro Pro Thr
1               5

<210> SEQ ID NO 175
<211> LENGTH: 11
<212> TYPE: PRT
<213> ORGANISM: Mus musculus

<400> SEQUENCE: 175

Gly Tyr Ser Ile Thr Ser Asp Tyr Ala Trp Asn
1               5                   10

<210> SEQ ID NO 176
<211> LENGTH: 16
<212> TYPE: PRT
<213> ORGANISM: Mus musculus

<400> SEQUENCE: 176

Tyr Ile Ser Tyr Ser Gly Ser Thr Ile Tyr Asn Pro Ser Leu Lys Ser
1               5                   10                  15

<210> SEQ ID NO 177
<211> LENGTH: 10
<212> TYPE: PRT
```

<213> ORGANISM: Mus musculus

<400> SEQUENCE: 177

Phe Gly Asn Tyr Gly Asn Thr Leu Asn Tyr
1               5                   10

<210> SEQ ID NO 178
<211> LENGTH: 17
<212> TYPE: PRT
<213> ORGANISM: Mus musculus

<400> SEQUENCE: 178

Lys Ser Ser Gln Ser Leu Leu Asn Ser Arg Thr Arg Lys Asn Tyr Leu
1               5                   10                  15

Ala

<210> SEQ ID NO 179
<211> LENGTH: 7
<212> TYPE: PRT
<213> ORGANISM: Mus musculus

<400> SEQUENCE: 179

Trp Ala Ser Thr Arg Glu Ser
1               5

<210> SEQ ID NO 180
<211> LENGTH: 8
<212> TYPE: PRT
<213> ORGANISM: Mus musculus

<400> SEQUENCE: 180

Lys Gln Ser Tyr Asp Leu Arg Thr
1               5

<210> SEQ ID NO 181
<211> LENGTH: 10
<212> TYPE: PRT
<213> ORGANISM: Mus musculus

<400> SEQUENCE: 181

Gly Phe Thr Phe Thr Asp Tyr Tyr Met Ser
1               5                   10

<210> SEQ ID NO 182
<211> LENGTH: 19
<212> TYPE: PRT
<213> ORGANISM: Mus musculus

<400> SEQUENCE: 182

Phe Ile Arg Asn Lys Ala Thr Gly Tyr Thr Thr Glu Tyr Ser Ala Ser
1               5                   10                  15

Val Lys Gly

<210> SEQ ID NO 183
<211> LENGTH: 10
<212> TYPE: PRT
<213> ORGANISM: Mus musculus

<400> SEQUENCE: 183

Asp Thr Ala Ala Thr Trp Tyr Phe Asp Val
1               5                   10

<210> SEQ ID NO 184
<211> LENGTH: 13

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Met His His His His His His Ser Ser Gly Met Gly Asp
1               5                   10

<210> SEQ ID NO 185
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

His His His His His Ser Ser Gly Met Gly Asp Tyr Glu
1               5                   10

<210> SEQ ID NO 186
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

His His His Ser Ser Gly Met Gly Asp Tyr Glu Ile Phe
1               5                   10

<210> SEQ ID NO 187
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

His Ser Ser Gly Met Gly Asp Tyr Glu Ile Phe Asp Glu
1               5                   10

<210> SEQ ID NO 188
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ser Gly Met Gly Asp Tyr Glu Ile Phe Asp Glu Asp Thr
1               5                   10

<210> SEQ ID NO 189
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Met Gly Asp Tyr Glu Ile Phe Asp Glu Asp Thr Lys Thr
1               5                   10
```

<210> SEQ ID NO 190
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Asp Tyr Glu Ile Phe Asp Glu Asp Thr Lys Thr Ile Arg
1               5                   10

<210> SEQ ID NO 191
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Glu Ile Phe Asp Glu Asp Thr Lys Thr Ile Arg Asn Asn
1               5                   10

<210> SEQ ID NO 192
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Phe Asp Glu Asp Thr Lys Thr Ile Arg Asn Asn Ser Trp
1               5                   10

<210> SEQ ID NO 193
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Glu Asp Thr Lys Thr Ile Arg Asn Asn Ser Trp Leu Tyr
1               5                   10

<210> SEQ ID NO 194
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Thr Lys Thr Ile Arg Asn Asn Ser Trp Leu Tyr Gln Leu
1               5                   10

<210> SEQ ID NO 195
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 195

Thr Ile Arg Asn Asn Ser Trp Leu Tyr Gln Leu Ala Met
1               5                   10

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Arg Asn Asn Ser Trp Leu Tyr Gln Leu Ala Met Asp Ile
1               5                   10

<210> SEQ ID NO 197
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Asn Ser Trp Leu Tyr Gln Leu Ala Met Asp Ile Gly Thr
1               5                   10

<210> SEQ ID NO 198
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Trp Leu Tyr Gln Leu Ala Met Asp Ile Gly Thr Pro Tyr
1               5                   10

<210> SEQ ID NO 199
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Tyr Gln Leu Ala Met Asp Ile Gly Thr Pro Tyr Gln Phe
1               5                   10

<210> SEQ ID NO 200
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Leu Ala Met Asp Ile Gly Thr Pro Tyr Gln Phe Asn Gly
1               5                   10

<210> SEQ ID NO 201
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 201

Met Asp Ile Gly Thr Pro Tyr Gln Phe Asn Gly Ser Gly
1               5                   10

<210> SEQ ID NO 202
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ile Gly Thr Pro Tyr Gln Phe Asn Gly Ser Gly Ser Gly
1               5                   10

<210> SEQ ID NO 203
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Thr Pro Tyr Gln Phe Asn Gly Ser Gly Ser Gly Lys Trp
1               5                   10

<210> SEQ ID NO 204
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Tyr Gln Phe Asn Gly Ser Gly Ser Gly Lys Trp Glu Gly
1               5                   10

<210> SEQ ID NO 205
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Phe Asn Gly Ser Gly Ser Gly Lys Trp Glu Gly Gly Pro
1               5                   10

<210> SEQ ID NO 206
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Ser Gly Ser Gly Lys Trp Glu Gly Gly Pro Ser Lys
1               5                   10
```

```
<210> SEQ ID NO 207
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gly Ser Gly Lys Trp Glu Gly Gly Pro Ser Lys Asn Ser
1               5                   10

<210> SEQ ID NO 208
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Lys Trp Glu Gly Gly Pro Ser Lys Asn Ser Val Tyr
1               5                   10

<210> SEQ ID NO 209
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Trp Glu Gly Gly Pro Ser Lys Asn Ser Val Tyr Ile Ser
1               5                   10

<210> SEQ ID NO 210
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Gly Pro Ser Lys Asn Ser Val Tyr Ile Ser Ser Leu
1               5                   10

<210> SEQ ID NO 211
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Pro Ser Lys Asn Ser Val Tyr Ile Ser Ser Leu Tyr Phe
1               5                   10

<210> SEQ ID NO 212
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212
```

Lys Asn Ser Val Tyr Ile Ser Ser Leu Tyr Phe Thr Met
1               5                   10

<210> SEQ ID NO 213
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ser Val Tyr Ile Ser Ser Leu Tyr Phe Thr Met Thr Ser
1               5                   10

<210> SEQ ID NO 214
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Tyr Ile Ser Ser Leu Tyr Phe Thr Met Thr Ser Leu Thr
1               5                   10

<210> SEQ ID NO 215
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ser Ser Leu Tyr Phe Thr Met Thr Ser Leu Thr Ser Val
1               5                   10

<210> SEQ ID NO 216
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Leu Tyr Phe Thr Met Thr Ser Leu Thr Ser Val Gly Phe
1               5                   10

<210> SEQ ID NO 217
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Phe Thr Met Thr Ser Leu Thr Ser Val Gly Phe Gly Asn
1               5                   10

<210> SEQ ID NO 218
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 218

Met Thr Ser Leu Thr Ser Val Gly Phe Gly Asn Ile Ala
1               5                   10

<210> SEQ ID NO 219
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ser Leu Thr Ser Val Gly Phe Gly Asn Ile Ala Pro Ser
1               5                   10

<210> SEQ ID NO 220
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Thr Ser Val Gly Phe Gly Asn Ile Ala Pro Ser Thr Asp
1               5                   10

<210> SEQ ID NO 221
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Val Gly Phe Gly Asn Ile Ala Pro Ser Thr Asp Glu Ile
1               5                   10

<210> SEQ ID NO 222
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Phe Gly Asn Ile Ala Pro Ser Thr Asp Ile Glu Lys Ile
1               5                   10

<210> SEQ ID NO 223
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Asn Ile Ala Pro Ser Thr Asp Ile Glu Lys Ile Phe Leu
1               5                   10

<210> SEQ ID NO 224
<211> LENGTH: 13

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ala Pro Ser Thr Asp Ile Glu Lys Ile Phe Leu Glu Ser
1               5                   10

<210> SEQ ID NO 225
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ser Thr Asp Ile Glu Lys Ile Phe Leu Glu Ser Pro Gln
1               5                   10

<210> SEQ ID NO 226
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Asp Ile Glu Lys Ile Phe Leu Glu Ser Pro Lys Asp Arg
1               5                   10

<210> SEQ ID NO 227
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Glu Lys Ile Phe Leu Glu Ser Pro Lys Asp Arg Ser Pro
1               5                   10

<210> SEQ ID NO 228
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ile Phe Leu Glu Ser Pro Lys Asp Arg Ser Pro Ile Leu
1               5                   10

<210> SEQ ID NO 229
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Leu Glu Ser Pro Lys Asp Arg Ser Pro Ile Leu Ala Glu
1               5                   10
```

```
<210> SEQ ID NO 230
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ser Pro Gln Asp Arg Ser Pro Ile Leu Ala Glu Val Lys
1               5                   10

<210> SEQ ID NO 231
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Gln Asp Arg Ser Pro Ile Leu Ala Glu Val Lys His Ser
1               5                   10

<210> SEQ ID NO 232
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Arg Ser Pro Ile Leu Ala Glu Val Lys His Ser Phe Tyr
1               5                   10

<210> SEQ ID NO 233
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Pro Ile Leu Ala Glu Val Lys His Ser Phe Tyr Pro Ile
1               5                   10

<210> SEQ ID NO 234
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Leu Ala Glu Val Lys His Ser Phe Tyr Pro Ile Pro Glu
1               5                   10

<210> SEQ ID NO 235
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 235

Glu Val Lys His Ser Phe Tyr Pro Ile Pro Glu Gln Thr
1               5                   10

<210> SEQ ID NO 236
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Lys His Ser Phe Tyr Pro Ile Pro Glu Gln Thr Leu Gln
1               5                   10

<210> SEQ ID NO 237
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ser Phe Tyr Pro Ile Pro Glu Gln Thr Leu Gln Ala Thr
1               5                   10

<210> SEQ ID NO 238
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Tyr Pro Ile Pro Glu Gln Thr Leu Gln Ala Thr Val Leu
1               5                   10

<210> SEQ ID NO 239
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ile Pro Glu Gln Thr Leu Gln Ala Thr Val Leu Glu Val
1               5                   10

<210> SEQ ID NO 240
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Glu Gln Thr Leu Gln Ala Thr Val Leu Glu Val Arg His
1               5                   10

<210> SEQ ID NO 241
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 241

Thr Leu Gln Ala Thr Val Leu Glu Val Arg His Glu Leu
1               5                   10

<210> SEQ ID NO 242
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gln Ala Thr Val Leu Glu Val Arg His Glu Leu Lys Glu
1               5                   10

<210> SEQ ID NO 243
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Thr Val Leu Glu Val Arg His Glu Leu Lys Glu Asp Ile
1               5                   10

<210> SEQ ID NO 244
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Leu Glu Val Arg His Glu Leu Lys Glu Asp Ile Lys Ala
1               5                   10

<210> SEQ ID NO 245
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Val Arg His Glu Leu Lys Glu Asp Ile Lys Ala Leu Asn
1               5                   10

<210> SEQ ID NO 246
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

His Glu Leu Lys Glu Asp Ile Lys Ala Leu Asn Ala Lys
1               5                   10
```

```
<210> SEQ ID NO 247
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Leu Lys Glu Asp Ile Lys Ala Leu Asn Ala Lys Met Thr
1               5                   10

<210> SEQ ID NO 248
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Glu Asp Ile Lys Ala Leu Asn Ala Lys Met Thr Asn Ile
1               5                   10

<210> SEQ ID NO 249
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ile Lys Ala Leu Asn Ala Lys Met Thr Asn Ile Glu Lys
1               5                   10

<210> SEQ ID NO 250
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Ala Leu Asn Ala Lys Met Thr Asn Ile Glu Lys Gln Leu
1               5                   10

<210> SEQ ID NO 251
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Asn Ala Lys Met Thr Asn Ile Glu Lys Gln Leu Ser Glu
1               5                   10

<210> SEQ ID NO 252
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252
```

Lys Met Thr Asn Ile Glu Lys Gln Leu Ser Glu Ile Leu
1               5                   10

<210> SEQ ID NO 253
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Thr Asn Ile Glu Lys Gln Leu Ser Glu Ile Leu Arg Ile
1               5                   10

<210> SEQ ID NO 254
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ile Glu Lys Gln Leu Ser Glu Ile Leu Arg Ile Leu Thr
1               5                   10

<210> SEQ ID NO 255
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Lys Gln Leu Ser Glu Ile Leu Arg Ile Leu Thr Ser Leu
1               5                   10

<210> SEQ ID NO 256
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Leu Ser Glu Ile Leu Arg Ile Leu Thr Ser Leu Glu His
1               5                   10

<210> SEQ ID NO 257
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Glu Ile Leu Arg Ile Leu Thr Ser Leu Glu His His His
1               5                   10

<210> SEQ ID NO 258
<211> LENGTH: 13
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 258

Leu Arg Ile Leu Thr Ser Leu Glu His His His His His
1               5                   10

<210> SEQ ID NO 259
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Arg Ile Leu Thr Ser Leu Glu His His His His His His
1               5                   10

<210> SEQ ID NO 260
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
tctggaggtg gaggtagtgg gggaggaggt tcagacatca agatgaccca gtctc         55

<210> SEQ ID NO 261
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
ggcctaatcg gcccgtttta tttccagctt ggtc                                34

<210> SEQ ID NO 262
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
cccactacct ccacctccag agcctccccc tcctgcagag acagtgacca gagtc         55

<210> SEQ ID NO 263
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
agtgatgagc actgaacaca ga                                             22

<210> SEQ ID NO 264
<211> LENGTH: 56
<212> TYPE: DNA
<213> ORGANISM: Artificial Sequence
<220> FEATURE:
<223> OTHER INFORMATION: Description of Artificial Sequence: Synthetic

```
                              primer

<400> SEQUENCE: 264
tctggaggtg gaggtagtgg gggaggaggt tcagacattg tgatgtcaca gtctcc          56

<210> SEQ ID NO 265
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
ggcctaatcg gcccgtttga tttccagctt ggtg                                  34

<210> SEQ ID NO 266
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
gacctgtcac catgaagttg tg                                               22

<210> SEQ ID NO 267
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
cccactacct ccacctccag agcctccccc tcctgaggag acggtgaccg tgg             53

<210> SEQ ID NO 268
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Asp Tyr Glu Ile Phe Asp Glu Asp
1               5

<210> SEQ ID NO 269
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gly Ser Gly Lys Trp Glu Gly
1               5

<210> SEQ ID NO 270
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
         peptide

<400> SEQUENCE: 270

Asn Gly Ser Gly Ser Gly Lys Trp Glu Gly Gly
1               5                   10
```

ANTIBODIES DIRECTED TO THE MAMMALIAN EAG1 ION CHANNEL PROTEIN

The present invention relates to a particularly advantageous antibody, antibody fragment or derivative thereof, which specifically binds to/interacts with at least one epitope of the extracellular or intracellular domain of the mammalian EAG1 ion channel and to nucleic acid molecules encoding the same and to vectors comprising said nucleic acid molecules. The invention additionally relates to methods for the preparation of said antibody, antibody fragments or derivatives thereof and to pharmaceutical compositions comprising the same. Furthermore, the use of said antibody, antibody fragment or derivative thereof and also diagnostic compositions comprising said components are disclosed in the specification. The invention also relates to a method of assessing for the presence of EAG1 expressing cells and for a method of blocking EAG1 function in said cells. The invention further relates to a method of treating diseases with the help of said antibody or antibody fragment or derivative thereof.

In this specification, a number of documents are cited. The disclosure content of these documents including manufacture's manuals, is herewith incorporated by reference in its entirety.

Potassium channels are ubiquitously present in cells. One reason for this is supposed to be that the channels are involved in the regulation of the resting potential of cells, which has been regarded as their major role. However, given the above mentioned ubiquitous presence of the channels in different cell types, it has been speculated that they might also be involved in more general functions, such as "housekeeping" functions. In particular, experimental evidence has been presented [Ouadid-Ahidouch H et al., 2001] suggesting their implication in the cell division cycle hinting at their possible involvement in cancerogenesis. Indeed, members of the eag family EAG1, and herg have been proposed to be preferentially expressed in cancer cells [Meyer R et al., 1999; Bianchi I et al., 1998]. Since said channels are also expressed in various cell types and in particular in dividing cells, including cancer cells such as neoplastic cells it is of high medical interest to provide tools which might be used in therapeutic and/or diagnostic applications related to said potassium channels.

Antibodies which are directed against the human EAG1 ion channels were known in the prior art. European Patent application no. EP1073738 for example describes antibodies directed against said channel as well as the EAG1 ion channel.

In order to further broaden diagnostic and/or therapeutic applications it was desirable to have antibodies that specifically discriminate between mammalian, in particular human, EAG1 and EAG2, while also recognizing other mammalian EAG1 channels.

Thus, the technical problem underlying the present invention was to provide such antibodies which may be employed for the further specific study, diagnosis, prevention and treatment of defects and/or diseases interrelated with EAG1 from different mammalian species.

The solution to said technical problem is achieved by providing the embodiments characterized in the claims.

Accordingly, the present invention relates to an antibody, antibody fragment or derivative thereof comprising at least one complementarity determining region (CDR) of the VH and/or $V_L$ region, wherein the amino acid sequence determining said CDR(s) is selected from the group consisting of ($V_L$) SEQ ID Nos: 160 to 162, 166 to 168, 172 to 174, and 178 to 180 and selected from the group consisting of (VH) SEQ ID NOs: 163 to 165, 169 to 171, 175 to 177, and 181 to 183.

The term "antibody fragment or derivative thereof" in accordance with the present invention relates to antibody fragments and derivatives of the antibody of the invention as well as of the antibody fragments of the invention. Antibody fragments include Fab fragments, Fab' fragments F(ab')$_2$ fragments as well as Fv fragments. Derivatives of the antibody include scFv constructs, chimeric antibodies or humanized or human antibodies as long as they exhibit the desired capability of binding to EAG1.

The antibodies are for therapeutic purposes are optionally de-immunized. Examples of how to make de-immunized (humanized) antibodies may be found in U.S. Pat. Nos. 6,054,297, 5,886,152 and 5,877,293. For diagnostic purposes, the antibody, fragment or derivative thereof is preferentially labeled. Suitable labels include radioactive labels and fluorescent labels.

The term "complementary determining region" is well-defined in the art (see, for example, Harlow and Lane, "Antibodies, a laboratory manual", CSH Press, Cold Spring Harbour, 1988) and refers to the stretches of amino acids within the variable region of an antibody that primarily makes contact with the antigen.

As mentioned above, the antibody, antibody fragment or derivative thereof of the invention specifically discriminates between mammalian, in particular human, EAG1 and EAG2 while also recognizing other mammalian EAG1 channels. This is crucial if the properties of the antibody are to be taken advantage of in a clinical scenario, because failure to recognize rodent EAG1, while still discriminating from mouse EAG2, would restrict the possibility to use animal models to test for efficacy and—more importantly—safety of the antibody preparation.

As has been indicated above, the specificity of the antibody, antibody fragment or derivative thereof lies in the amino acid sequence of the complementarity determining region, a phenomenon which is known in the art. Each variable domain (the heavy chain VH and light chain $V_L$) of an antibody comprises three complementarity determining regions sometimes called hypervariable regions, flanked by four relatively conserved framework regions or "FRs". Often, the specificity of an antibody is determined or largely determined by a CDR such as a CDR of the VH chain. The person skilled in the art will readily appreciate that the variable domain of the antibody, antibody fragment or derivative thereof having the above-described CDRs can be used for the construction of antibodies of further improved specificity and biological function. Insofar, the present invention encompasses antibodies, antibody fragments or derivatives thereof comprising at least one CDR of the above-described variable domains and which advantageously have substantially the same, similar or improved binding properties as the antibody described in the appended examples. Starting from an antibody that comprises at least one CDR as recited in the attached sequence listing and required by the main embodiment of the invention, the skilled artisan can combine further CDRs from the originally identified monoclonal antibodies or different antibodies for an enhanced specificity and/or affinity. CDR-grafting is well-known in the art and can also be used to fine-tune the specific affinity in other properties of the antibody, fragment or derivative thereof of the invention, as long as the original specificity is retained. It is advantageous that the antibody, fragment or derivative comprises at least two, more preferred at least three, even more preferred at least four such as at least five and particularly preferred all six CDRs of the original mouse antibody. In further alternatives of the invention, CDRs from different originally identified monoclonal antibodies may be combined in a new antibody entity. In these cases, it is preferred that the three CDRs of the heavy chain originate from the same antibody whereas the three CDRs of the light chain all originate from a different (but all from the same) antibody. The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y.

The antibodies of the invention furthermore show advantageous properties with respect to their binding specificity and biological activity. In particular, it could be shown that the antibodies of the invention not only recognize the human EAG1 ion channel, but also are able to recognize EAG1 ion channels of other mammalian species. Said species include but are not limited to rat, mouse, non human primates.

Preferably, the EAG1 antibody of the invention exhibits at least one of the following characteristics:
  binding to a 3-dimensional or linear epitope in the assembly region
  binding to a linear or 3-dimensional epitope in the extracellular pore-domain-binding to the extracellular domain
  binding to the c-terminal intracellular domain
  binding with high affinity These antibodies thus have the advantage that they can be used in the specific detection of EAG1 over a broad range of experimental animals as well as for human tissue. Costs for the production of antibodies recognizing EAG1 in different species may thus be decreased.

The antibodies of the invention allow the specific recognition of the mammalian EAG1 potassium channels both in vitro and in vivo.

Preferably, binding of the antibody of the invention to EAG1 exhibits at least one of the following characteristics:
  inhibiting K+ channel mediated current,
  resulting in internalisation of ion channels,
  interfering with subunit assembly of ion channels,
  decreasing the release or activation of second messengers,
  decreasing or inhibiting cell growth,
  interfering with the formation of ion channel homo-/heteromultimers.

EAG1 expressing cells which have bound the antibody of the invention on the cell surface are finally attacked by immune system functions such as the complement system or cell mediated cytotoxicity.

As mentioned above and in other words, the antibodies of the invention show advantageous properties with respect to their binding specificity and biological activity, in particular with respect to their capacity to recognize epitopes of the EAG1 ion channel in different mammals and to decrease cell growth. Since the pharmaceutical and/or diagnostic applications of the antibodies of the invention include, but are not limited to humans, some of the antibodies of the invention (antibodies ImAb 3 and ImAb 4) were humanized; SEQ ID NOs 9 to 40) and were further developed in order to minimize potential negative immunogenic side effects when used in humans.

The original monoclonal antibodies that form part of the invention and gave rise to further preferred embodiments of the invention, were raised in mice. The murine antibodies were adapted to the human antibody sequence in order to reduce the immunogenicity in humans by genetic engineering. In such engineered antibodies, the subtype IgG1 (heavy chain) and kappa (light chain) were chosen to evoke the strongest immune activation.

Experimentally, for the monoclonal antibody generation, a fusion protein that contained the pore region of Eag1 (loop between fifth and sixth transmembrane segment, pos. 369-433; Region A) and a segment of the C-terminus of Eag1 (Pos. 850-920; region B) was used as the antigen. Similarity in those regions between Eag1 and Eag2 is 69% and 62% respectively. Region A is extracellular, region B is, under the accepted topographic model, intracellular.

The antibodies generated were checked by ELISA and BIAcore for selectivity between Eag1 and Eag2. Only a surprisingly small number of them qualified and were subcloned. Of these, five have been maintained. Four of them recognize an epitope in region A, and only one recognizes an epitope in region B. All four "A-type" antibodies recognize linear epitopes, and three of them share a single one, although, their CDRs are possibly different. The "B-type" antibody recognizes a three-dimensional epitope.

The properties of the resulting antibodies were characterized with respect to their binding affinities (FIG. 2), specificity (FIG. 3), the epitope they recognize and bind (FIG. 4) and the inhibition of the EAG1 ion channel FIG. 6. The properties of the antibodies of the invention to induce ion channel internalisation were investigated by immunoflurescence (FIG. 5). Furthermore the ability of the antibodies to inhibit cell growth were characterized in cell proliferation assays (FIGS. 7, 8a, 8b) and soft agar assays (FIG. 9). The results of these experiments showed that the antibodies indeed possess unexpected biological specificities.

In a preferred embodiment of the present invention said antibody, antibody fragment or derivative thereof specifically binds to/interacts with at least one epitope of the extracellular or intracellular domain of the mammalian EAG1 ion channel, and does not bind to/interact with the mammalian EAG2 ion channel.

The term "extracellular domain" according to the present invention is a term well-known in the art and relates to the portion of the EAG1 channel extending into the extracellular environment. This domain comprises, among others, amino acids 374-452 of the mammalian EAG1 molecule.

The term "intracellular domain" as used in connection with the present invention denotes the portion of the mammalian EAG1 channel extending into the cytoplasm. The domain comprises amino acids 872-932.

In a further preferred embodiment of the invention, the antibody is a monoclonal antibody.

Monoclonal antibodies can be prepared, for example, by the well-established techniques as originally described in Kohler and Milstein, Nature 256 (1975), 495, and Galfre, Meth. Enzymol. 73 (1981), 3, which comprise the fusion of mouse myeloma cells to spleen cells derived from immunized mammals with modifications developed by the art.

An effective strategy to target tumor cells, that is based on the discovery of the mechanisms of tumor development, is the usage of monoclonal antibodies. For example Herceptin™, an antibody directed against the receptor tyrosine kinase HER2, improves the median survival rate of breast cancer patients by approximately 25% compared with chemotherapy alone, and has only very mild side effects. Other strategies to use monoclonal antibodies in tumor therapy include immunotoxins, like Mylotarg™, a recombinant IgG4 kappa antibody conjugated to calicheamicin, and antibodies labelled with radioisotopes, as for example Zevalin™.

In an additionally preferred embodiment of the invention, the antibody fragment or derivative thereof is a Fab-fragment, a F(ab$_2$)'-fragment, a single-chain antibody, a chimeric antibody, a CDR-grafted antibody, a bivalent antibody-construct, a humanized antibody, a human, a synthetic antibody, or a chemically modified derivative thereof, a multispecific antibody, a diabody, a Fv-fragment, or another type of a recombinant antibody Fragments or derivatives of the above antibodies directed to the aforementioned epitopes can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to an epitope of EAG1 (Schier, Human Antibodies Hybridomas 7 (1996), 97-105; Malmborg, J. Immunol. Methods 183 (1995), 7-13).

The nucleic acid molecules, vectors and host cells may be used to make mutated EAG1 antibodies. The antibodies may be mutated in the variable domains of the heavy and/or light chains to alter a binding property of the antibody. For example, a mutation may be made in one or more of the CDR regions to increase or decrease the Kd of the antibody for EAG1, or to alter the binding specificity of the antibody. Techniques in site directed mutagenesis are well-known in the art. See, e.g., Sambrook et al. and Ausubel et al., supra. Furthermore mutations are made at an amino acid residue that is known to be changed compared to germline in a variable region of an EAG1 antibody. In another aspect, the nucleic acid molecules are mutated in one or more of the framework regions. A mutation may be made in a framework region or constant domain to increase the half-life of the EAG antibody. See, e.g., WO 00/09560, published Feb. 24, 2000. A mutation in a framework region or constant domain may also be made to alter the immunogenicity of the antibody, to provide a site for covalent or non-covalent binding to another molecule, or to alter such properties as complement fixation. Mutations may be made in each of the framework regions, the constant domain and the variable regions in a single mutated antibody. Alternatively, mutations may be made in only one of the framework regions, the variable regions or the constant domain in a single mutated antibody.

The production of chimeric antibodies is described, for example, in WO89/09622. Methods for the production of humanized antibodies are described in, e.g., EP-A1 0 239 400 and WO90/07861. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. As discussed above, the antibody of the invention may exist in a variety of forms besides complete antibodies; including, for example, Fv, Fab and F(ab)2, as well as in single chains; see e.g. WO88/09344.

In yet another preferred embodiment of the invention, the antibody, antibody fragment or derivative thereof comprises at least one CDR of each of the $V_H$ and the $V_L$ chains.

In a more preferred embodiment of the invention, said CDRs are the CDR3s.

In a further preferred embodiment of the antibody, antibody fragment or derivative thereof of the invention, the light chain ($V_L$) is selected from the group consisting of SEQ ID NOs 2, 6, 10, 14, 18, 22, 26, 30, 34, 38, 43 and 47 and the heavy chain ($V_H$) is selected from the group consisting of SEQ ID NOs. 4, 8, 12, 16, 20, 24, 28, 32, 36, 40, 44 and 48.

The invention further relates to a nucleic acid molecule encoding the antibody, antibody fragment or derivative thereof of the invention. The nucleic acid molecule of the invention encoding the above-described antibody, antibody fragment or derivative thereof may be, e.g. DNA, cDNA, RNA or synthetically produced DNA or RNA or recombinantly produced chimeric nucleic acid molecule comprising any of those nucleic acid molecules either alone or in combination. The nucleic acid molecule may also be genomic DNA corresponding to the entire gene or a substantial portion thereof or to fragments and derivatives thereof. The nucleotide sequence may correspond to the naturally occurring nucleotide sequence or may contain single or multiple nucleotide substitutions, deletions or additions.

In a particular preferred embodiment of the present invention, the nucleic acid molecule is a cDNA molecule.

The invention also relates to a vector comprising a nucleic acid molecule of the invention. Said vector may be, for example, a phage, plasmid, viral or retroviral vector. Retroviral vectors may be replication competent or replication defective. In the latter case, viral propagation generally will occur only in complementing host/cells.

The nucleic acid molecules of the invention may be joined to a vector containing selectable markers for propagation in a host. Generally, a plasmid vector is introduced in a precipitate such as a calcium phosphate precipitate or rubidium chloride precipitate, or in a complex with a charged lipid or in carbon-based clusters, such as fullerens. Should the vector be a virus, it may be packaged in vitro using an appropriate packaging cell line prior to application to host cells.

Preferably, the vector of the invention is an expression vector wherein the nucleic acid molecule is operatively linked to one or more control sequences allowing the transcription and optionally expression in prokaryotic and/or eukaryotic host cells. Expression of said nucleic acid molecule comprises transcription of the nucleic acid molecule, preferably into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in E. coli, and examples for regulatory elements permitting expression in eukaryotic host cells are the AOXI or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 (Invitrogene), pSPORTI (GIBCO BRL). Preferably, said vector is an expression vector and/or a gene transfer or targeting vector. Expression vectors derived from viruses such as retroviruses, vaccinia virus, adenoassociated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (2001, Third Edition) N.Y. and Ausubel, Current Protocols in Molecular Biology, Green Publishing Associates and Wiley Interscience, N.Y. (1994). Alternatively, the nucleic acid molecules of the invention can be reconstituted into liposomes for delivery to target cells.

The invention further relates to a host comprising the vector of the invention. Said host may be a prokaryotic or eukaryotic cell. The polynucleotide or vector of the invention which is present in the host cell may either be integrated into the genome of the host cell or it may be maintained extrachromosomally. In this respect, it is also to be understood that the nucleic acid molecule of the invention can be used for "gene targeting" and/or "gene replacement", for restoring a mutant gene or for creating a mutant gene via homologous recombination; see for example Mouellic, Proc. Natl. Acad. Sci. USA, 87 (1990), 4712-4716; Joyner, Gene Targeting, A Practical Approach, Oxford University Press.

The host cell can be any prokaryotic or eukaryotic cell, such as a bacterial, insect, fungal, plant, animal, mammalian or, preferably, human cell. Preferred fungal cells are, for example, those of the genus *Saccharomyces*, in particular those of the species *S. cerevisiae*. The term "prokaryotic" is meant to include all bacteria which can be transformed or transfected with a polynucleotide for the expression of a variant polypeptide of the invention. Prokaryotic hosts may include gram negative as well as gram positive bacteria such as, for example, *E. coli, S. typhimurium, Serratia marcescens* and *Bacillus subtilis*. A polynucleotide coding for a mutant form of variant polypeptides of the invention can be used to transform or transfect the host using any of the techniques commonly known to those of ordinary skill in the art. Methods for preparing fused, operably linked genes and expressing them in bacteria or animal cells are well-known in the art (Sambrook, Molecular Cloning A Laboratory Manual, Cold Spring Harbor Laboratory (2001, Third Edition). The genetic constructs and methods described therein can be utilized for expression of variant antibodies, antibody fragments or derivatives thereof of the invention in, e.g., prokaryotic hosts. In general, expression vectors containing promoter sequences which facilitate the efficient transcription of the inserted nucleic acid molecule are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The antibodies, antibody fragments or derivatives thereof of the invention can then be isolated from the grown medium, cellular lysates, or cellular membrane fractions. The isolation and purification of the microbially or otherwise expressed antibodies, antibody fragments or derivatives thereof of the invention may be by any conventional means such as, for example, preparative chromatographic separations and immunological separations such as those involving the use of monoclonal or polyclonal antibodies.

In a preferred embodiment of the invention, the host is a bacteria, fungal, plant, amphibian or animal cell. Preferred animal cells include but are not limited to Chinese hamster ovary (CHO) cells, baby hamster kidney (BHK) cells, monkey kidney cells (COS), 3T3 cells, NSO cells and a number of other cell lines.

In another preferred embodiment, said animal cell is an insect cell. Preferred insect cells include but are not limited to cells of the SF9 cell lines In a more preferred embodiment of the invention, said host is a human cell or human cell line. Said human cells include, but are not limited to Human embryonic kidney cells (HEK293, 293T, 293 freestyle). Furthermore, said human cell lines include, but are not limited to HeLa cells, human hepatocellular carcinoma cells (e.g., Hep G2), A549 cells.

Cell lines of particular preference are selected through determining which cell lines have high expression levels.

It is likely that antibodies expressed by different cell lines or in transgenic animals will have different glycosylation status. However, all antibodies encoded by the nucleic acid molecules provided herein, or comprising the amino acid sequences provided herein are part of the instant invention, regardless of the glycosylation status of the antibodies.

The invention also provides transgenic non-human animals comprising one or more nucleic acid molecules of the invention that may be used to produce antibodies of the invention. Antibodies can be produced in and recovered from tissue or body fluids, such as milk, blood or urine, of goats, cows, horses, pigs, rats, mice, rabbits, hamsters or other mammals. See, e.g., U.S. Pat. Nos. 5,827,690, 5,756,687, 5,750,172, and 5,741,957. As described above, non-human transgenic animals that comprise human immunoglobulin loci can be produced by immunizing with EAG1 or a portion thereof.

The invention additionally relates to a method for the preparation of an antibody, antibody fragment or derivative thereof, comprising culturing the host of the invention under conditions that allow synthesis of said antibody, antibody fragment or derivative thereof and recovering said antibody, antibody fragment or derivative thereof from said culture.

The transformed hosts can be grown in fermentors and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes, "Protein Purification", Springer-Verlag, N.Y. (1982). The antibody or its corresponding immunoglobulin chain(s) of the invention can then be isolated from the growth medium, cellular lysates, or cellular membrane fractions. The isolation and purification of the, e.g., microbially expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention.

It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level. The DNAs are then expressed in a suitable host system, and the expressed proteins are collected and renatured, if necessary.

In a preferred embodiment of the present invention, the antibody, antibody fragment or derivative thereof are coupled to an effector, such as calicheamicin, Auristatin E or monomethylauristatin E (MMAE), a radioisotope or a toxic chemotherapeutic agent such as geldanamycin and maytansine. Preferably, these antibody conjugates are useful in targeting cells, e.g. cancer cells, expressing EAG1, for elimination. Moreover, the linking of antibodies/antibody fragments of the invention to radioisotopes e.g. provides advantages to tumor treatments. Unlike chemotherapy and other forms of cancer treatment, radioimmunotherapy or the administration of a radioisotope-antibody combination directly targets the cancer cells with minimal damage to surrounding normal, healthy tissue. Preferred radioisotopes include g. $^{3}$H, $^{14}$C, $^{15}$N, $^{35}$S, $^{90}$Y, $^{99}$Tc, $^{111}$In, $^{125}$I, $^{131}$I).

Furthermore, the antibodies of the invention can be used to treat cancer when being conjugated with toxic chemotherapeutic drugs such as geldanamycin (Mandler et al., *J. Natl. Cancer Inst.,* 92(19), 1549-51 (2000)) and maytansine, for example, the maytansinoid drug, DM1 (Liu et al., *Proc. Natl. Acad. Sci. U.S.A.* 93:8618-8623 (1996)) and auristatin-E (Doronina et al., *Nat. Biotechnol.* 21:778-784 (2003). Different linkers that release the drugs under acidic or reducing conditions or upon exposure to specific proteases are employed with this technology. The antibodies of the invention may be conjugated as described in the art.

Yet, the invention further relates to a pharmaceutical composition comprising the antibody, antibody fragment or derivative thereof, the nucleic acid molecule, the vector, the host of the invention or an antibody, antibody fragment or derivative thereof obtained by the method of the invention.

The term "composition" as employed herein comprises at least one compound of the invention. Preferably, such a composition is a pharmaceutical or a diagnostic composition.

The composition may be in solid, liquid or gaseous form and may be, inter alia, in a form of (a) powder(s), (a) tablet(s), (a) solution(s) or (an) aerosol(s). Said composition may comprise at least two, preferably three, more preferably four, most preferably five compounds of the invention or nucleic acid molecules encoding said compounds. Said composition may also comprise optimized antibodies, antibody fragments or derivatives thereof obtainable by the methods of the invention.

It is preferred that said pharmaceutical composition, optionally comprises a pharmaceutically acceptable carrier and/or diluent. The herein disclosed pharmaceutical composition may be partially useful for the treatment of hyperproliferative diseases, skin diseases, inflammatory diseases or neuro-degenerative diseases. Said disorders comprise, but are not limited to psoriasis, Alzheimer's disease, multiple sclerosis, lateral amyotrophic sclerosis or Parkinsons's disease breast, lung, colon, kidney, lymphoma, skin, ovary, prostate, pancreas, esophagus, barret, stomach, bladder, cervix, liver, thyroid cancer, melanoma, hyperplastic or neoplastic diseases or other EAG expressing or overexpressing hyperproliferative diseases.

The present invention provides for pharmaceutical compositions comprising the compounds of the invention to be used for the treatment of diseases/disorders associated with EAG1 expression or overexpression.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. The compositions of the invention may also be administered directly to the target site, e.g., by biolistic delivery to an external or internal target site, like the brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 µg and 100 mg/kg body weight per dose; however, doses below or above this exemplary range are envisioned, especially considering the aforementioned factors. If the regimen is a continuous infusion, it should also be in the range of 1 pg to 100 mg per kilogram of body weight per minute.

Progress can be monitored by periodic assessment. The compositions of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition. It is particularly preferred that the pharmaceutical composition comprises further agents like, e.g. an additional antineoplastic agent, small molecule inhibitor, anti-tumor agent or chemotherapeutic agent.

The invention also relates to a pharmaceutical composition comprising the antibody, antibody fragment or derivative thereof of the invention in combination with at least one anti-neoplastic agent. Said combination is effective, for example, in inhibiting abnormal cell growth.

Many anti-neoplastic agents are presently known in the art. In one embodiment, the anti-neoplastic agent is selected from the group of therapeutic proteins including but not limited to antibodies or immunomodulatory proteins. In another embodiment the anti-neoplastic agent is selected from the group of small molecule inhibitors or chemotherapeutic agents consisting of mitotic inhibitors, kinase inhibitors, alkylating agents, anti-metabolites, intercalating antibiotics, growth factor inhibitors, cell cycle inhibitors, enzymes, topoisomerase inhibitors, histone deacetylase inhibitors, anti-survival agents, biological response modifiers, anti-hormones, e.g. anti-androgens, and antiangiogenesis agents.

Furthermore, the pharmaceutical composition of the invention can also be used for veterinary purposes.

Additionally, the invention relates to the use of the antibody, antibody fragment or derivative thereof of the invention, the nucleic acid molecule, the vector, the host of the invention or an antibody, antibody fragment or derivative thereof obtained by the method of the invention for the preparation of a pharmaceutical composition for prevention or treatment of a hyperproliferative disease, inflammatory disease, psoriasis, or a neurodegenerative disease.

In a preferred embodiment of the use of the invention, said neurodegenerative disease is Alzheimer's disease, multiple sclerosis, lateral amyotrophic sclerosis or Parkinson's disease.

In another preferred embodiment of the use of the invention, said hyperproliferative disease is in particular breast, lung, colon, kidney, lymphoma, skin, ovary, prostate, pancreas, esophagus, barret, stomach, bladder, cervix, liver, thyroid cancer, melanoma, hyperplastic or neoplastic diseases or other EAG1 expressing or overexpressing hyperproliferative diseases.

In yet another embodiment the present invention relates to a diagnostic composition comprising the antibody, antibody fragment or derivative thereof of the invention, the nucleic acid molecule, the vector, the host of the invention or an antibody, antibody fragment or derivative thereof obtained by the method of the invention and optionally a pharmaceutically acceptable carrier.

The diagnostic composition of the invention is useful in the detection of an undesired expression or over-expression of the mammalian EAG1 potassium channel in different cells, tissues or another suitable sample, comprising contacting a sample with an antibody of the invention, and detecting the presence of EAG1 in the sample. Accordingly, the diagnostic composition of the invention may be used for assessing the onset or the disease status of a hyperproliferative disease. Furthermore, malignant cells, such as cancer cells expressing EAG1, can be targeted with the antibody, antibody fragment or derivative thereof of the invention. The cells which have bound the antibody of the invention might thus be attacked by immune system functions such as the complement system or by cell-mediated cytotoxicity, therefore reducing in number of or eradicating cancer cells. These considerations equally apply to the diagnosis of metastases and re-current tumors.

In another aspect of the present invention, the antibody, antibody fragment or derivative thereof of the invention is coupled to a labelling group. Such antibodies are particularly suitable for diagnostic applications. As used herein, the term "labelling group" refers to a detectable marker, e.g. a radiolabelled amino acid or biotinyl moieties that can be detected by marked avidin. Various methods for labelling polypeptides and glycoproteins, such as antibodies, are known in the art and may be used in performing the present invention. Examples of suitable labelling groups include, but are not limited to, the following: radioisotopes or radionuclides (e.g. $_3H$, $_{14}C$, $_{15}N$, $_{35}S$, $_{90}Y$, $_{99}Tc$, $_{111}In$, $_{125}I$, $_{131}I$), fluorescent groups (e.g. FITC, rhodamine, lanthanide phosphors), enzymatic groups (e.g. horseradish peroxidase, -galactosidase, luciferase, alkaline phosphatase), chemiluminescent groups, biotinyl groups, or predetermined polypeptide epitopes recognized by a secondary reporter (e.g. leucine zipper pair sequences, binding sites for secondary antibodies, metal binding domains, epitope tags).

In certain aspects, it may be desirable, that the labelling groups are attached by spacer arms of various lengths to reduce potential steric hindrance.

The above embodiment of the invention is particularly important. Since the antibodies of the invention show a broad scope of applicability with respect to different mammalian species that can be treated, the diagnostic composition of the invention is also useful and applicable in different mammalian species.

In another embodiment the present invention relates to a method of assessing for the presence of EAG1 expressing cells comprising contacting the antibody or antibody fragment or derivative thereof of the invention with cells or a tissue suspected of carrying EAG1 on their/its surface.

In an additional embodiment the present invention relates to a method of blocking EAG1 function comprising contacting the antibody or antibody fragment or derivative thereof of the invention with cells or a tissue suspected of carrying EAG1 on their/its surface.

In a preferred embodiment of the method of the invention, said contacting is in vitro.

In a preferred embodiment of the method of the invention, said contacting is in vivo.

The invention also relates to a method of treating a disease selected from a hyperproliferative disease, inflammatory disease, psoriasis, or a neurodegenerative disease comprising administering to a patient in need thereof a suitable dose of the antibody or antibody fragment or derivative thereof of the present invention.

In a preferred embodiment of the method of the invention, said neurodegenerative disease is Alzheimer's disease, multiple sclerosis, lateral amyotrophic sclerosis or Parkinson's disease.

In another preferred embodiment of the method of the present invention said hyperproliferation disease is breast, lung, colon, kidney, lymphoma, skin, ovary, prostate, pancreas, esophagus, barret, stomach, bladder, cervix, liver, thyroid cancer and hyperplastic and neoplastic diseases or other EAG expressing or overexpressing hyperproliferative diseases.

In another preferred embodiment of the method of the present invention wherein said inflammatory disease is pancreatitis or hepatitis.

The invention finally relates to a method of treating a disease wherein the antibody of the invention is administered to a mammal and wherein said disease is correlated directly or indirectly with the abnormal level of expression of EAG1.

Finally, the invention relates to a kit comprising the antibody, antibody fragment or derivative thereof of the invention, the nucleic acid molecule encoding said components and/or the vector of the invention.

All embodiments covering the compounds disclosed herein can be used as single compounds or in combination for the preparation of a medicament.

The Figures show:

FIG. 1 shows the CDR peptide sequences of CDR1, 2 and 3 of the light and heavy chains of the mouse clones ImAb1, 3, 4 and 5.

FIG. 2 shows the binding specificity/selectivity of the anti-Eag1 antibodies ImAb1 and ImAb3 of the invention. Said antibodies selectively recognize Eag1 and do not bind to the Eag2 antigen. In addition the BIAcore™ analysis shows that ImAb1 binds to the C-terminus of Eag1, whereas ImAb3 recognizes the pore domain of Eag1.

FIG. 3 shows an immunohistochemistry (IHC) analysis with anti-Eag1 antibodies ImAb1 and ImAb4 of rat brain sections including rat hippocampus and rat cerebellum. The IHC study demonstrates the cross-reactivity of anti-Eag1 antibodies of the invention with rat.

FIG. 4 Binding patterns of anti-Eag1 monoclonal antibodies with peptides on the SPOT cellulose membrane. The amino acids referred to in the epitope recognized column are those of: SEQ ID NOS 268, 269, 204, 269, 270 and 189, respectively, in order of appearance from top to bottom.

FIGS. 8a and b shows the inhibition of IPC-298 melanoma cell proliferation by mouse anti-Eag1 antibody ImAb4 labelled (in combination) with a secondary immunotoxin. The results demonstrate that the anti-Eag1 antibodies posses the ability to internalise and that armed antibodies of the invention specifically inhibit human cancer cell growth. Said antibodies are suitable for conjugation as primary immunotoxin and are effective in the inhibition of human cancer cell growth.

FIG. 9 shows the inhibition of anchorage independent cell growth of IPC-298 melanoma cells by anti-Eag1 antibody ImAb4 in the presence of a secondary immunotoxin.

Figure 10A:
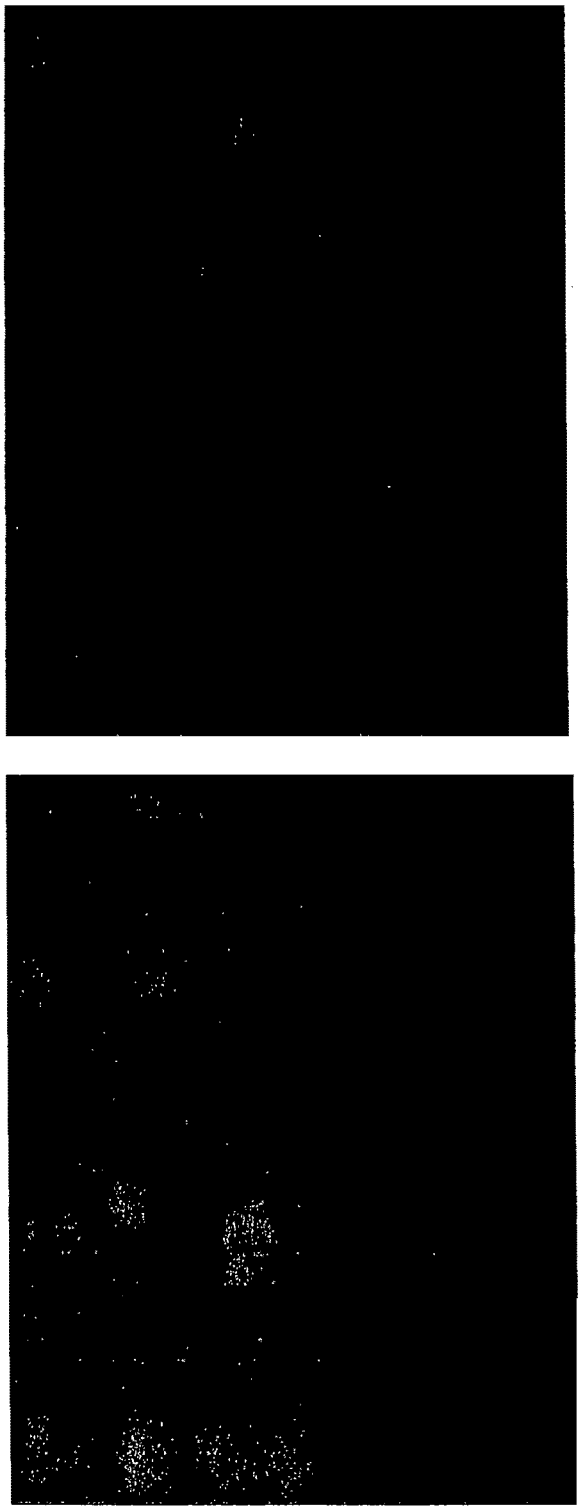

FIG. 10a shows an Immunofluorescence of Eag1 protein in human tumor cells using the anti-Eag1 antibody ImAb4. The result demonstrates that the antibodies of invention posses the ability to bind to endogenous Eag1 protein in human cancer cells.

FIG. 10b shows the result of an Eag1-ELISA performed with anti-Eag1 antibodies of the invention. (Said antibodies are able to bind and detect Eag1 protein in lysates of human cancer cells.)

FIG. 11 shows the expression of recombinant hu-ImAb3 in CHO K1 cells.

FIG. 12 shows the inhibition of colony formation of several human cancer cells my mouse anti-EAG1 antibodies of the invention. Anti-EAG1 antibody ImAb3 inhibit anchorage independent cell growth of breast cancer cells (FIG. 12a), ovary carcinoma cells (FIGS. 12b,c), melanoma cells (FIG. 12d), pancreas cancer cells (FIG. 12e), fibrosarcoma cells (FIG. 12f) and lung squamous carcinoma cells (FIG. 12g). Anti-EAG1 antibody iMab5 inhibit anchorage independent cell growth of ovarian carcinoma cells (FIG. 12b). FIG. 12c shows a dose-dependent inhibition of colony formation of ovary carcinoma cells by anti-EAG1 antibody ImAb3.

Figure 13:
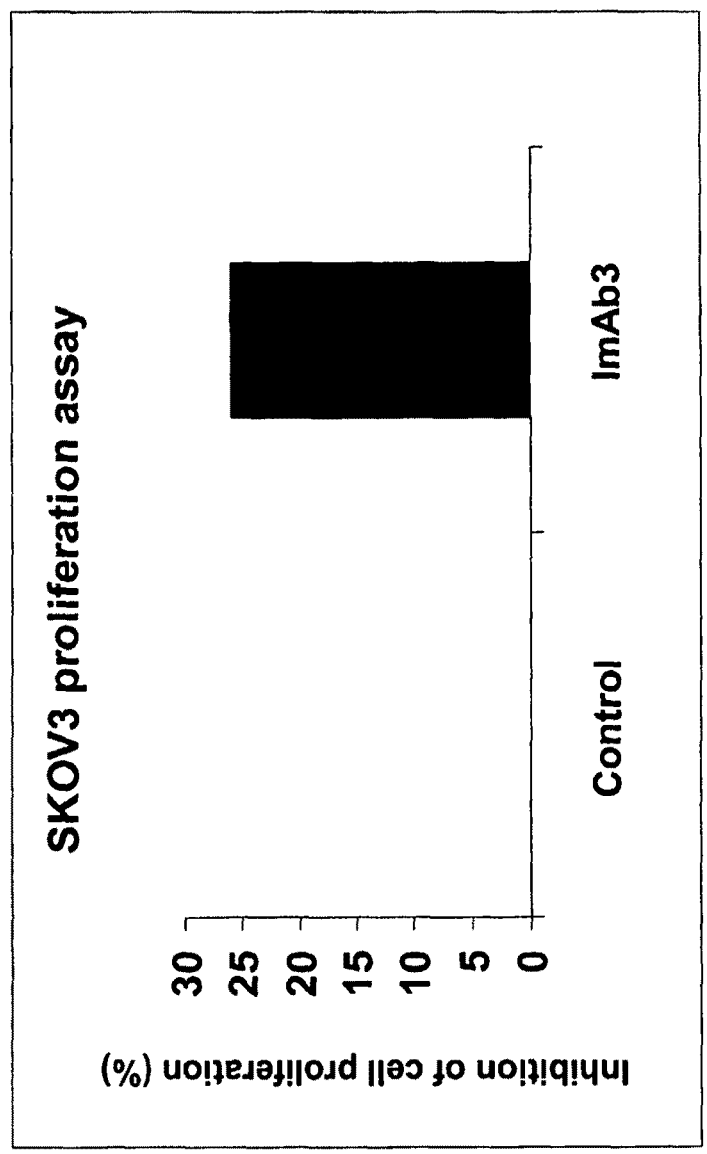

FIG. 13 shows the inhibition of SKOV3 ovary carcinoma cell proliferation by mouse anti-EAG1 antibody ImAb3 of the invention. Said antibody inhibits basal cell growth in human cancer cells.

Figure 14:
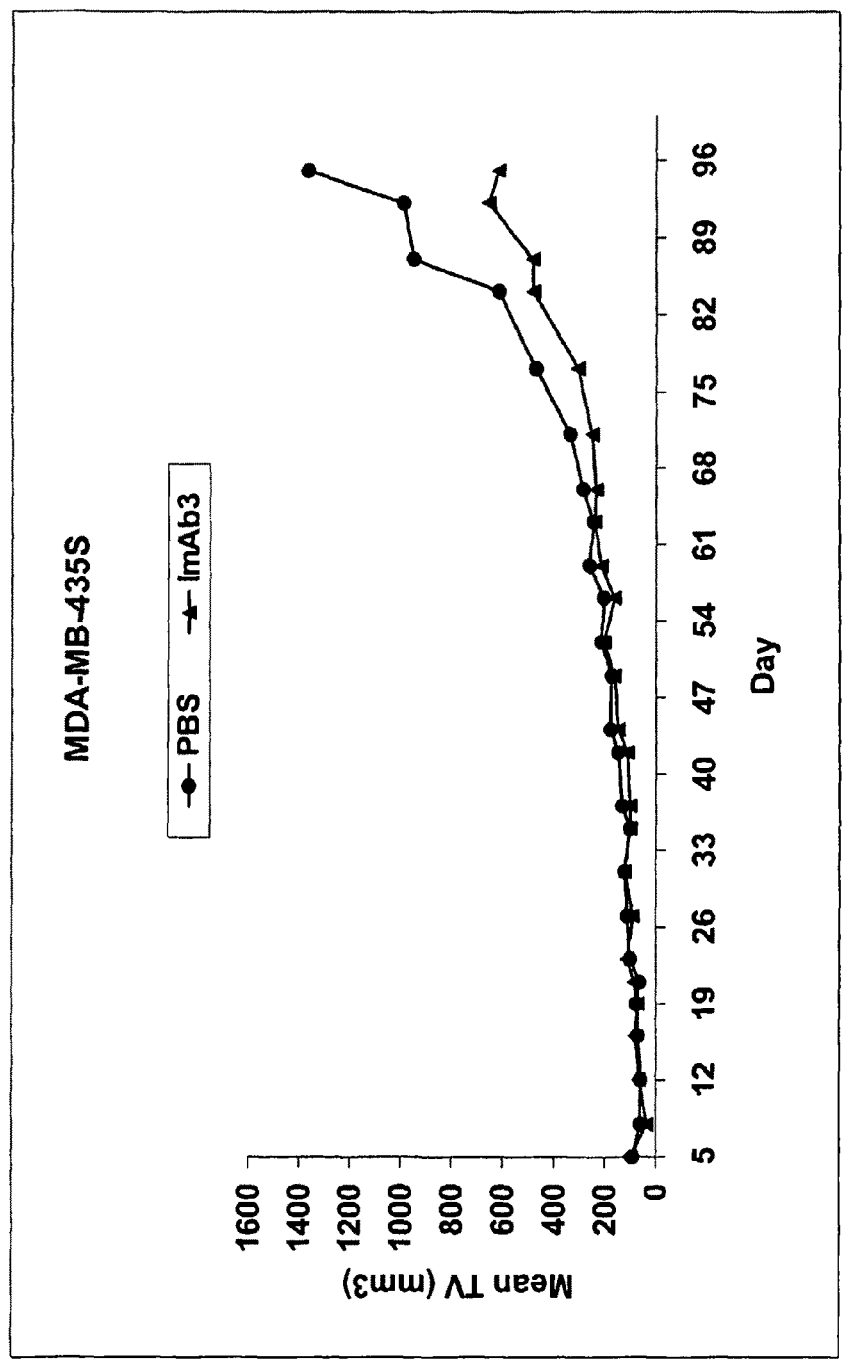

FIG. 14 shows the reduction of human tumor growth in female SCID mice by anti-EAG1 antibody ImAb3 of the invention. Said antibody inhibits in vivo growth of human breast carcinoma cells MDA-MB-435s cells.

Figure 15A:
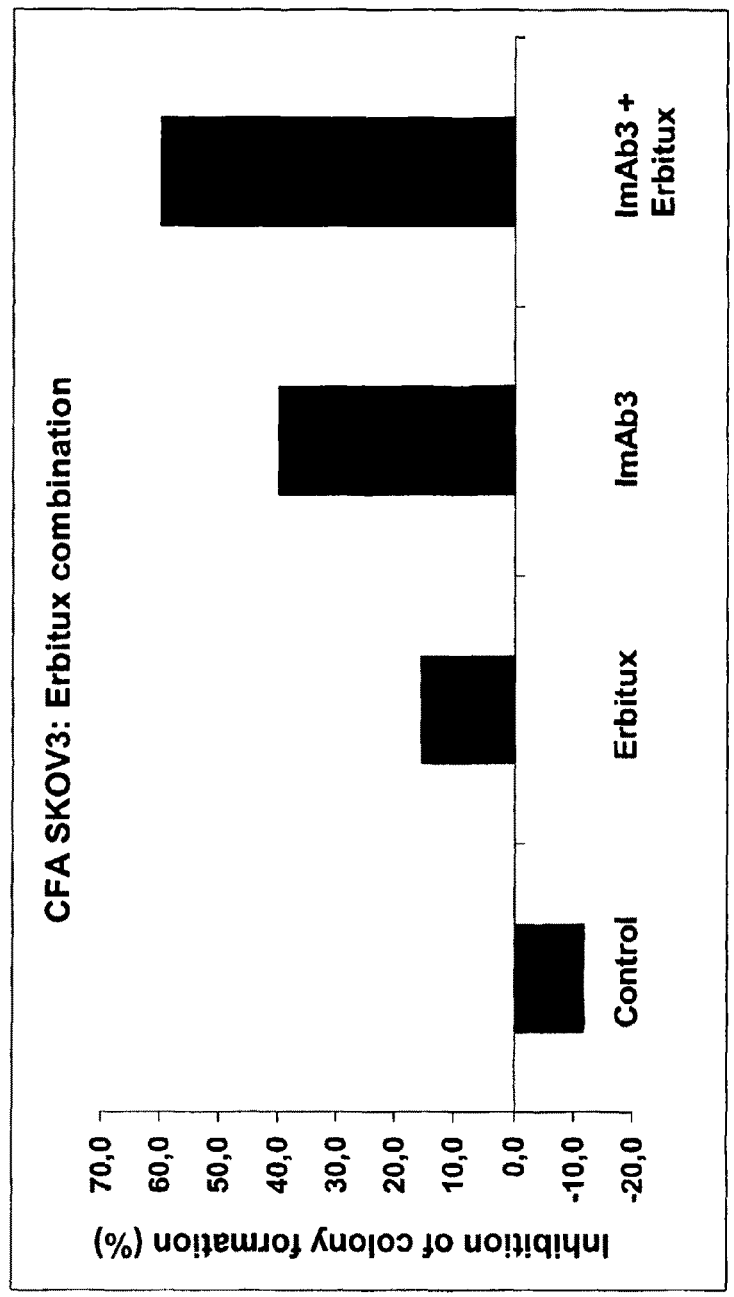
Figure 15B:
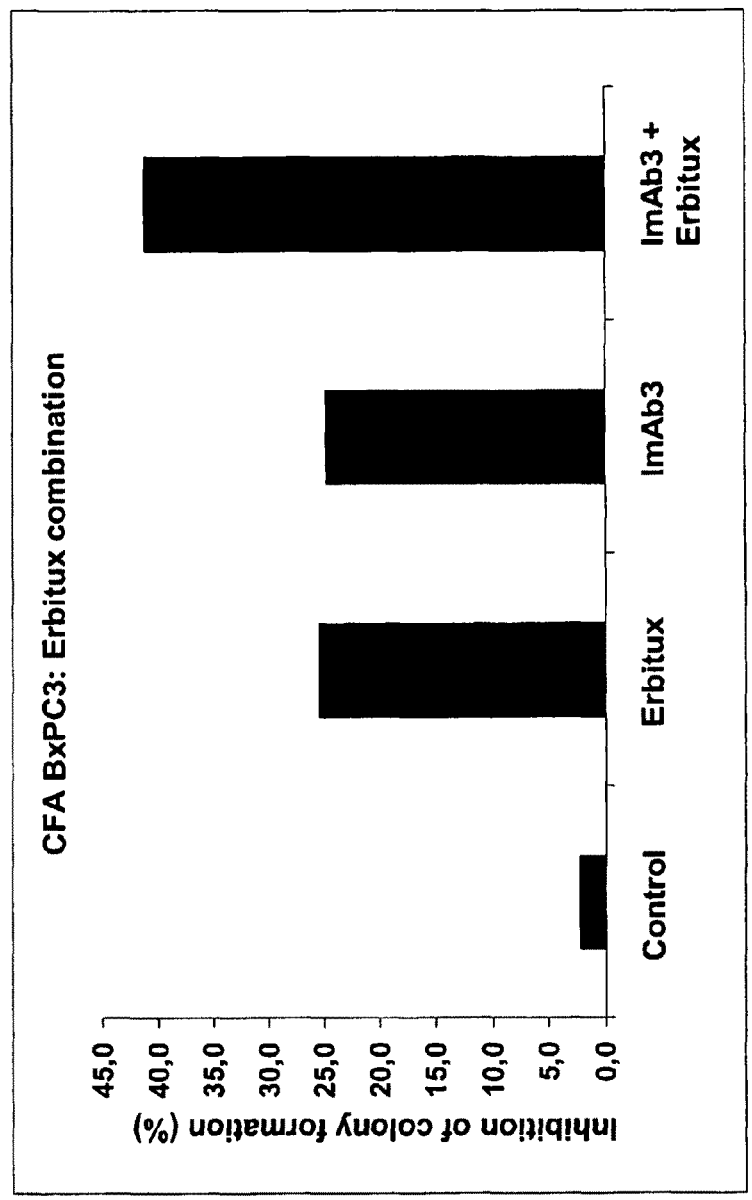

FIG. 15 shows the inhibition of anchorage independent cell growth of human ovary carcinoma and human pancreas cancer cells by human anti-EAG1 antibody ImAb3 in combination with therapeutic monoclonal anti-EGFR antibody Erbitux (FIGS. 15a and 15b). FIG. 15c demonstrates that combined treatment of human ovary cancer cells with ImAb3 and the anti-neoplastic agent Taxol very efficiently inhibits colony formation of this cell line. The inhibition of colony formation of human ovary carcinoma and melanoma cells with treatment of cells with anti-EAG1 antibody ImAb3 in combination with the anti-neoplastic agent Cisplatin is shown in FIGS. 15d and.

Figure 16:
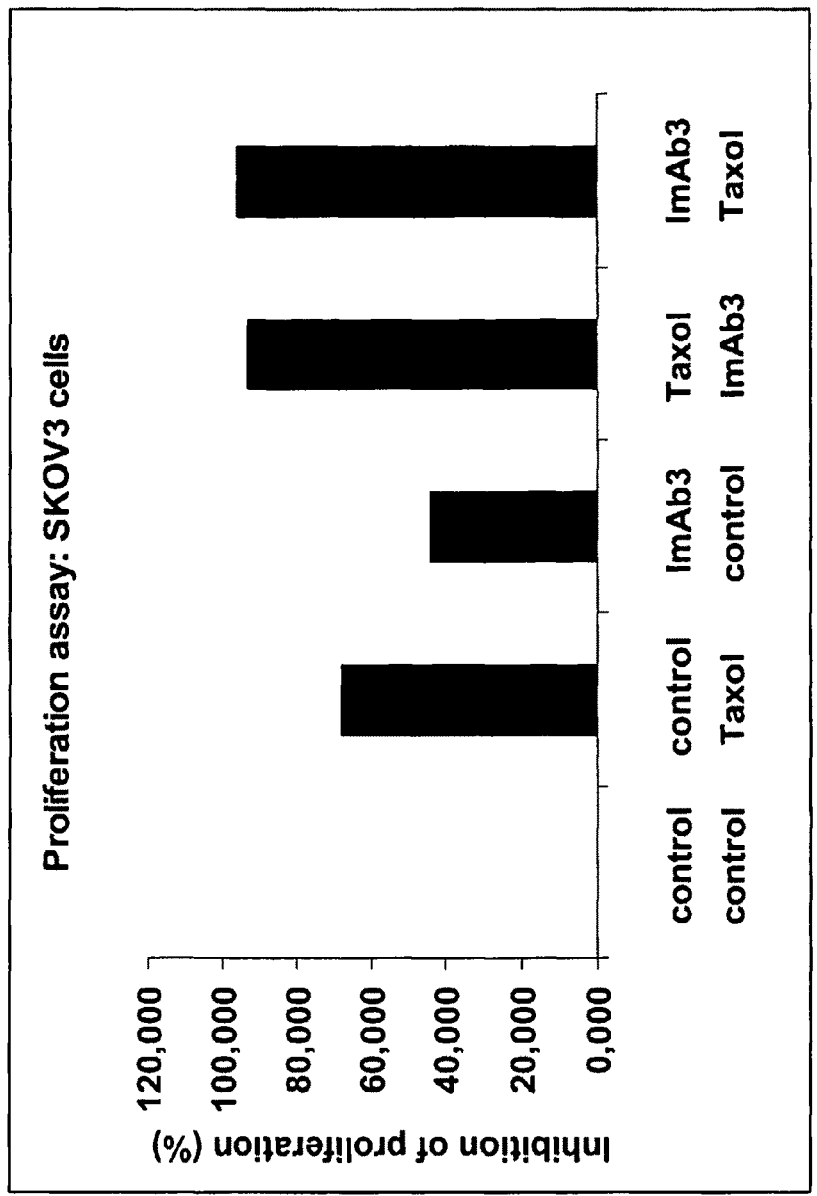

FIG. 16 demonstrates the inhibition of SKOV3 ovary carcinoma cell proliferation by mouse anti-EAG1 antibody ImAb3 of the invention in combination with the potent anti-neoplastic agent Taxol. Combined treatment of human ovary carcinoma cells with ImAb3 and Taxol inhibits basal cell growth in human cancer cells more efficiently then each anti-cancer drug alone.

Figure 17A:
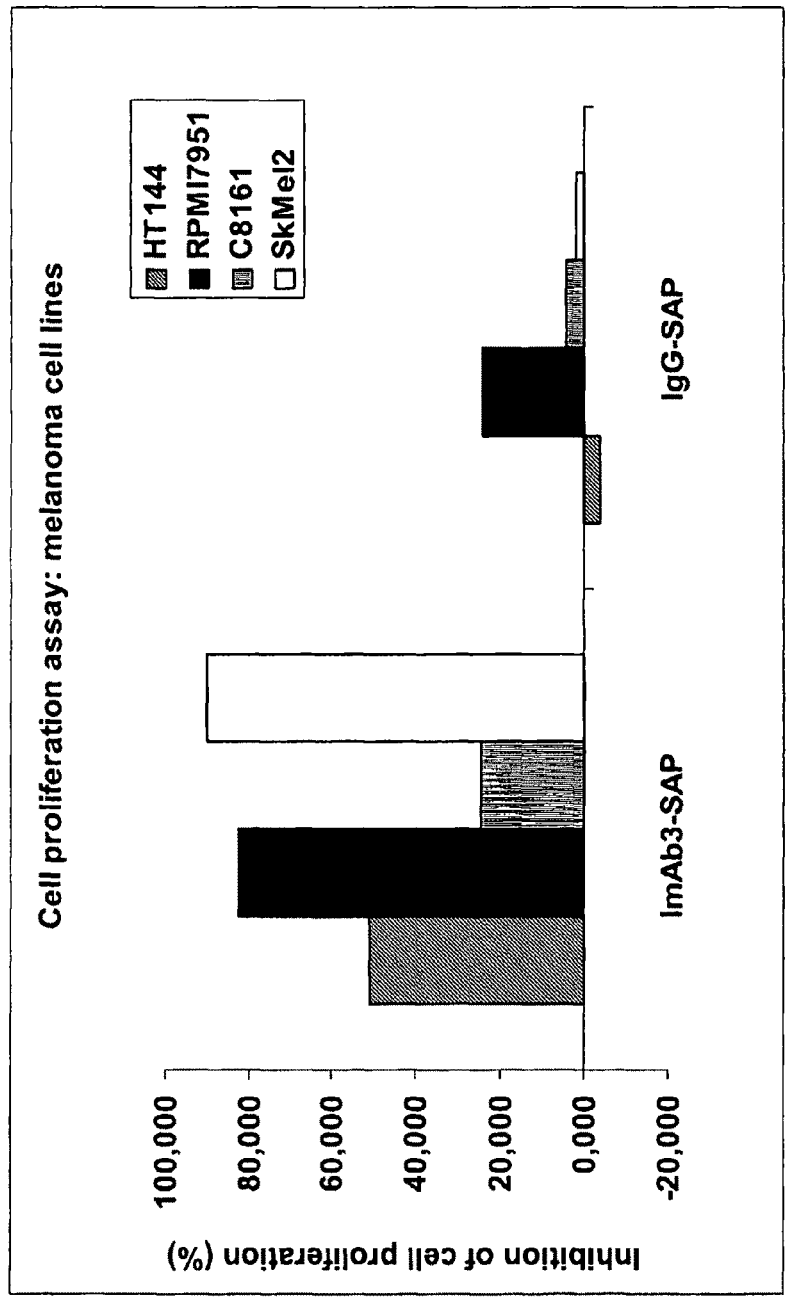
Figure 17B:
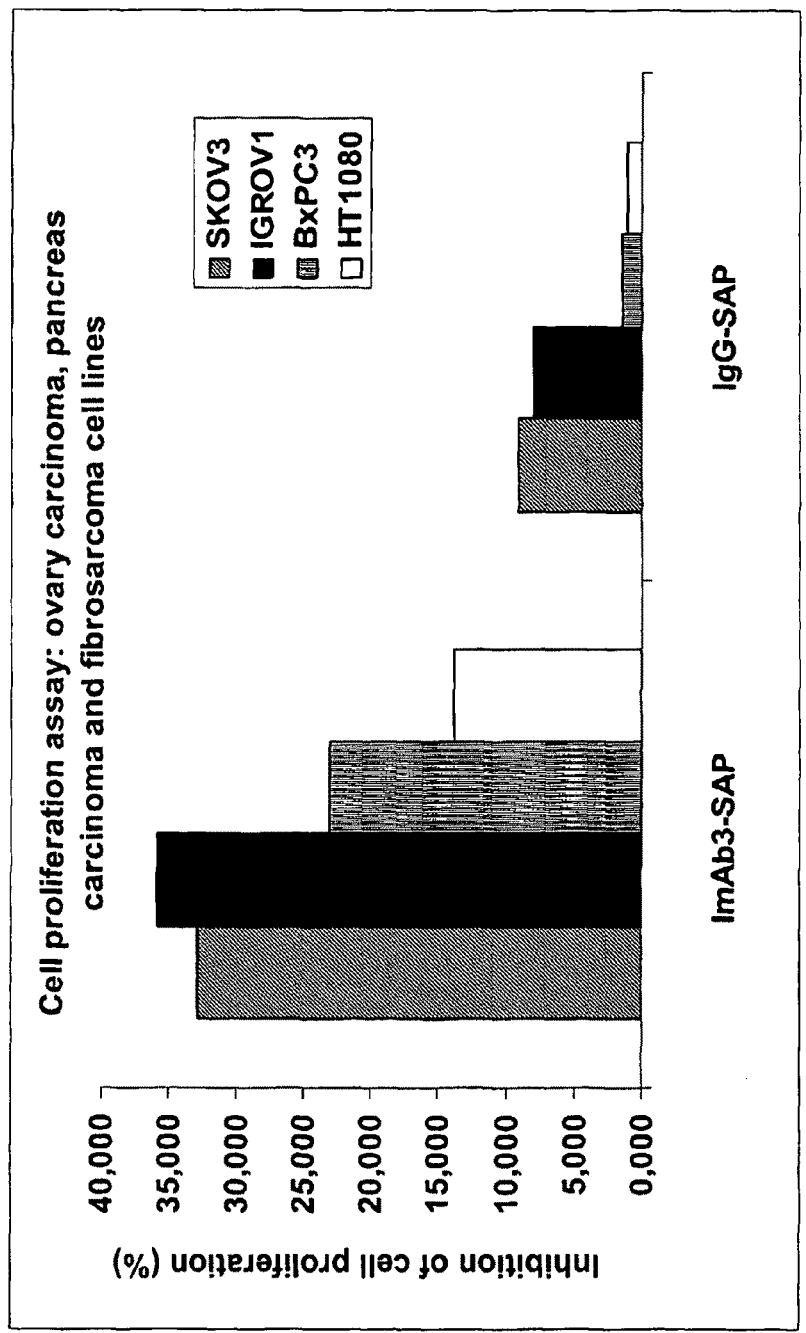
Figure 17C:
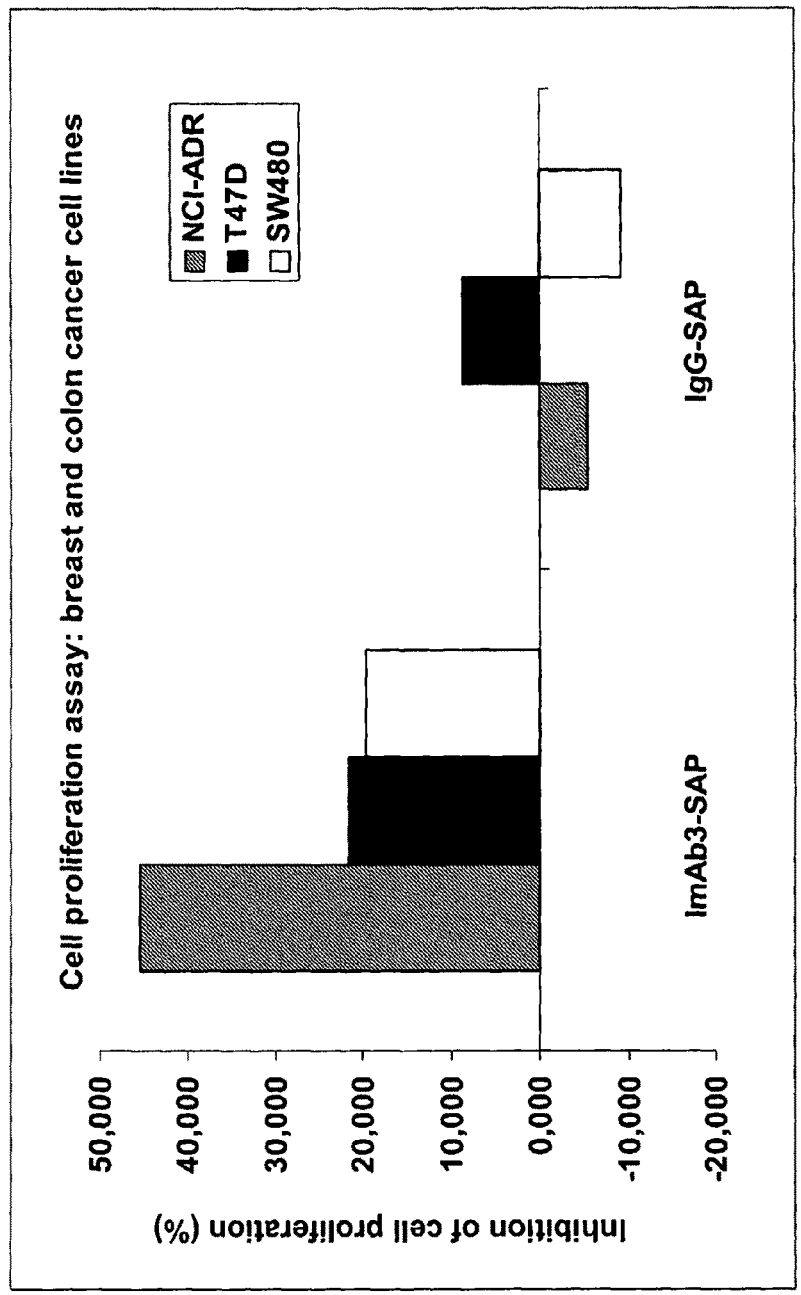

FIG. 17 shows the inhibition of cell proliferation of various different cancer cell lines by mouse anti-Eag1 antibody ImAb3 of the invention conjugated with the immunotoxin saporin. The results demonstrate that the Toxin-conjugated anti-Eag1 antibody ImAb3 very efficiently inhibits cell proliferation of a broad spectrum of human cancer cell lines. Saporin-conjugated anti-EAG1 antibody ImAb3 inhibits cell proliferation of melanoma cells (FIG. 17a), ovary and pancreas carcinoma cells (FIG. 17b), fibrosarcoma cells (FIG. 17b), breast and colon carcinoma cells (FIG. 17c).

Figure 18A:
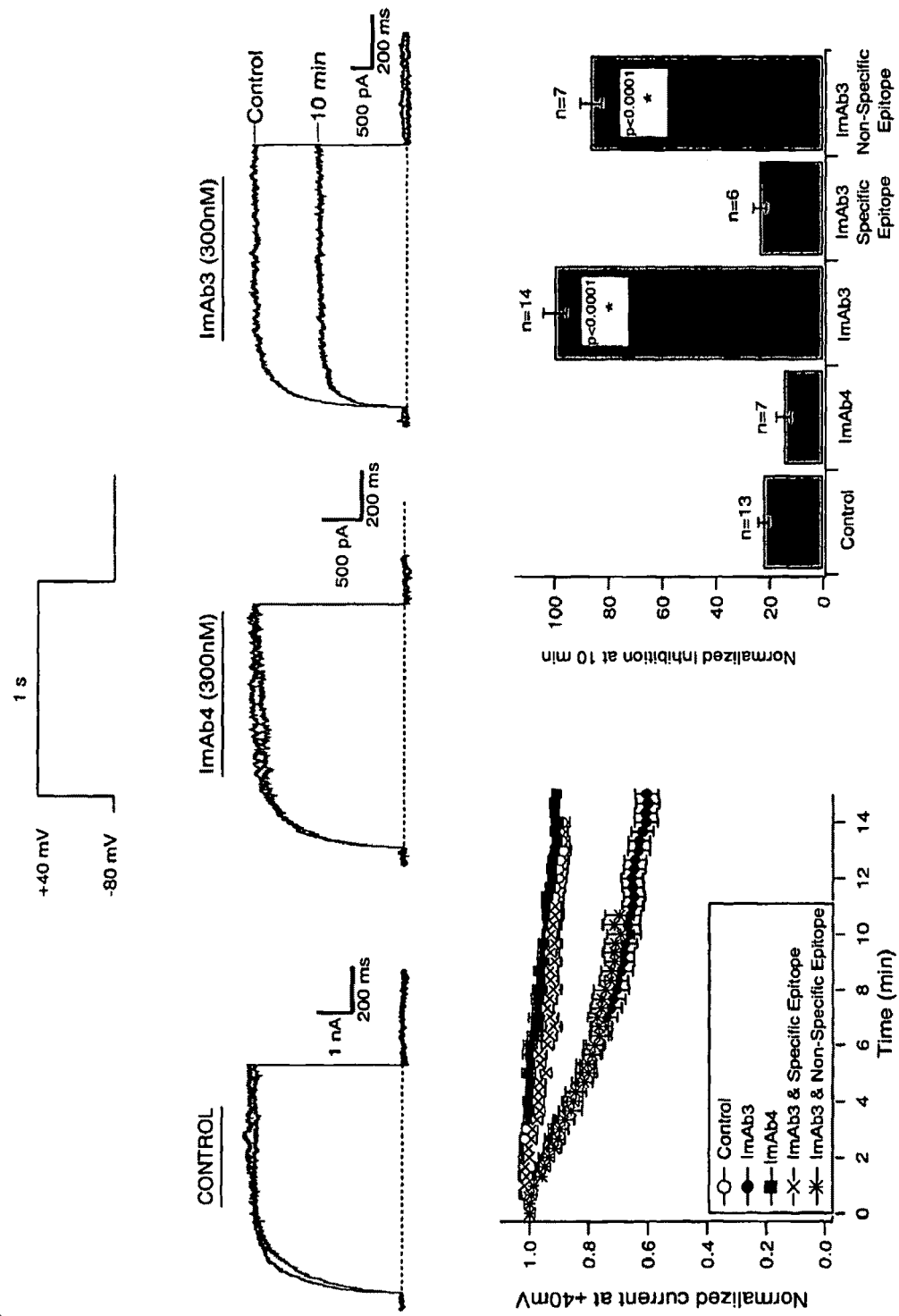
Figure 18B:
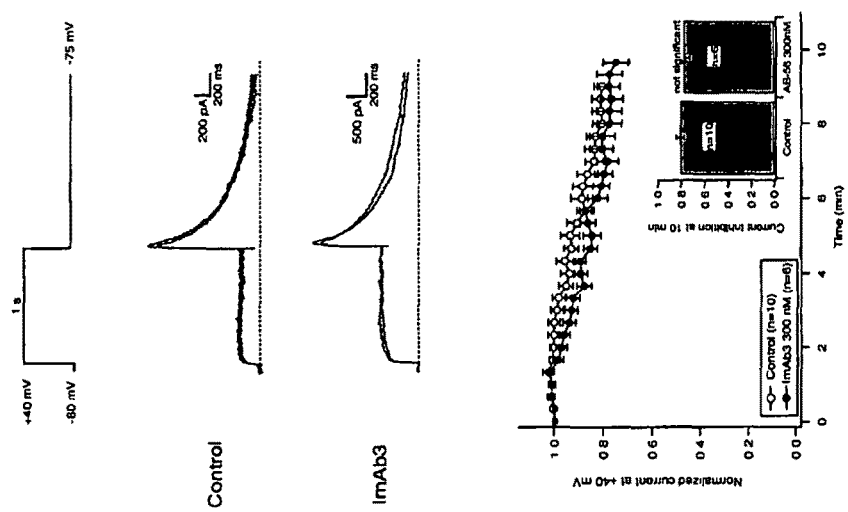

FIG. 18 depicts the inhibition of EAG1 currents by extracellular application of ImAb3 antibody. Representative traces at time 0 and 10 min of the application demonstrate that only application of ImAb3 succeeds in reducing the current amplitude. The current inhibition reaches about 35% of the total amplitude after 10-15 min (FIG. 18a). FIG. 18b shows the lack of effect of ImAb3 on HERG currents in technically reachable time range and concentrations.

Figure 19:
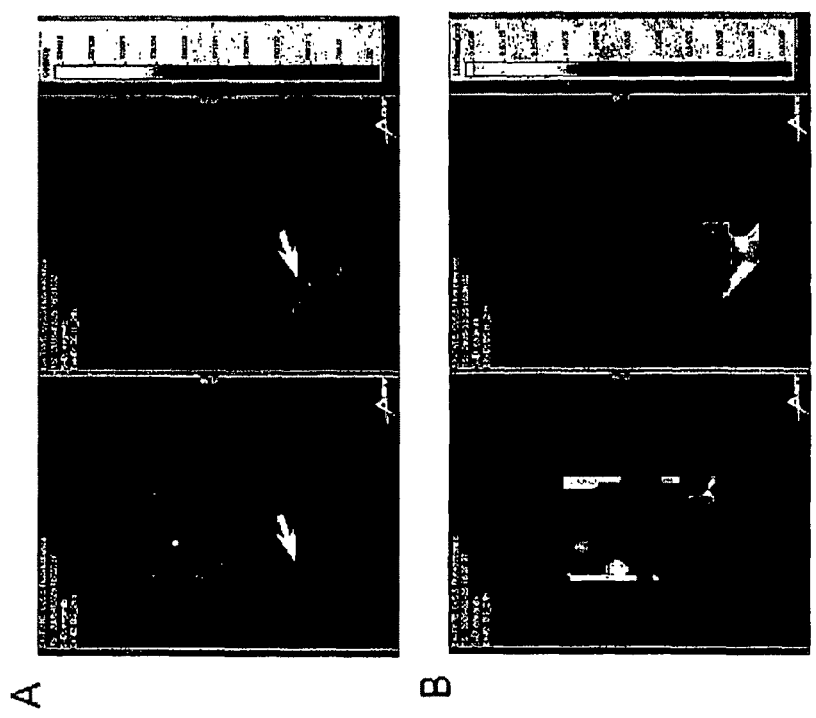

FIG. 19 shows pseudo-color images obtained from a mouse carrying an artificially implanted, EAG1 expressing tumor and a previously undetected metastatic implant (arrows). 100 μg labeled antibody were injected IV 24 h before imaging. FIG. 19 A represents color-coded fluorescence intensity, while FIG. 19 B shows fluorescence lifetime, which is compatible with AlexaFluor 680 in the positive areas.

The examples illustrate the invention

EXAMPLES

The following examples, including the experiments conducted and results achieved, are provided for illustrative purposes only and are not to be construed as limiting upon the present invention.

Example 1

EAG1 Antigen Preparation

A single colony of Epicurian Coli cells transformed with the vector encoding h1z was inoculated in 500 ml LB medium supplemented with Chloramphenicol 34 μg/ml and Ampicillin 100 μg/ml, at 31° C., 140 rpm. After 15 h of incubation, the culture was diluted 1/10 with LB-medium supplemented with the necessary antibiotics and incubated for 2 h at 31° C. with shaking (140 rpm). Overexpression of the fusion protein was induced by adding IPTG (final conc. 1 mM). The culture was incubated for 6 hours and then centrifuged 20 min at 2100×g at 4° C. The pellets were resupended in His-Resuspension Buffer and centrifuged for 10 min at 3.500 rpm and 4° C. The pellets were flash frozen in liquid Nitrogen and stored at −70° C.

Frozen bacterial cell pellet were resuspended in 15 ml 50 mM Tris/HCl, pH 7.9, 2 mM EDTA buffer supplemented with ~1 mg/ml lysozyme and shaken for 15 min at room temperature. Urea was added up to 8 M final concentration and the sample was sonicated. The solution was allowed to denature overnight with rotation at 4° C. and thereafter centrifuged for 30 min at 14.000×g. The supernatant was adjusted to 6 M urea in 1× binding buffer and filtered through a 0.45 μm filter. Affinity purification was performed using a BioCAD chromatography system, using a linear gradient from 100% binding buffer (20 mM Tris/HCl, pH 7.9, 5 mM Imidazole, 500 mM NaCl 6 M Urea) to 100% elution buffer (20 mM Tris/HCl, pH 7.9, 1 M Imidazole, 500 mM NaCl 6 M Urea).

The supernatant was loaded on His-tag resin peek column that was charged with 250 mM NiSO4 and pre-equilibrated with binding Buffer. The appropriate fractions were dialysed at 4° C. for 24 h against 3 changes of 3 M urea in PBS, 3×1 M Urea, 3×PBS and 3×0.5×PBS. The dialysed fusion protein was lyophilized and stored at −20 C until use.

Example 2

EAG1 Antibodies of the Invention

A. Preparation of the Antibodies
Immunization 2 mice (age 8 weeks) were primed by injecting with 50 ng antigen emulsified in complete adjuvant (Biogenes GmbH) and injected into the peritoneum at minus 120 days before fusion. All other injections were performed into peritoneum and intravenous by the following time schedule.

| Immunization | Days from fusion | Amount of antigen | Adjuvant | Injection route |
|---|---|---|---|---|
| 1 | 120 | 100 | Complete | i.p. |
| 2 | 60 | 100 | Incomplete | i.p. |
| 3 | 30 | 100 | Incomplete | i.p. |
| 4 | 15 | 100 | Incomplete | i.p. |
| 5 | 8 | 100 | Incomplete | i.p. |
| 6 | 3 | 200 | w/o adjuvant | i.p. + i.v. |
| 7 | 2 | 200 | w/o adjuvant | i.p. + i.v. |
| 8 | 1 | 200 | w/o adjuvant | i.p. + i.v. |

The myeloma cell line used was SP2/0-Ag14 from the German Collection of Microorganisms and Cell Cultures. The cells were described as not synthesizing or secreting immunoglobulin chains, being resistant to azaguanine at 20 pg/ml, and not growing in HAT medium. The SP2/0 cells were routinely maintained in tissue culture flasks in standard culture media (DMEM+10% fetal calf serum) supplemented with 20 Ng/ml 8-AZG to kill any HPRT+ revertants which can grow in HAT-medium. One week prior to fusion SP2/0 cells were maintained in standard culture media without 8-AZG.

The spleen from immunized mice was aseptically removed and single cell suspension was prepared. Spleen lymphocytes were fused with SP2/0 myeloma cell line (ratio 10 lymphocytes/1 SP2/0) in the presence of polyethylene glycol 4000. The cells so produced were then resuspended in DMEM containing HAT (hypoxantine $10^{-4}$M, aminopterin $10^{-5}$ M and thymidine $4\times10^{-5}$ M) and 20% preselected fetal calf serum. The cells were then plated into five 96 well tissue culture plates (Corning-Costar) containing peritoneal exudate cells as a feeder layer. The plates were incubated for 2 weeks at 37° C. in a humid atmosphere containing 5% carbon dioxide. During this period cells were fed two times with HAT medium and two times with HT medium. Wells with a positive growth of cells were screened for specific immunoglobulin content using an enzyme-linked immunosorbent assay (ELISA).

An indirect ELISA assay was used for screening the culture supernatants. Assay were carried out in 96 well flat bottom polystyrene microtiter plates prepared as follows: a 100 μl aliquot of a solution of 0.1 M carbonate/bicarbonate buffer, pH 9.6 containing immunogen (as positive control) or the equivalent fusion protein corresponding to Eag2 (as negative control) at a concentration 5 μg/ml was added to wells on the plate. After incubation overnight in a moist chamber at 4° C. the plate was washed four times with TBS containing 0.01% Triton X-100 and blocked with 22% Gelatin from cold water fish in TBS for 1 hour at room temperature.

100 μl aliquots of the hybridoma supernatants were added to the appropriate assay wells. Two negative control wells were included on each plate: one containing fresh culture medium the other supernatant from a well containing non-fused SP2/0 myeloma cells. The assay plates were incubated in a moist chamber at 37° C. for 2 h. It was then washed four times with tris-buffered saline (TBS, 50 mM Tris, pH 7.8, 150 mM sodium chloride) containing 0.01% Triton X-100. Determination of bound antibodies was accompanied with a number of alkaline phosphatase conjugates: goat anti-mouse IgG (Fc specific—for detection of IgG producers) and goat anti-mouse IgG (Fab specific—for detection both IgM and IgG producers) (Sigma, A-2429 and A-2179). Quantification of bound enzyme was performed with the help of a paranitrophenol-containing substrate buffer in a Bio-Rad Model 450 microplate reader.

Cells from positive IgG producer wells were transferred into wells of a 24 well plate and cultivated for one week. Cells from wells, which were still positive after this period were subjected to preclonal distribution (the cells were plated into five 96 well tissue culture plates containing peritoneal exudate cells as a feeder layer at concentration 10 cells per well) for further selection of a stable antibody producers. This procedure allows to select a most stable cell sub-populations, because due to random chromosome loss, wells with cells secreting the antibody of interest may gradually lose of antibody production.

Cells from wells, which gave a strongest positive signal in ELISA (IgG producers), were selected for cloning by limiting dilution. Cells from each positive well were distributed into two 96 well plates. In 8-10 days all plates were microscopically inspected for detection of monoclonal growth and culture supernatants from such wells were screened for specific immunoglobulin content by ELISA. Cells from six wells, which gave a best signal in ELISA were transferred into wells of 24 well plate and cultivated one more week. Then, assay procedure was repeated and one best clone from each primary population was subjected to a second limiting dilution cloning. All procedures that were made after the first cloning were repeated after the second one.

Two times cloned monoclonal cell lines were adapted to growth in medium with 15% fetal calf serum without any further growth stimulators and frozen in freezing 90% fetal calf serum, 10% DMSO at $3\times10^6$ cells per ml.

All antibodies were tested for specificity for Eag1 in Western blot and BIAcore experiments. Antibodies recognizing Eag2 either in ELISA or BIACore tests or showing immunostaining on heart muscle preparations (indicating cross-reactivity with HERG) were discarded as non-specific for Eag1.

Cloning of the Murine Antibody Genes

The subtype of the murine antibodies was identified by immunhistological methods. All the hybridomas expressed secreted antibodies of the subtype IgG2b heavy chain and kappa light chain. Total RNA was prepared from the hybridoma cells using the RNeasy kit (Qiagen). 1 μg of total RNA was translated into cDNA using the SMART PCR cDNA Synthesis Kit (Clontech). The primary cDNA was amplified for 20 cycles using the Long-distance polymerase chain reaction of the SMART PCR cDNA Synthesis Kit (Clontech). Subsequently the genes of the light and heavy chains expressed by the hybridomas were amplified by a PCR using specific primers and the proof-reading DNA polymerase Pwo (Roche).

To amplify the heavy chain genes the primers P1 and P2 were used. P1 is specific for the 5'-prime sequence of all cDNAs generated by the SMART PCR Synthesis Kit. P2 is a specific primer for the 3'-prime region of constant region of the murine IgG2b.

```
P8:
GTA ACA ACG CAG AGT ACG CGG G    (SEQ ID NO: 49)

P6:
TCA TTT ACC CGG AGA CCG G        (SEQ ID NO: 50)
```

To amplify the light chain genes the primers P1 and P3 were used. P1 is specific for the 5'-prime sequence of the all cDNAs generated by the SMART PCR Synthesis Kit. P3 is a specific primer for the 3'-prime region of constant region of the murine kappa light chain.

P8:
GTA ACA ACG CAG AGT ACG CGG G        (SEQ ID NO: 49)

P4:
CTA ACA CTC ATT CCT GTT GAA GCT C    (SEQ ID NO: 51)

1 µl of 100 µl first strand reaction cDNA), 1×PCR Buffer for Pwo (Roche), 200 µM each Nucleotide (dNTP, Roche), each primer 0.6 µM, 2.5 U Pwo proof reading polymerase (Roche), I a final volume of 50 µl was incubated in a thermocycler as follows:

| | |
|---|---|
| 94° C. | 3 min |
| 94° C. | 25 sec |
| 65° C. | 30 sec |
| 72° C. | 40 sec for light and 60 sec for heavy chain |
| | 10 cycles |
| 94° C. | 25 sec |
| 65° C. | 30 sec |
| 72° C. | 40 sec + 2 sec/cycle for light and 60 sec + 4 sec/cycle for heavy chain |
| | 20 cycles |
| 72° C. | 5 min |

The PCR products were analyzed on a 1% agarose gel. A single band of 750 bp for the light chain and a band of 1600 bp for the heavy chain were found. The PCR products were purified by QIAquick PCR purification kit (Qiagen) and phosphorylated using the polynucleotide kinase (PNK, Roche). 10 pmol DNA double strand (5 µg of light chain DNA or 10 µg heavy chain DNA) was incubated for 30 min at 37° C. in 50 mM Tris HCl, 10 mM MgCl2, 0.1 mM EDTA, 5 mM DTT, 0.1 mM Spermidine ph 8.2, including 100 µM ATP and 50 U PNK. The phosphorylated DNA was purified from an agarose gel by gel elution and ligated into a pBluescript II KS+ vector which had been cutted with the restriction enzyme EcoRV (Roche) and dephosphorylated with calf intestine alkaline phosphatase (Roche). The sequence of the cloned DNA was determined by DNA sequencing using T3 and T7 primer (Seqlab GmbH, Goettingen).

The DNA Sequence of Murine Light Chain ImAb4 is Shown in SEQ ID NO. 1

The Protein sequence of murine light chain ImAb4 is shown in SEQ ID NO: 2 The protein domains such as the signal peptide required for the secretion of the antibody and the complementarity determining regions (CDR) required for the specific binding of the antibody to its target were identified. The complementarity determining regions (CDR) and constant region of the antibody sequences were defined according to Chothia (Chothia C., Novotny J., Bruccoleri R., Karplus M. Journal of Molecular Biology. 186(3):651-63, 1985).

| | |
|---|---|
| Signal peptide | 1.-19. aminoacid |
| LC-CDR1 | 43.-58. aminoacid |
| LC-CDR2 | 74.-80. aminoacid |
| LC-CDR3 | 113.-121. aminoacid |
| Constant region: | 122.-238. aminoacid |

The DNA Sequence of Murine Heavy Chain ImAb4 is Shown in SEQ ID NO: 3
The Protein Sequence of Heavy Chain ImAb4 is Shown in SEQ ID NO: 4

The protein domains such as the signal peptide required for the secretion of the antibody and the complementarity determining regions (CDR) required for the specific binding of the antibody to its target were identified. The complementarity determining regions (CDR) and constant region of the antibody sequences were defined according to Chothia (Chothia C., Novotny J., Bruccoleri R., Karplus M. Journal of Molecular Biology. 186(3):651-63, 1985).

| | |
|---|---|
| Signal peptide | 1.-18. aminoacid |
| HC-CDR1 | 44.-54. aminoacid |
| HC-CDR2 | 69.-84. aminoacid |
| HC-CDR3 | 117.-126. aminoacid |
| Constant region: | 127.-473. aminoacid |

Light Chain Clone ImAb3:
The DNA Sequence of Murine Light Chain ImAb3 is Shown in SEQ ID NO: 5
The Protein Sequence of Murine Light Chain ImAb3 is Shown in SEQ ID NO: 6

The protein domains such as the signal peptide required for the secretion of the antibody and the complementarity determining regions (CDR) required for the specific binding of the antibody to its target were identified. The complementarity determining regions (CDR) and constant region of the antibody sequences were defined according to Chothia (Chothia C., Novotny J., Bruccoleri R., Karplus M. Journal of Molecular Biology. 186(3):651-63, 1985).

| | |
|---|---|
| Signal peptide | 1.-20. aminoacid |
| LC-CDR1 | 44.-60. aminoacid |
| LC-CDR2 | 76.-82. aminoacid |
| LC-CDR3 | 115.-122. aminoacid |
| Constant region | 123.-239. aminoacid |

The DNA Sequence of Murine Heavy Chain ImAb3 is Shown in SEQ ID NO: 7
The Protein Sequence of Murine Heavy Chain ImAb3 is Shown in SEQ ID NO:8

The protein domains such as the signal peptide required for the secretion of the antibody and the complementarity determining regions (CDR) required for the specific binding of the antibody to its target were identified. The complementarity determining regions (CDR) and constant region of the antibody sequences were defined according to Chothia (Chothia C., Novotny J., Bruccoleri R., Karplus M. Journal of Molecular Biology. 186(3):651-63, 1985).

| | |
|---|---|
| Signal peptide | 1.-19. aminoacid |
| HC-CDR1 | 45.-54. aminoacid |
| HC-CDR2 | 69.-87. aminoacid |
| HC-CDR3 | 120.-129. aminoacid |
| Constant region | 130.-476. aminoacid |

Generation of the Chimeric Antibodies:
The murine antibodies constant regions were replaced by human constant regions. Human light chain kappa and heavy chain IgG1 were cloned from blood cells of a human volunteer using the same approach as for the murine antibodies but specific human primers:

To amplify the human heavy chain genes the following primers were used:

P8:
GTA ACA ACG CAG AGT ACG CGG G        (SEQ ID NO: 49)

P16:
TCA TTT ACC CGG AGA CAG GGA GAG GC (SEQ ID NO: 52)

To amplify the human light chain genes the following primers were used:

P8:
GTA ACA ACG CAG AGT ACG CGG G        (SEQ ID NO: 49)

P15:
CTA ACA CTC ACC CCT GTT GAA G        (SEQ ID NO: 54)

To fuse the murine variable regions to the human constant regions the following PCRs were performed. First the human constant region was fused to the 3'-prime end of the murine variable region by using chimeric 3'-prime primers, that contained murine and human sequences (primer P7). Both the human constant region and the murine variable region were fused by a final PCR using both DNA fragments as a template and one specific primer for each DNA fragment.
Chimeric Antibody ImAb3:

P121: TCA TTT ACC CGG AGA CAG GGA GAG GC                                  (SEQ ID NO: 60)
P122: GGT AGT AGG TGG TAC TTC GAT GTC TGG GGC CAG GGA ACC CTG GTC (SEQ ID NO: 61)
      ACC

The murine variable region (409 bp) of the light chain ImAb3 was amplified with primers:

P8:
GTA ACA ACG CAG AGT ACG CGG G        (SEQ ID NO: 49)

P111:
CGT CCG AAG ATC ATA AGA TTG CTT GC (SEQ ID NO: 53)

Human light chain constant region (376 bp) was amplified using:

P15:
                                     (SEQ ID NO: 54)
CTA ACA CTC ACC CCT GTT GAA G

P113:
                                     (SEQ ID NO: 55)
GCA ATC TTA TGA TCT TCG GAC GTT CGG CGG AGG GAC

CAA GGT G

Thereby an overlapping sequence with the murine variable region of the light chain was introduced.

Both fragments were fused by PCR to generate the chimeric DNA-fragment (762 bp).

P9:  ACA ACG CAG AGT ACG CGG G       (SEQ ID NO: 56)

P15: CTA ACA CTC ACC CCT GTT GAA G (SEQ ID NO: 54)

To introduce unique restrictions site at both ends of the DNA fragment (NotI and XhoI) another PCR (Pwo, Roche) was performed using the following primers:

(SEQ ID NO: 57)
P216:   ATC AGC GGC CGC ACA ACG CAG AGT ACG CGG G (SEQ ID NO: 58)
P217:   ATC ACT CGA GCT AAC ACT CAC CCC TGT TGA AG

The DNA product was phosphorylated and cloned into EcoRV-cutted pBuescript II KS+. The DNA was sequenced, cutted by restriction enzymes NotI and XhoI and ligated into the eukaryotic expression vector pBudCE4.1 (Invitrogen, V532-20).

The variable region of the murine heavy chain ImAb3 was fused to the constant region of human IgG1 by PCR. The murine variable region of the heavy chain ImAb3 (488 bp) was first amplified with primers:

P8:
GTA ACA ACG CAG AGT ACG CGG G        (SEQ ID NO: 49)

P119:
GAC ATC GAA GTA CCA CCT ACT ACC    (SEQ ID NO: 59)

The human heavy chain constant region (1048 bp) was amplified using:

Both fragments were fused by PCR and unique restrictions sites were introduced by another PCR (HindIII at 5'-prime and XbaI at 3'-prime).

P220:ATC AAA GCT TAC AAC GCA GAG TAC GCG GGG GCG TAT G   (SEQ ID NO: 62)
P221:ATC ATC TAG ATC ATT TAC CCG GAG A-                  (SEQ ID NO: 63)
     CA GGG AGA GGC TCT TC

The final fragment (1513 bp) was cloned blunt end into EcoRV-cutted pBluescript II KS+, sequenced and cloned into pBud CE4.1 after HindIII and EcoRV digestion.

The DNA Sequence of Chimeric Light Chain ImAb3 is Shown in SEQ ID NO: 9

The Protein Sequence of Chimeric Light Chain ImAb3 is Shown in SEQ ID NO: 10

The DNA Sequence of Chimeric Heavy Chain ImAb3 is Shown in SEQ ID NO: 11

The Protein Sequence of Chimeric Heavy Chain ImAb3 is Shown in SEQ ID NO: 12

Chimeric Antibody ImAb4:

To amplify the human heavy chain genes the following primers were used:

P8:
GTA ACA ACG CAG AGT ACG CGG G        (SEQ ID NO: 49)

P16:
TCA TTT ACC CGG AGA CAG GGA GAG GC (SEQ ID NO: 52)

To amplify the light chain genes the following primers were used:

P8:   GTA ACA ACG CAG AGT ACG CGG G (SEQ ID NO: 49)

P15:  CTA ACA CTC ACC CCT GTT GAA G (SEQ ID NO: 54)

The human constant regions were amplified by specific primers and fused to the murine variable regions by the following PCR.

The murine variable region (432 bp) of the light chain ImAb4 was amplified with primers:

P8:       GTA ACA ACG CAG AGT ACG CGG G (SEQ ID NO: 49)

P118:     CGT CGG AGG AAC ATG TGT ACT TTG AGA GC (SEQ ID NO: 64)

The human light chain constant region (377 bp) was amplified using:

P15:   CTA ACA CTC ACC CCT GTT GAA G (SEQ ID NO: 54)

P114:  CAA AGT ACA CAT GTT CCT CCG ACG TTC GGC GGA GGG ACC AAG GTG (SEQ ID NO: 65)

Thereby an overlapping sequence with the murine variable region of the light chain was introduced Both fragment were fused by PCR.

P9:    ACA ACG CAG AGT ACG CGG G  (SEQ ID NO: 56)

P15:   CTA ACA CTC ACC CCT GTT GAA G (SEQ ID NO: 54)

Unique restrictions site at both ends of the DNA fragments (785 bp) were introduced by PCR using the following primers:

P116:   ATC AGC GGC CGC ACA ACG CAG AGT ACG CGG G (SEQ ID NO: 66)

P117:   ATC ACT CGA GCT AAC ACT CAC CCC TGT TGA AG (SEQ ID NO: 67)

The DNA fragment was cloned into pBluescript II KS+ (EcoRV digested) and sequenced.

After NotI and XhoI digestion the DNA was cloned into pBud CE4.1.

The murine variable region of the heavy chain ImAb4 (455 bp) was amplified with primers:

P8:    GTA ACA ACG CAG AGT ACG CGG G (SEQ ID NO: 49)

P120:  GTA GTT CAA AGT ATT TCC GTA GTT ACC (SEQ ID NO: 68)

The human heavy chain constant region (1054 bp) was amplified using:

P121:  TCA TTT ACC CGG AGA CAG GGA GAG GC (SEQ ID NO: 60)

P123:  GGT AAC TAC GGA AAT ACT TTG AAC TAC TGG GGC CAG GGA ACC CTG GTC ACC (SEQ ID NO: 69)

Both fragment were fused by PCR and unique restriction sites (HindIII at 5'-prime and XbaI at 3'-prime) were introduced.

P248:   aaa gct tAC AAC GCA GAG TAC GCG GGG (SEQ ID NO: 70)

P249:   ATC TAG ATC ATT TAC CCG GAG ACA GGG AGA G (SEQ ID NO: 71)

The final fragment (1489 bp) was cloned blunt end into EcoRV-cutted pBluescript II KS+, sequenced and cloned into pBud CE4.1 after HindIII and XbaI digestion.

The DNA Sequence of Chimeric Light Chain ImAb4 is Shown in SEQ ID NO: 13

The Protein Sequence of Chimeric Light Chain ImAb4 is Shown in SEQ ID NO: 14

The DNA Sequence of Chimeric Heavy Chain ImAb4 is Shown in SEQ ID NO: 15

The Protein Sequence of Chimeric Heavy Chain ImAb4 is Shown in SEQ ID NO: 16

Humanisation:

Adaption to the Closet Human Variable Framework:

The variable region of the chimeric antibodies was compared to human antibody variable regions on the protein level (Genbank). The closest human counterpart within consensus human genome was identified. The sequence of the murine variable region was changed outside the complementarity-determining-regions to human sequence by the introduction of point mutations on the DNA level.

LC-ImAb3 to human B3

HC-ImAb3 to human VH3-72

LC-ImAb4 to human A17

HC-ImAb4 to human VH4-59

Specific DNA-primers were used to introduce the point mutations using the QuikChange Site-Directed Mutagenesis Kit (Stratagene, Catalog #200518). The following primers in combination with its complementary primer were used to introduce single mutations.

Adaption of the Chimeric Antibody ImAb3 to Closet Human Sequence:

List of primers for light chain ImAb3 human B3

```
P61: GGG GAC ATT GTG ATG ACA CAG TCT CCA GAC TCC CTG GCT GTG TCA (SEQ ID NO: 72)
     G

P71: GTG TCA GCA GGA GAG AGG GCC ACT ATA AAC TGC AAA TCC AGT CAG (SEQ ID NO: 73)

P72: GAC ATT GTG ATG TCA CAG CCT CCA TCC TCC CTG GCT GTG         (SEQ ID NO: 74)

P73: GGG GTC CCT GAT CGC TTC TCA GGC AGT GGA TCT GGG ACA         (SEQ ID NO: 75)

P74: CTC ACC ATC AGC AGT CTG CAG GCT GAA GAC GTG GCA GTT TAT TAC (SEQ ID NO: 76)
     TGC

P91: AGA CTC CCT GGC TGT GTC ACT AGG AGA GAG GGC CAC TAT AAA CTG (SEQ ID NO: 77)
     C

P92: ACC AGC AGA AAC CAG GGC AGC CTC CTA AAC TGC TGA TCT AC      (SEQ ID NO: 78)
```

List of primers for heavy chain ImAb3 human VH3-72

```
P63:
                                                       (SEQ ID NO: 79)
CAC CAT CTC CAG AGA TGA TTC CAA AAA CAG CCT CTA

TCT TCA AAT GAA C

P75:
                                                       (SEQ ID NO: 80)
GGT ATC CAG TGT GAG GTG CAG CTG GTG GAG TCT GGA

GGA

P76:
                                                       (SEQ ID NO: 81)
CTG AGA CTC TCC TGT GCA GCT TCT GGG TTC ACC TTC

ACT

P77:
                                                       (SEQ ID NO: 82)
CGC CAG CCT CCA GGA AAG GGA CTT GAG TGG GTG GGT

TTT ATT AGA AAC

P78:
                                                       (SEQ ID NO: 83)
TAT CTT CAA ATG AAC AGC CTG AAA ACT GAG GAC AGT

GCC ACT TAT TAC TG

P93:
                                                       (SEQ ID NO: 84)
ACA TGA GCT GGG TCC GCC AGG CTC CAG GAA AGG GAC

TTG AG

P94:
                                                       (SEQ ID NO: 85)
CCT GAA AAC TGA GGA CAC TGC CGT TTA TTA CTG TGC

AAG AGA TTT CG
```

The DNA Sequence of LC-ImAb3-humB3 is shown in SEQ ID NO: 17

The Protein Sequence of LC-ImAb3-humB3 is Shown in SEQ ID NO: 18

The DNA Sequence of HC-ImAb3-humVH3-72 is Shown in SEQ ID NO: 19

The Protein Sequence of HC-ImAb3-humVH3-72 is Shown in SEQ ID NO: 20

Adaption of the Chimeric Antibody ImAb4 to Closet Human Sequence:

List of primers for light chain ImAb4 human A17

```
P67:
                                                       (SEQ ID NO: 86)
GTG ATG TTG TGA TGA CCC AAA GTC CAC TCT CCC TGC

CTG TCA G

P82:
                                                       (SEQ ID NO: 87)
CTC TCC CTG CCT GTC ACT CTT GGA CAA CCA GCC TCC

ATC TCT TGC

P83:
                                                       (SEQ ID NO: 88)
AAG CCA GGC CAG TCT CCA AGG CGC CTG ATC TAC AAA

GTT TCC

P84:
                                                       (SEQ ID NO: 89)
GGA GGC TGA GGA TGT GGG AGT TTA TTA CTG CTC TCA

AAG TAC AC

P97:
                                                       (SEQ ID NO: 90)
ACA CCT ATT TAC ATT GGT TCC AGC AGA GGC CAG GCC

AGT CTC CAA GGC

P98:
                                                       (SEQ ID NO: 91)
GAG TGG AGG CTG AGG ATG TGG GAG TTT ATT ACT GCT

CTC AAA GTA CAC ATG
```

List of primers for heavy chain ImAb4 human VH4-59

```
P65:
                                                       (SEQ ID NO: 92)
CAT CTC TCA AAA GTC GAG TCT CTA TCA GTG TAG ACA

CAT CCA AGA ACC

P79:
                                                       (SEQ ID NO: 93)
GCC TGG TGA AAC CTT CTG AGA CTC TGT CCC TCA CCT

GCA C
```

```
P80:
                                            (SEQ ID NO: 94)
AAC TGG ATC CGG CAG CCT CCA GGA AAA GGA CTG GAG

TGG ATG GGC

P81:
                                            (SEQ ID NO: 95)
TCC AAG AAC CAG TTC TCC CTG AAG TTG AGT TCT GTG

ACT ACT GAG

P95:
                                            (SEQ ID NO: 96)
GGA ACT GGA TCC GGC AGC CTC CAG GAA AGG GAC TGG

AGT GGA TGG GCT AC

P96:
                                            (SEQ ID NO: 97)
GTT GAG TTC TGT GAC TGC TGC GGA CAC AGC CGT ATA

TTA CTG TGC AAG ATT TGG

P99:
                                            (SEQ ID NO: 98)
TCC CTC ACC TGC ACT GTC TCT GGC TAC TCA ATC

P100:
                                            (SEQ ID NO: 99)
ACA AAC TGG AGT GGA TCG GCT ACA TAA GCT ACA G

P101:
                                           (SEQ ID NO: 100)
TCA AAA GTC GAG TCA CTA TCA GTG TAG ACA CAT CCA AG
```

The DNA Sequence of LC-ImAb4-humA17 is Shown in SEQ ID NO: 21.
The Protein Sequence of LC-ImAb4-humA17 is Shown in SEQ ID NO: 22
The DNA Sequence of HC-ImAb4-humVH4-59 is Shown in SEQ ID NO: 23
The Protein Sequence of HC-ImAb4-humVH4-59 is shown in SEQ ID NO: 24
Adaption to Human Variable Framework:
Two additional humanised antibodies per murine antibody were generated with less homology. Their start sequences are the previously humanised antibody ImAb3 and ImAb4.
LC-ImAb3-humB3 to human A3
HC-ImAb3-humVH3-72 to human VH3-23
LC-ImAb3-humB3 to human A17
HC-ImAb3-humVH3-23 to human VH2-26
LC-ImAb4-humA17 to human A5-1
HC-ImAb4-humVH4-59 to human VH1-3
LC-ImAb4-humA17 to human 01
HC-ImAb4-humVH4-59 to human VH4-31
For ImAb3 antibody:
List of primers for light chain ImAb3 human A3

```
P146:
                                           (SEQ ID NO: 101)
GAC ACA GTC TCC ACT CTC CCT GCC TGT GAC ACT AGG

AGA GAG GGC CAC

P151:
                                           (SEQ ID NO: 102)
CTC TCA CCA TCA GCA GAG TGG AGG CTG AAG ACG TGG C

P152:
                                           (SEQ ID NO: 103)
AGG CTG AAG ACG TGG GAG TTT ATT ACT GCA AGC

P155:
                                           (SEQ ID NO: 104)
CAG AAA CCA GGG CAG TCT CCT CAA CTG CTG ATC TAC

TGG GC

P205:
                                           (SEQ ID NO: 105)
CTT GGC TTG GTA CCT GCA GAA ACC AGG GC

P206:
                                           (SEQ ID NO: 106)
GAC ACC AGG AGA GCC GGC CTC TAT AAG CTG CAA ATC

CAG TC

P207:
                                           (SEQ ID NO: 107)
CTT GGC TTG GTA CCT GCA GAA ACC AGG GC

P242:
                                           (SEQ ID NO: 108)
GGA CAG ATT TCA CTC TCA AAA TCA GCA GAG TGG AGG

CTG
```

The DNA Sequence of LC-ImAb3-humA3 is Shown in SEQ ID NO: 25
The Protein Sequence of LC-ImAb3-humA3 is Shown in SEQ ID NO: 26
List of primers for heavy chain ImAb3 human VH3-23

```
P168:
                                           (SEQ ID NO: 109)
TGT GAG GTG CAG CTG TTG GAG TCT GGA GGA GGC

P169:
                                           (SEQ ID NO: 110)
GAC TTG AGT GGG TGA GTT TTA TTA GAA ACA AAG C

P170:
                                           (SEQ ID NO: 111)
CAT CTC CAG AGA TAA TTC CAA AAA CAC CCT CTA TCT

TCA AAT G

P171:
                                           (SEQ ID NO: 112)
AAT GAA CAG CCT GAG AGC TGA GGA CAC TGC CG

P231:
                                           (SEQ ID NO: 113)
GTT TAT TAC TGT GCA AAg GAT TTt GGT AGT AGG
```

The DNA Sequence of HC-ImAb3-humVH3 23 is Shown in SEQ ID NO: 27
The Protein sequence of HC-ImAb3-humVH3 23 is shown in SEQ ID NO: 28
List of primers for light chain ImAb3 human A17

```
P145:
                                           (SEQ ID NO: 114)
ACC TGT GGG GAC GTT GTG ATG ACA CAG TCT CC

P146:
                                           (SEQ ID NO: 115)
GAC ACA GTC TCC ACT CTC CCT GCC TGT GAC ACT AGG

AGA GAG GGC CAC

P148:
                                           (SEQ ID NO: 116)
CTA CTT GGC TTG GTT CCA GCA GAG ACC AGG GCA GCC

TCC
```

P151:
(SEQ ID NO: 117)
CTC TCA CCA TCA GCA GAG TGG AGG CTG AAG ACG TGG C

P152:
(SEQ ID NO: 118)
AGG CTG AAG ACG TGG GAG TTT ATT ACT GCA AGC

P202:
(SEQ ID NO: 119)
CTG TGA CAC TAG GAC AGC CGG CCT CTA TAA GCT GCA AAT CCA GTC AGA G

P203:
(SEQ ID NO: 120)
AGA CCA GGG CAG TCT CCT AGA CTG CGG ATC TAC TGG GCA TCC

P204:
(SEQ ID NO: 121)
CAG ATT CAC TCA AAA TCA GCA GAG TGG AGG C

The DNA Sequence of LC-ImAb3-humA17 is Shown in SEQ ID NO: 29

The protein Sequence of LC-ImAb3-humA17 is Shown in SEQ ID NO: 30

List of primers for heavy chain ImAb3 human VH2-26

P173:
(SEQ ID NO: 122)
AAT GGT ATC CAG TGT CAG GTG ACG CTGA AGG AGT CTG GAG GAG GC

P175:
(SEQ ID NO: 123)
GAC CAG TCT TGG TAA AGC CTA CGG AGA CTC TGA GAC TCT CCT G

P176:
(SEQ ID NO: 124)
CTA CGG AGA CTC TGA CAC TCA CCT GTA CAG TTT CTG GGT TCA CCT TC

P177:
(SEQ ID NO: 125)
TAC ATG AGC TGG ATC CGC CAG CCT CCA GGA AAG GGA CTT G

P178:
(SEQ ID NO: 126)
GCC TCC AGG AAA GGC ACT TGA GTG GCT GGC TTT TAT TAG AAA CAA AGC

P179:
(SEQ ID NO: 127)
TGT GAA GGG TCG GCT CAC CAT CTC AAG ATA CTT CAA AAA CAG CCT C

P181:
(SEQ ID NO: 128)
CGT TCT TAC AAT GAC CAA CAT GGA TCC TGT GGA CAC TGC CGT TTA TTA C

P182:
(SEQ ID NO: 129)
GTG GAC ACT GCC ACT TAT TAC TGT GCA AG

P246:
(SEQ ID NO: 130)
CAA AGA TAC TTC AAA ATC CCA GGT

P276:
(SEQ ID NO: 131)
CTG GAC CAG TCT TGG TAA AGC CTA CGG AGA CTC TGA GAC TCT CCT G

The DNA Sequence of HC-ImAb3-humVH2 26 is shown in SEQ ID NO: 31
The Protein sequence of HC-ImAb3-humVH2 26 is Shown in SEQ ID NO: 32

For ImAb4 antibody
List of primers for light chain ImAb4 human A5-1

P160:
(SEQ ID NO: 132)
CCT GCT TCC AGC AGT GAA ATT GTG ATG ACC CAA AGT CC

P162:
(SEQ ID NO: 133)
GTC CAC TCT CCC TGT CTA TCA CTC

P164:
(SEQ ID NO: 134)
TAT TTA CAT TGG TTC CTG CAG AAG GCA GGC CAG TCT CCA AGG C

P167:
(SEQ ID NO: 135)
GTG GAG GCT GAG GAT TTC GGA GTT TAT TAC TGC

P198:
(SEQ ID NO: 136)
ATT GTG ATG ACC CAA ACT CCA CTC TCC CTG TC

P199:
(SEQ ID NO: 137)
TCT ATC ACT CCT GGA GAA CAA GCC TCC ATC TCT TGC

P200:
(SEQ ID NO: 138)
TTC CTG CAG AAG GCA CGC CCG GTT CCA GGG CGC CTG ATC

P201:
(SEQ ID NO: 139)
CCA CGC CCG GTT CAA ACG CTC CTG ATC TAC AAA GTT TCC

The DNA Sequence of LC-ImAb4-humA5-1 is Shown in SEQ ID NO: 33
The Protein Sequence of LC-ImAb4-humA5-1 is Shown in SEQ ID NO: 34

List of primers for heavy chain ImAb4 human VH1-3

P183:
(SEQ ID NO: 140)
GGT ATC CTG TCT CAA GTG CAG CTT CAG G

P186:
(SEQ ID NO: 141)
TCA AGT GCA GCT TGT GCA GTC GGG ACC TGG CCT GG

P187:
(SEQ ID NO: 142)
CTT GTG CAG TCG GGA GCT GAA

P189:
(SEQ ID NO: 143)
GCG TCT GTG AAA GTC AGC TGC AAG GCC TCT GGC TAC TCA ATC

-continued

P190:
(SEQ ID NO: 144)
GCC TGG AAC TGG GTC CGG CAG GCT CCA GGA CAG AGA C

P191:
(SEQ ID NO: 145)
GCA GCC TCC AGG ACA GAG ACT GGA GTG GAT CG

P192:
(SEQ ID NO: 146)
AGA GAC TGG AGT GGA TGG GCT ACA TAA GCT AC

P193:
(SEQ ID NO: 147)
GTC GAG TCA CTA TCA CTA GAG ACA CAT CCA AGA ACC

P194:
(SEQ ID NO: 148)
ATC ACT AGA GAC ACA TCC GCG AGC ACG GCC TAC ATG GAG TTG AG

P195:
(SEQ ID NO: 149)
AAG AAC CAG TTC TAC ATG GAG TTG AGT TCT CTG

P196:
(SEQ ID NO: 150)
GAA GTT GAG TTC TCT GAG ATC TGA GGA CAC AGC CGT ATA TT

P197:
(SEQ ID NO: 151)
TGA GAT CTG AGG ACA TGG CCG TAT ATT ACT G

P244:
(SEQ ID NO: 152)
CTG GCC TGG TGA AAC CTG GTG CGT CTG TGA AAC TCA CCT GCA CTG TCT CTG

The DNA Sequence of HC-ImAb4-humVH1-3 is Shown in SEQ ID NO: 35
The Protein Sequence of HC-ImAb4-humVH1-3 is Shown in SEQ ID NO: 36

List of primers for light chain ImAb4 human O1

P156:
(SEQ ID NO: 153)
CTT CCA GCA GTG ATA TTG TGA TGA CCC AAA CTC CAC TCT CCC TGC C

P157:
(SEQ ID NO: 154)
CTG CCT GTC ACT CCT GGA GAA CCA GCC TCC ATC TCT TGC

P158:
(SEQ ID NO: 155)
CCT ATT TAC ATT GGT ACC TGC AGA AGC CAG GCC AGT CTC C

P159:
(SEQ ID NO: 156)
CAG GCC AGT CTC CAC AGC TCC TGA TCT ACA AAG TTT CC

The DNA Sequence of LC-ImAb4-humO1 is shown in SEQ ID NO: 37
The Protein Sequence of LC-ImAb4-humO1 is Shown in SEQ ID NO: 38

List of primers for heavy chain ImAb4 human VH4-31

P183:
(SEQ ID NO: 157)
GGT ATC CTG TCT CAA GTG CAG CTT CAG G

P184:
(SEQ ID NO: 158)
GTG AAA CCT TCT CAG ACT CTG TCC CTC

P185:
(SEQ ID NO: 159)
TGG ATC CGG CAG CAT CCA GGA AAG GG

The DNA Sequence of HC-ImAb4-humVH4-31 is Shown in SEQ ID NO: 39
The Protein Sequence of HC-ImAb4-humVH4-31 is Shown in SEQ ID NO: 40

Primers for Heavy Chain IMAB1

P22:
(SEQ ID NO: 262)
CCC ACT ACC TCC ACC TCC AGA GCC TCC CCC TCC TGC AGA GAC AGT GAC CAG AGT C

P18:
(SEQ ID NO: 263)
AGT GAT GAG CAC TGA ACA CAG A

HEAVY CHAIN ImAB1 DNA sequence, $V_H$
The DNA sequence of HC ImAB1 $V_H$ is shown in SEQ ID NO: 42.
HEAVY CHAIN ImAB1 Protein sequence, $V_H$
The protein sequence of HC ImAB1 $V_H$ is shown in SEQ ID NO: 44.

| | |
|---|---|
| signal peptide: | 1-19 |
| variable chain: | 20-133 |
| CDR1 | 45-54 |
| CDR2 | 69-84 |
| CDR3 | 117-122 |

Primers for LIGHT CHAIN ImAb1

P25:
(SEQ ID NO: 260)
TCT GGA GGT GGA GGT AGT GGG GGA GGA GGT TCA GAC ATC AAG ATG ACC CAG TCT C

P28:
(SEQ ID NO: 261)
GGC CTA ATC GGC CCG TTT TAT TTC CAG CTT GGT C

LIGHT CHAIN ImAB1 DNA sequence, $V_L$
The DNA sequence of said light chain is shown in SEQ ID NO: 41.
LIGHT CHAIN ImAB1 Protein sequence, $V_L$
The protein sequence of said light chain is shown in SEQ ID NO: 43.

| | |
|---|---|
| signal peptide: | 1-17 |
| variable kappa chain: | 18-128 |
| CDR1 | 46-56 |
| CDR2 | 72-78 |
| CDR3 | 111-119 |

Primers for Heavy chain ImAb5

P21:
(SEQ ID NO: 266)
GAC CTG TCA CCA TGA AGT TGT G

P24:
(SEQ ID NO: 267)
CCC ACT ACC TCC ACC TCC AGA GCC TCC CCC TCC TGA

GGA GAC GGT GAC CGT GG

HEAVY CHAIN ImAB5 DNA sequence, $V_H$
The DNA sequence of said heavy chain is shown in SEQ ID NO: 46.
HEAVY CHAIN ImAB5 protein sequence, $V_H$
The protein sequence of said heavy chain is shown in SEQ ID NO: 48.

| signal peptide: | 1-19 |
| variable chain: | 20-140 |
| CDR1 | 45-54 |
| CDR2 | 69-87 |
| CDR3 | 120-129 |

Primers for light chain ImAb5

P26:
(SEQ ID NO: 264)
TCT GGA GGT GGA GGT AGT GGG GGA GGA GGT TCA GAC

ATT GTG ATG TCA CAG TCT CC

P29:
(SEQ ID NO: 265)
GGC CTA ATC GGC CCG TTT GAT TTC CAG CTT GGT G

LIGHT CHAIN ImAB5 DNA sequence, $V_L$
The DNA sequence of said light chain is shown in SEQ ID NO: 45.
LIGHT CHAIN ImAB5 Protein sequence, $V_L$
The protein sequence of said light chain is shown in SEQ ID NO: 47.

| signal peptide: | 1-20 |
| variable kappa chain: | 21-133 |
| CDR1 | 44-60 |
| CDR2 | 76-82 |
| CDR3 | 115-122 |

The DNA constructs of the mutated antibodies were fully sequenced and liberalized by PvuI digestion. The DNA was purified from an agarose gel, extracted with Phenol/Chloroform and precipitated with ethanol. DNA was transfected into CHO cells and the antibodies purified from the supernatants by affinity purification.

B. Specificity of the Antibodies (Test for Crossreactivity with Other Family Member; Different Species)

i. Cross-Reactivity with Other Family Members

In order to analyse cross-reactivity of anti-Eag1 antibodies of the invention with the most homologous Eag family member Eag2 a BIAcore™ binding analysis was performed. BIAcore chips were coated with Eag1 C-terminus (amino acids 694 to 962), the H5 region (amino acids 374 to 452) or Eag2 (the equivalent regions fused in a single construct). The interaction with anti-Eag1 antibodies ImAb1 and ImAb3 were analysed using 10 μg/ml antibody at a flow rate of 20 μl/min.

Figure 2:
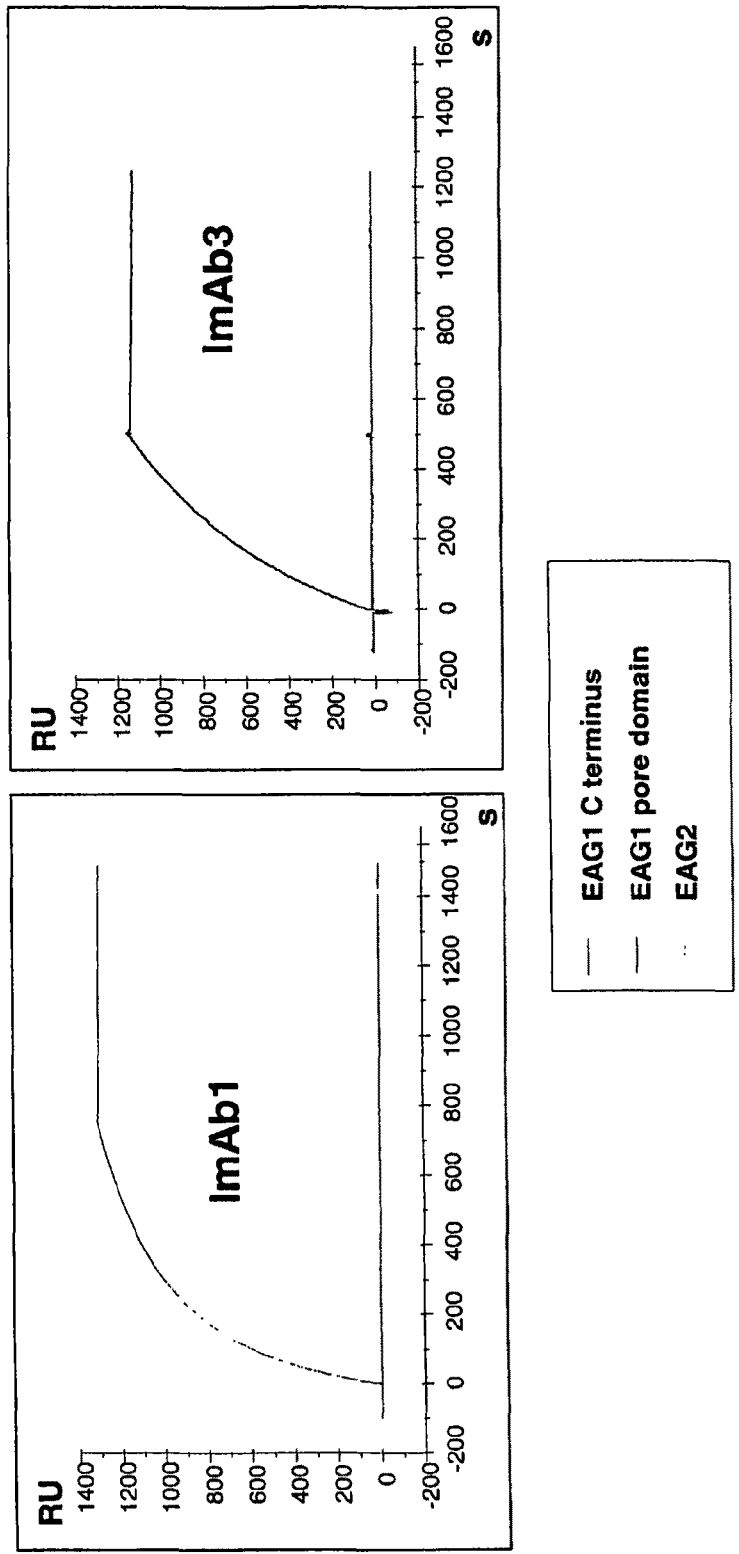

The result as indicated in FIG. 2 show that both anti-Eag1 antibodies of the invention are selective for the Eag1 antigen and do not cross-react with Eag2. In addition, the results demonstrate that ImAb1 specifically binds to the C-terminus of the Eag1 antigen, whereas ImAb3 specifically recognizes the pore domain of Eag1.

ii. Cross-Reactivity with Different Species

Figure 3:
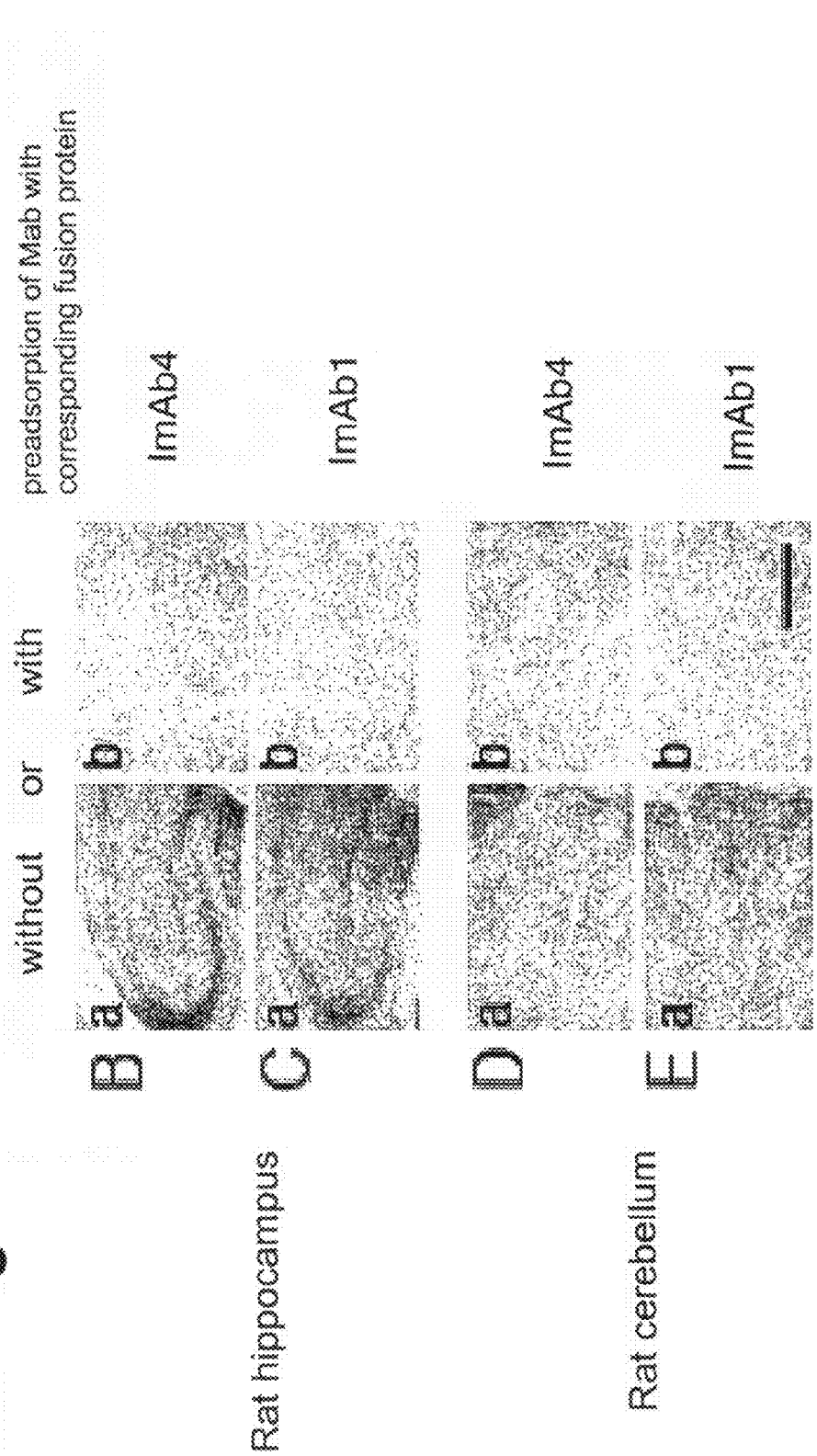

Cross-reactivity of anti-Eag1 antibodies of the invention were further analysed by Immunohistochemistry studies of rat brain sections of the cerebellum and the hippocampus. For the IHC, two postnatal-day 21 Sprague Dawley rats were anesthetized with a mixture of ketamine HCl (Ketaset; 100 mg/ml; Fort Dodge Laboratories, Inc., U.S.A.) and xylazine (Rompun; 20 mg/ml; Mile, Inc., U.S.A.) at 0.1 ml/100 g body weight. The animals were transcardially perfused with a fixative consisting of 4% p-formaldehyde in 0.12 M phosphate buffer (pH 7.2). After perfusion, brains were removed, fixed for an additional hour at 4° C., rinsed three times with PBS and stored overnight at 4° C. Coronal and sagital sections (40-50 μm) were cut in cold PBS using a vibratome (Leica, Vienna, Austria). Slices were incubated for 1 h with 10% normal goat serum in PBS, then with anti-Eag1 antibodies ImAb1 (4 μg/ml) and ImAb4 (2 μg/ml) in PBS overnight at 4° C. and processed using the avidin/biotin-peroxidase system (Vectastain kit, Vector Laboratories, Burlingame, Calif.). Antibody binding was visualized using 3'-3-diaminobenzidine tetrahydrochloride (DAB; DAB substrate kit for peroxidase, Vector Laboratories). Controls were done by either omitting the primary antibody or by prior incubation of the primary antibody with the corresponding fusion protein (10 μg/ml final concentration) at 4° C. for 24 h and then following the procedure as described above. Sections were analysed with a Zeiss Axiophot microscope. The results as indicated in FIG. 3 demonstrate that anti-Eag1 antibodies of the invention not only recognizes human Eag1, but also cross-reacts with other mammalian species such as rat.

Example 3

Epitope Mapping 76 overlapping peptides (each 13 mer long; shift 2 aminoacids; spanning the same aa as the immunogen recombinant protein) were synthesized and covalently bound to a Whatman 50 cellulose support (SPOT membrane custom synthesized, Jerini A G).

Peptide sequences was: 1. MHHHHHHSSGMGD, 2. HHHHHSSGMGDYE, 3. HHHSSGMGDYEIF, 4. HSSGMGDYEIFDE, 5. SGMGDYEIFDEDT, 6. MGDYEIFDEDTKT, 7. DYEIFDEDTKTIR, 8. EIFDEDTKTIRNN, 9. FDEDTKTIRNNSW, 10. EDTKTIRNNSWLY, 11. TKTIRNNSWLYQL, 12. TIRNNSWLYQLAM, 13. RNNSWLYQLAMDI, 14. NSWLYQLAMDIGT, 15. WLYQLAMDIGTPY, 16. YQLAMDIGTPYQF, 17. LAMDIGTPYQFNG, 18. MDIGTPYQFNGSG, 19. IGTPYQFNGSGSG, 20. TPYQFNGSGSGKW, 21. YQFNGSGSGKWEG, 22. FNGSGSGKWEGGP, 23. GSGSGKWEGGPSK, 24. GSGKWEGGPSKNS, 25. GKWEGGPSKNSVY, 26. WEGGPSKNSVYIS, 27. GGPSKNSVYISSL, 28. PSKNSVYISSLYF, 29. KNSVYISSLYFTM, 30. SVYISSLYFTMTS, 31. YISSLYFTMTSLT, 32. SSLYFTMTSLTSV, 33. LYFTMTSLTSVGF, 34. FTMTSLTSVGFGN, 35. MTSLTSVGFGNIA, 36. SLTSVGFGNIAPS, 37. TSVGFGNIAPSTD, 38. VGFGNIAPSTDEI, 39. FGNIAPSTDIEKI, 40. NIAPSTDIEKIFL, 41. APSTDIEKIFLES, 42. STDIEKIFLESPQ, 43. DIEKIFLESPKDR, 44. EKIFLESPKDRSP, 45. IFLESP- KDRSPIL, 46. LESPKDRSPILAE, 47. SPQDRSPILAEVK, 48. QDRSPILAEVKHS, 49. RSPILAEVKHSFY, 50. PILAEVKHSFYPI, 51. LAEVKHSFYPIPE, 52. EVKHSFYPIPEQT, 53. KHSFYPIPEQTLQ, 54. SFYPIPEQTLQAT, 55. YPIPEQTLQATVL, 56. IPEQTLQATVLEV, 57. EQTLQATVLEVRH, 58. TLQATVLEVRHEL, 59. QATVLEVRHELKE, 60. TVLEVRHELKEDI, 61. LEVRHELKEDIKA, 62. VRHELKEDIKALN, 63. HELKEDIKALNAK, 64. LKEDIKALNAKMT, 65. EDIKALNAKMTNI, 66. IKALNAKMTNIEK, 67. ALNAKMTNIEKQL, 68. NAKMTNIEKQLSE, 69. KMTNIEKQLSEIL, 70. TNIEKQLSEILRI, 71. IEKQLSEILRILT, 72. KQLSEILRILTSL, 73. LSEILRILTSLEH, 74. EILRILTSLEHHH, 75. LRILTSLEHHHHH, 76. RILTSLEHHHHHH;

The above peptides are shown in the sequence listing with SEQ ID NOs 184 to 259, respectively.

The membrane was rinsed in ethanol, washed three times with TBS and blocked with 3% BSA in TBS overnight at room temperature with shaking. The membrane was then washed once with the same volume of T-TBS for 10 min. and incubated for 3 hours, with shaking, with the desired primary anti-Eag1 antibody. ImAb1-5 were diluted 1:2000 (from 1 mg/ml stock solution in PBS). The primary antibody was then discarded and the membrane was washed three times with TBST for 10 min.

The membrane was then incubated with an appropriate volume of HRP-conjugated secondary antibody solution for 2 hours with shaking. Anti-mouse HRP antibody was diluted 1:5000 in blocking buffer, washed three times with the same volume of T-TBS for 10 min, incubated with detection reagent—ECL solution for 1 min with gentle shaking and developed.

The appearance of a number of dark spots on the film represented a positive signal where each spot corresponded to one of the 76 peptides.

ImAb4 bound at spots 3-8

ImAb3 and ImAb2 behaved equivalently and bound to spots 21 to 24 (strong signal) and spots 3-7 (weak signal);

ImAb5 bound to spots 21-24 (FIG. 4).

Each of these peptides are localized within the pore domain region of Eag1.

ImAb1 bound weakly to peptides 21-24 (pore domain; FIG. 4). This antibody, however, should recognize mainly CAD domain region because ImAb1 was raised against fusion protein containing CAD domain part of Eag1. That this was not observed is most likely due to the discontinuous (3-D) nature of the corresponding epitope All the results are summarized in the Table 1. Similarity of the epitopes among ImAbs 2, 3 and 5 were not surprising since the corresponding antibodies were raised using the same fusion protein that contain only a part of EAG1. Surprising was only the result obtained with ImAb1 which, as discussed above, was probably due to the 3D nature of the epitope.

Example 4

Determination of Internalization of Anti-Eag1 Antibodies of Invention

In order to analyse the internalization properties of the anti-Eag1 antibodies of invention, CHO cells were grown on coverslips and incubated in normal medium (Ham's F12, 10% FCS) overnight (37 C, 5% $CO_2$) with anti-Eag1 antibodies ImAb1 and ImAb4 directly labeled with Cy3 (100 μg).

Figure 5:
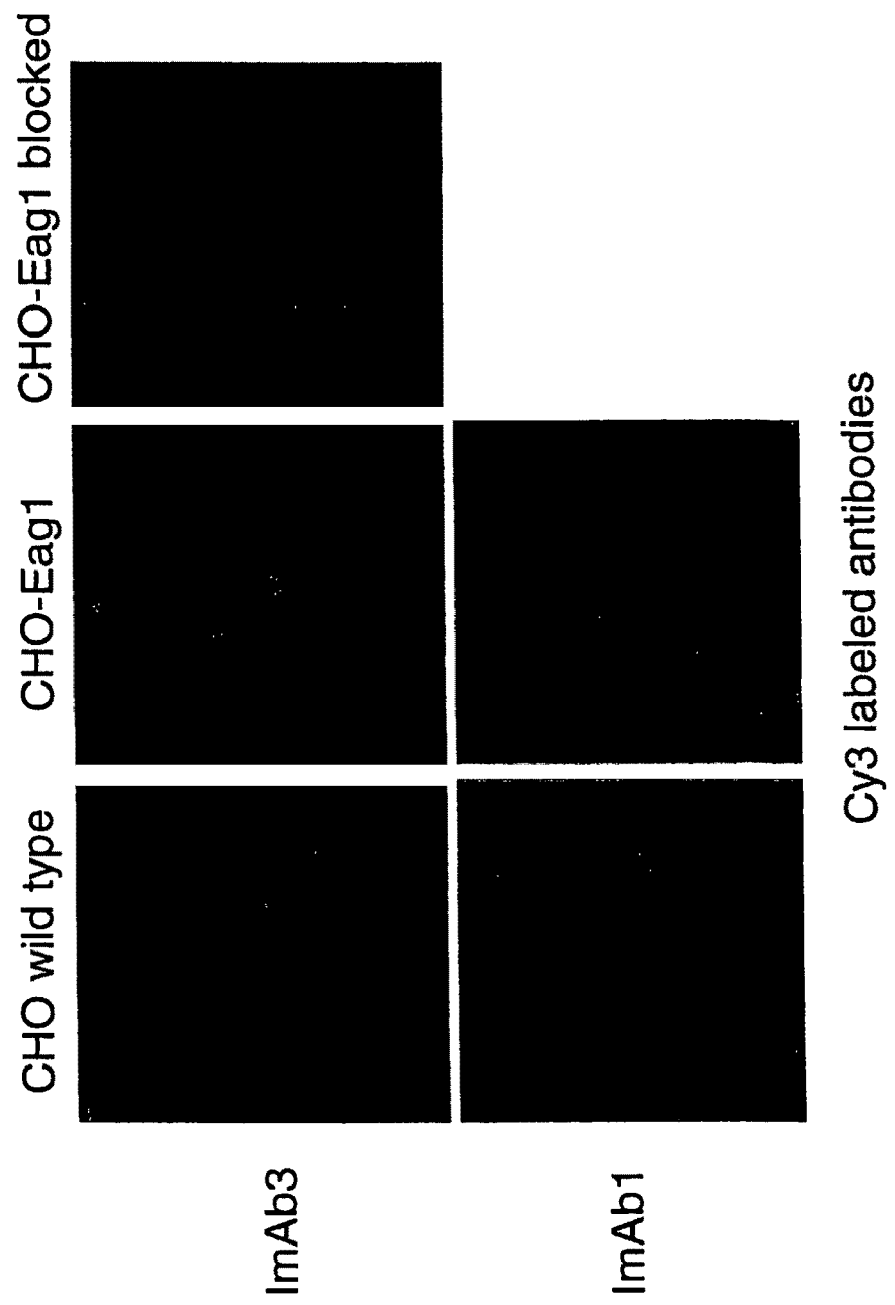
FIG. 5 shows an immunofluorescence experiment with Cy3-labelled anti-Eag1 antibodies ImAb1 and ImAb3 on living Eag1 overexpressing CHO K1 cells. The result demonstrates that both Cy3-labelled anti-Eag1 antibodies of the invention, which recognizes different epitopes, bind to Eag1 antigen on living CHO-Eag1 cells and internalize into the cells.

Cultures were thereafter incubated with app. 2 μg/ml Hoechst 33342 for 10 min. After washing, cells were observed in vivo using a 63× water immersion objective in a standard fluorescence microscope (Zeiss Axiophot). The result as indicated in FIG. 5 shows that both anti-Eag1 antibodies of the invention bind to Eag1 antigen on living cells expressing the antigen and are internalized into the cells within 24 h. It is demonstrated, that ImAb4, which recognizes the extracellular core domain, as well as ImAb1, which binds to an intracellular epitope at the C-terminus of the Eag1 antigen, are both internalized into Eag1-expressing cells.

Example 5

Determination of Blocking Properties of Anti-Eag1 Antibody of Invention

Figure 6:
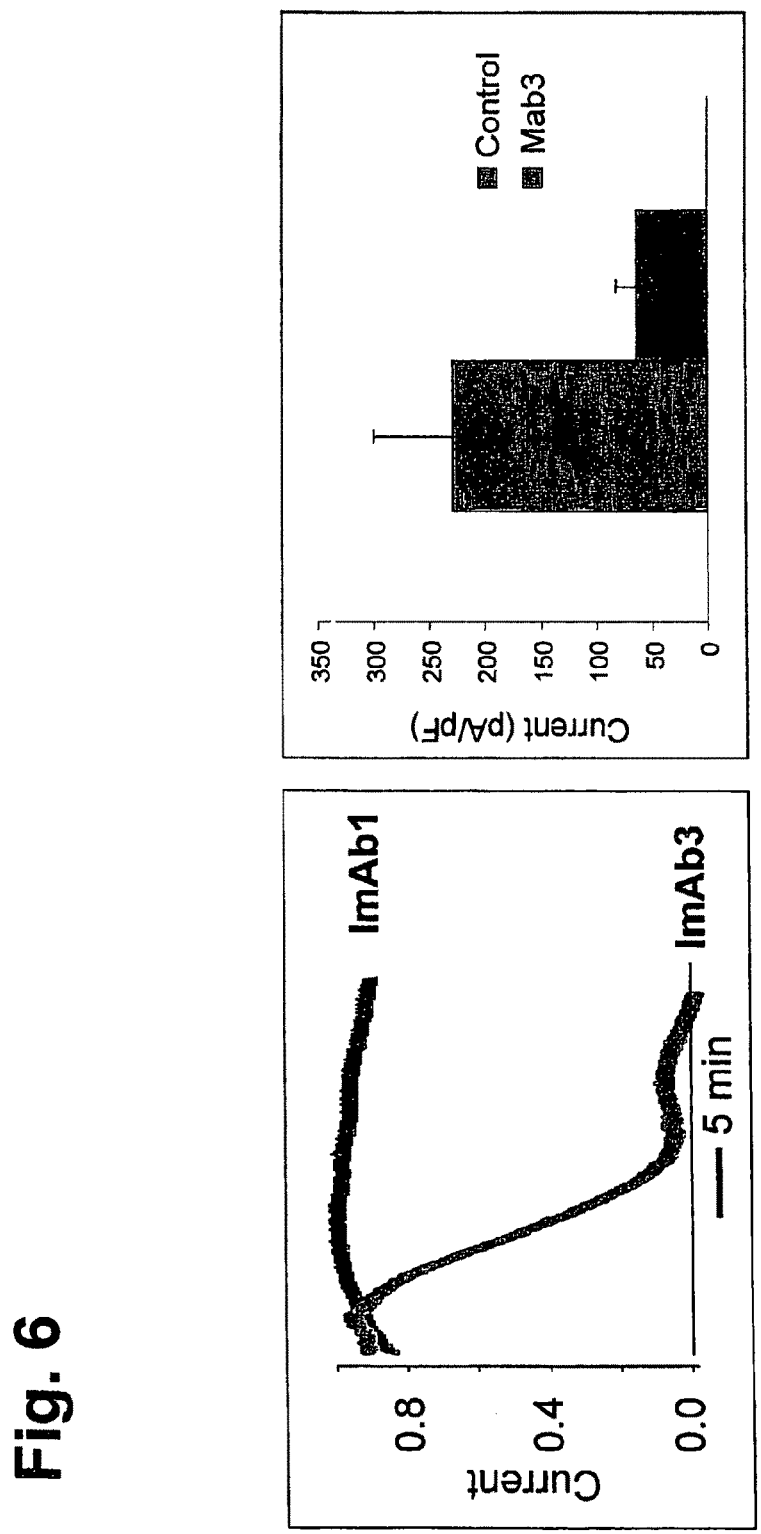
FIG. 6 shows the inhibition of Eag1 current in Eag1-expressing oocytes by treatment with hybridoma supernatants of mouse monoclonal anti-Eag1 antibody ImAb3 and the ability of ImAb3 to block Eag1 current in Eag1 expression CHO cells.
Figure 7:
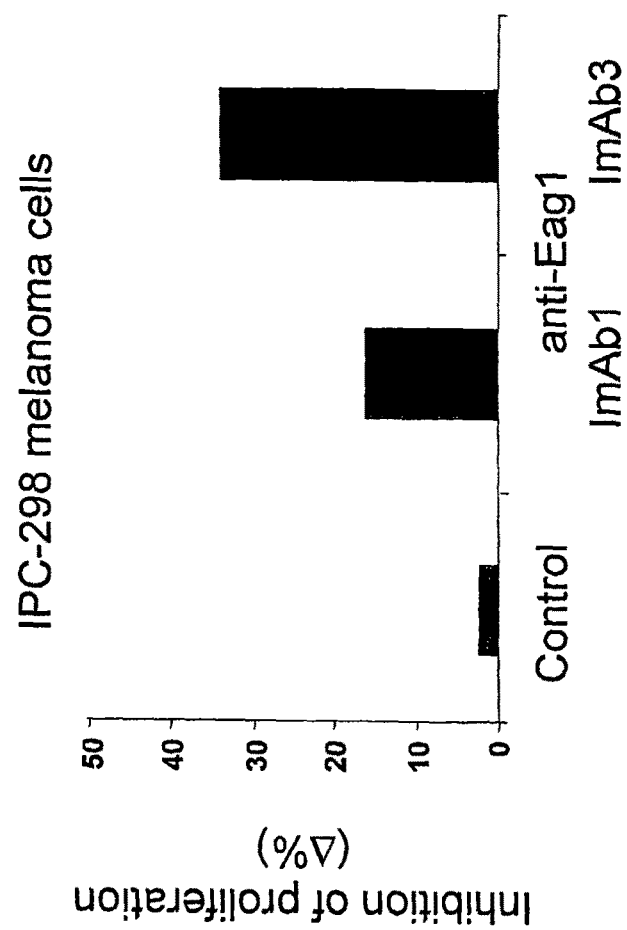
FIG. 7 shows the inhibition of IPC-298 melanoma cell proliferation by mouse anti-Eag1 antibodies ImAb1 and ImAb3 of the invention. Said antibodies inhibit basal cell growth in human cancer cells.

In order to analyse the functional properties of anti-Eag1 antibodies of the invention were analysed by a two-electrode voltage clamp experiment. Therefore, Oocyte preparation and electrophysiological recordings were performed as described in Stühmer, W., 1992, *Methods in Enzymology* 207. Oocytes were injected with synthetic mRNA coding for Eag1, incubated for 48 h and recorded in NFR (115 mM NaCl, 1.8 $CaCl_2$, 2.5 KCl, 10 Hepes pH 7.2) until stable traces were recorded. Then, 10% of the corresponding hybridoma supernatant producing ImAb1 or ImAb3 was added to the chamber and current amplitudes were further monitored. The result as indicated in FIG. 6 (left) shows that hybridoma supernatant of mouse monoclonal anti-Eag1 antibody ImAb3 possesses the ability to block Eag1 current in Eag1-expressing Oocytes. No inhibition of Eag1 current was detected using hybridoma supernatant of ImAb1.

In addition, a two-electrode voltage clamp experiment was performed using CHO cells stably expressing Eag1, which were incubated for three hours with 100 μg ImAb 3 in the presence of 40 mM KCl. Cells were then recorded and total current amplitude was normalized for cell surface using the automatic capacity compensation of the EPC9 amplifier. The results as indicated in FIG. 6 (right) shows that anti-Eag1 antibody of the invention inhibits Eag1 current in Eag1-overexpressing CHO cells.

Example 6

Inhibition of IPC-298 Cell Proliferation by Anti-Eag1 Antibodies of the Invention In vitro experiments were conducted in order to determine the ability of the antibodies of the invention to inhibit cancer cell proliferation. 1000 IPC-298 cells were seeded in 60 μl/well 10% FCS-containing medium (DMEM 4500 mg/ml glucose) on 96-well plates overnight. Cells were pre-incubated in quadruplicates with 5 μg/ml anti-Eag1 monoclonal antibodies, ImAb1 and ImAb3, diluted in FCS-containing medium with 40 mM KCl for 1 h at 37° C. in 5% $CO_2$. Treatment of the cells with 40 mM KCl ensures an open conformation of the ion channel Eag1 and might accelerate binding of the monoclonal anti-EAG1 antibodies to its corresponding epitope. After 1 h incubation, supernatants were removed and replaced with 100 μl/well FCS-containing medium with 5 μg/ml anti-Eag1 antibodies, ImAb1 and ImAb3. Cells were then incubated at 37° C. in 5% $CO_2$ for 7 days. In order to assess proliferation and cell viability 10 μl/well AlamarBlue™ (BIOSOURCE) was added and incubated at 37° C. in the dark. Absorbance was measured using a spectrofluorometer at 590 nm every 30 min. The results as Example 7

Inhibition of IPC-298 Cell Proliferation by Secondary Immunotoxin-Labelled Anti-Eag1 Antibodies of the Invention In order to evaluate the specific suitability and efficacy of anti-Eag1 monoclonal antibodies for conjugation as primary immunotoxin, in vitro cell proliferation assays were performed in the presence of anti-Eag1 antibody in conjunction with a secondary antibody conjugated to saporin, a ribosome-inactivating protein from the seeds of the plant *Saponaria officinalis*. The secondary immunotoxin binds to the anti-Eag1 antibody is internalized into the cell alongside the primary antibody. Once the immunotoxin is internalised, saporin breaks away from the targeting agent and inactivates the ribosomes, which causes protein inhibition and, ultimately, cell death.

For the assay (FIG. 8a) 3000 IPC-298 cells were seeded in 60 µl/well FCS-containing medium on 96-well plates overnight. 100 ng/well (1 ng/µl) Mab-ZAP was mixed with 10 ng/µl of mouse monoclonal anti-Eag1 antibodies ImAb1 or ImAb4 in 40 µl FCS-containing medium for 1 h at 37° C. and then directly added to the cells in quadruplicates. As a control Mab-ZAP was added together with mouse monoclonal control antibody or IgG-SAP was used either alone or in combination with ImAb1. Cells were then left to grow for 72 hours at 37° C. in 5% $CO_2$. In order to assess proliferation and cell viability 20 µl/well CellTiter 96® $AQ_{ueous}$ One Solution reagent (Promega) containing the tetrazolium salt MTS and the electron coupling reagent phenazine methosulfate (PMS) was added and incubated at 37° C. for color generation and incubated for 14 hours. The quantity of formazan product was measured by the amount of 490 nm absorbance using an ELISA plate reader.

Figure 8B:
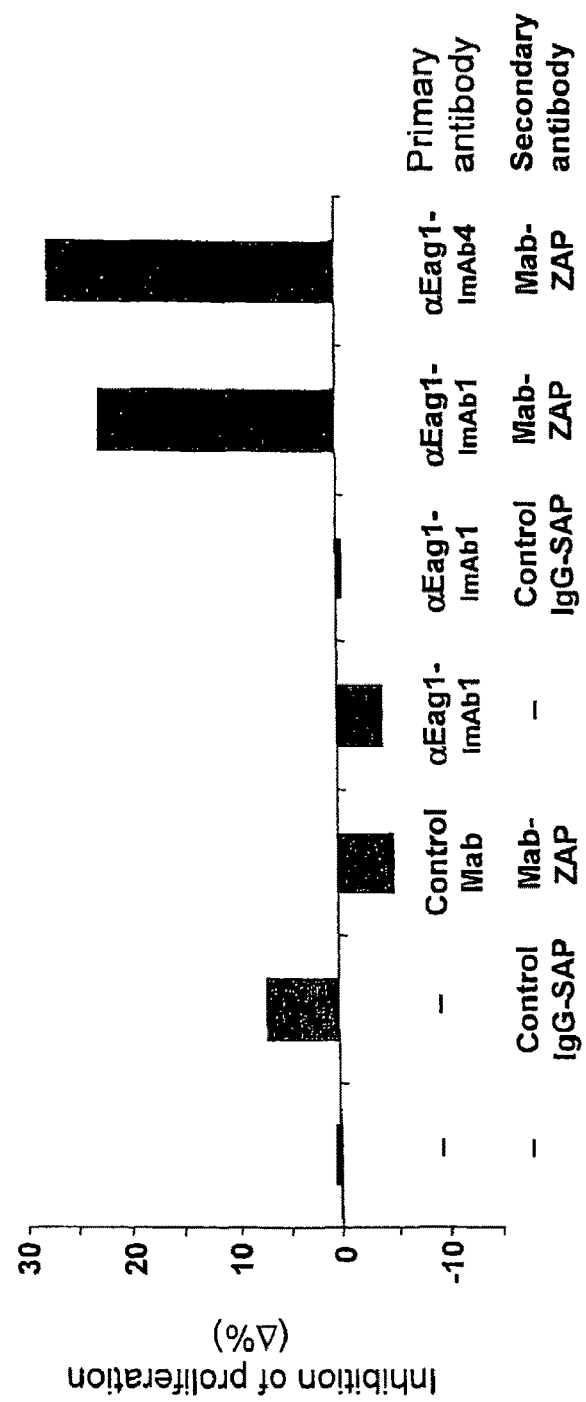

For the assay shown in FIG. 8b 3000 IPC-298 cells were seeded in 60 µl/well FCS-containing medium on 96-well plates overnight. 100 ng/well (1 ng/µl) Mab-ZAP, a chemical conjugate of affinity-purified goat anti-mouse IgG and saporin (Advanced Targeting System) was pre-incubated with different concentrations of mouse monoclonal anti-Eag1 antibody ImAb4 (10 ng/µl, 5 ng/µl, 1 ng/µl, 0.5 ng/µl, 0.1 ng/µl) in 40 µl FCS-containing medium for 1 h at 37° C. and then added directly to the cells in quadruplicates. As a control pre-immune goat IgG antibody conjugated to saporin (IgG-SAP, Advanced Targeting System) was used either alone or in combination with ImAb4. Cells were then left to grow for 72 hours at 37° C. in 5% $CO_2$. In order to assess proliferation and cell viability 10 µl/well AlamarBlue™ (BIOSOURCE) was added and incubated at 37° C. in the dark. Absorbance was measured using a spectrofluorometer at 590 nm every 30 min.

The results as indicated in FIGS. 8a and b show that the antibodies of the invention are internalised into the cells and that the secondary immuntoxin-labelled ("piggybacked") anti-Eag1 monoclonal antibodies of the invention inhibits human cancer cell growth. The potency of cell growth inhibition depends on the relation of primary antibody to secondary immunotoxin. In summary, this result demonstrates that an armed anti-Eag1 antibody of the invention provides a tool to inhibit human cancer cell growth.

Example 8

Inhibition of Anchorage Independent Cancer Cell Growth by Secondary Immunotoxin-Labelled Anti-Eag1 Antibody of the Invention Soft agar assays were conducted in order to investigate the ability of immunotoxin-labelled antibodies of the invention to inhibit anchorage independent cell growth. 100 pg Mab-ZAP, a chemical conjugate of affinity-purified goat anti-mouse IgG and saporin (Advanced Targeting System) was pre-incubated with 2.5 ng anti-Eag1 antibody ImAb 4 in OptiMEM (Gibco) containing 20 mM KCl at 4° C. for 30 min. For comparison Mab-ZAP was pre-incubated with 2.5 ng control IgG. After 30 min pre-incubation, 2000 IPC-298 cells in OptiMEM with 20 mM KCl were added and further incubated at 37° C. for 30 min. IPC-298 cells, pre-incubated with immunotoxin-labelled anti-EAG1 antibody, were resuspended in 50 µl/well 0.25% Difco noble agar containing OptiMEM with 0.5% FCS and plated on 50 µl/well 0.5% agarose underlayer containing OptiMEM with 0.5% FCS in quadruplicates. Additionally, 50 µl/well 0.25% feeding agar containing OptiMEM with 0.5% FCS was plated. Colonies were allowed to form for 10 days and were stained with 50 µl MTT (1 mg/ml in PBS) for 1.5 hours. Wells were scanned using an Epson scanner and colonies were counted using the Scion Image software. The result as indicated in FIG. 9 demonstrates that anti-Eag1 antibody ImAb4 labelled ("piggybacked") with a secondary immunotoxin inhibits anchorage independent tumor cell growth.

Example 9

Use of Anti-Eag1 Antibodies of the Invention as a Diagnostic Agent

Detection of Eag1 antigen in a sample by Immunofluorescence:

For detection of Eag1 antigen in human tumor cells an Immunofluorescence staining protocol was established. Glass-Chamber slides (Falcon) were pre-coated with 300 µl medium containing 10% FCS at 37° C. for 30 min. 40 000 MCF7 breast cancer cells/well and 40 000 IPC-298 melanoma cells/well were seeded on pre-coated glass chamber slides and cultured at 37° C. in 5% $CO_2$ for 24 h. After removing the chambers, slides were washed with PBS and cells were fixed with 4% Paraformaldehyd (in PBS adjusted to pH 7.5 with 1 M NaOH) at 25° C. for 10 min. Slides were air dried and re-hydrated with PBS for 3 min (3×). Cells were permeabilized with 0.5% Triton-X 100 in PBS for 10 min at 25° C., slides were washed for 3 min in PBS (3×) and each well was blocked with 100 µl blocking buffer (5% FCS, 2.5% BSA in PBS) at 25° C. for 1 hours. 2 µg/ml anti-EAG1 antibody ImAb 4 diluted in 40 µl blocking buffer/well was incubated for 1 h at 25° C., washed 3× with PBS and 50 µl Alexa 546 goat anti-mouse IgG (Molecular Probes; diluted 1:200 in dilution buffer) was incubated as detection antibody for 1 h at 25° C. Slides were washed with PBS (3×), 50 µl DAPI (Roche; diluted 1:1000 in PBS) was added to each well and incubated at 25° C. for 5 min. Slides were washed with $H_2O$, treated with Fluoromount G (Southern Biotechnology Associates) and stored at 4° C. in the dark.

Staining of the anti-EAG1 antigen with ImAb 4 was analysed using a Fluorescence microscope at 573 nm.

The Immunofluorescence in FIG. 10a shows that the anti-Eag1 antibody ImAb4 of the invention binds to endogenous Eag1 antigen in human cancer cells. The results indicate that the anti-Eag1 antibody of invention preferentially binds to dividing human cancer cells (in a certain stage of mitosis) and shows that anti-Eag1 antibody ImAb4 provides a diagnostic tool for detection of anti-Eag1 antigen in proliferating human cancer cells.

Example 10

Use of Anti-Eag1 Antibodies of the Invention as a Diagnostic Agent

A. Detection of EAG1 Antigen in a Sample by ELISA

An Enzyme-linked Immunosorbant Assay (ELISA) for the detection of Eag1 antigen in a sample was developed. In the assay, wells of a microtiter plate, such as a 96-well microtiter plate, were adsorbed for several hours with a mixture of 2 mouse monoclonal antibodies directed against the Eag1 antigen. The immobilized antibodies served as capture antibodies for any of the Eag1 antigen that may be present in the test sample. The wells were rinsed and treated with a blocking agent such as albumin to prevent non-specific absorption of the analyte.

Subsequently the wells were treated with lysates of human tumor cells suspected of containing the Eag1 antigen or with lysates of Chinese hamster ovary (CHO) cells stably expressing the human Eag1 antigen or with lysates of non-transfected CHO K1 cells. After rinsing away the samples, the wells were incubated with a second rabbit polyclonal anti-Eag1 antibody. After rinsing away excess second antibody, the wells were incubated with a goat anti-rabbit Abs conjugated to horseradish peroxidase (HRP), which served as a detection antibody. After rinsing, the wells were treated with a suitable chromogenic substrate and the color generation was measured using an ELISA plate reader. The results show, that this ELISA assay provides a highly specific and very sensitive assay for the detection of Eag1 antigen in a test sample.

The samples (cell lysates) for detection of Eag1 were prepared as follows: Cells (CHO K1, CHO Eag1 clone 1, IPC-298 melanoma and PC3 prostate cancer cells) were seeded in culture dishes (10 cm, Nunc). Cells were cultured for 24 h at 37° C. in 5% $CO_2$ using their corresponding medium (DMEM F12 medium for CHO cells, DMEM 4500 mg/ml glucose for IPC-298 cells, Hams F12 medium for PC3 cells) supplemented with 10% FCS or 7% FCS(PC3 cells) (Sigma). Medium was removed and cells were lysed in 750 µl lysis buffer (150 mM NaCl, 50 mM Hepes pH 7.5), 10% Glycerin, 5 mM EDTA pH 8.0, 1% Triton-X 100, 20 mM sodium pyrophosphate, 10 µg/ml aprotinin, 1 mM PMSF, 2 mM sodium orthovanadate, 100 mM NaF). Lysates were cleared by centrifugation (4° C., 13000 rpm, 10 min). Protein concentration was determined using a protein determination kit (Pierce) according the manufacture's instruction.

The sandwich ELISA for detection of Eag1 in human tumor cell lysates was performed as follows: 100 µl of capture anti-Eag1 antibodies ImAb1 and ImAb4 at a concentration of 1 µg/ml each in PBS were coated on ELISA microtiter plates (Nunc Maxisorp). After incubation at 4° C. overnight, the plates were treated with 150 µl of blocking buffer (0.5% BSA in PBS) with gently agitation for 4-6 h at 4° C. The plates were washed (3×) using 0.05% Tween 20 in PBS (washing buffer). The plates were incubated with cell lysates (100 µg protein concentration) overnight at 4° C., washed with washing buffer (3×) and then incubated with 100 µl/well of rabbit polyclonal anti-EAG1 detection antibody (iOnGen) diluted 1:1000 in dilution buffer (0.5% BSA, 0.05% Tween 20, 5 mM EDTA in PBS) for 2 h at 25° C. After washing the plates were incubated with 100 µl HRP-conjugated goat-anti rabbit IgG (0.2 µg/ml in dilution buffer) for 30 min at 25° C., washed as before, and then treated with a suitable chromogenic substrate and the color generation was measured using an ELISA plate reader (FIG. 10b).

B. Detection of EAG Antigen in IHC

Tissues from the tissue register Klinikum Kassel were analysed by immunohistochemistry in order to investigate the ability of an EAG1 antibody of the invention to stain EAG1 protein in paraffin embedded tissues. The use of fixed tissue was approved by the review board of the Klinikum Kassel. Tissue was fixed for 16 to 20 hours in 4% neutral buffered formalin and then embedded in paraffin. With a microtome 2-4 µm thin sections of selected tissue blocks were cut, mounted on silanized glass slides (Sigma) and dried at 60° C. for 30 min and at 38° C. overnight.

Sections were deparaffinized by incubation in xylene bath for 5 minutes twice, in acetone for 5 minutes twice and finally in distilled water for 5 minutes. Heat pretreatment of the sections was done in 10 mM citrate buffer, pH 6.0 in a microwave oven for 30 minutes at 250 W, followed by washing in distilled water. Endogenous peroxidase was blocked by incubation in a freshly prepared solution of 0.3% $H_2O_2$ in methanol for 20 minutes at room temperature followed by washing in distilled water for 5 minutes. Except for counterstaining with hematoxylin and mounting, the following steps were performed overnight using the Tecan-Immunostainer Genesis RSP 200 (Software: Gemini 3.40), which proceeds regarding manufacturer's EnVision+-staining procedure (DAKO Cytomation, ChemMate rabbit/mouse): Slides were rinsed twice in PBS/0.05% TWEEN pH 7.4 for 7 minutes and incubated with antibody eag-1 (provided by U3) for 4 hours (1:200 dilution in Antibody Diluent (DAKO)). The reaction was stopped with 100 µl PBS/0.05% TWEEN pH 7.4 per slide. After washing in 1400 µl PBS/0.05% TWEEN pH 7.4 for 7 minutes, the slides were incubated with secondary antibody/peroxidase-conjugate (30 minutes, 150 µl/slide, DAKO HRP/rabbit-mouse ChemMate). After washing as before the staining reaction was achieved with 120 µl/slide DAB solution (DAKO; 1:50 dilution in substrate buffer) for 10 minutes. The reaction was stopped with 100 µl PBS/0.05% TWEEN pH 7.4 for 20 min, followed by washing with 1400 µl PBS/0.05% TWEEN pH 7.4 for 7 minutes and then slides were washed every two hours with PBS/0.05% TWEEN pH 7.4, totally three times. Finally the slides were rinsed in water, counterstained with Harris' hematoxylin and covered with a glass slide. To exclude unspecific binding of the IgG2b molecule, control sections were incubated with IgG2b negative control (DAKO) instead of eag-1 antibody.

C. Staging of Cancer in a Patient

Based on the results set forth and discussed under items A. and B., through use of the present invention, it is possible to stage a cancer in a subject based on expression levels of the EAG1 antigen. For a given type of cancer, samples of blood or biopsies were taken from subjects diagnosed as being at various stages in the progression of the disease, and/or at various points in the therapeutic treatment of the cancer. The level of the EAG1 antigen present in the samples was determined using a method that specifically determines the amount of the antigen that is present. Such a method includes an ELISA or a IHC method, such as the method described under items A. and B. Using a population of samples that provides statistically significant results for each stage of progression or therapy, a range of levels of the EAG1 antigen expression that may be considered characteristic of each stage was designated. In order to stage the progression of the cancer in a subject under study, or to characterize the response of the subject to a course of therapy, a sample of blood or a biopsy was taken from the subject and the level of the EAG1 antigen present in the sample was determined. The level of antigen expression so obtained was used to identify in which range of concentrations the value falls. The range so identified correlates with a stage of progression or a stage of therapy identified in the various populations of diagnosed subjects, thereby providing a stage in the subject under study.

Example 11

Uses of EAG1 Antibodies and Antibody Conjugates of the Invention for Tumor Treatment A. Treatment of Humans with EAG1 Antibodies of the Invention For targeted tumor therapy of human patients with anti-EAG1 antibody of the invention, such human patients are injected over a certain amount of time with an effective amount of EAG1 antibody of the invention. At periodic times during the treatment, the human patients are monitored to determine whether their tumors progress, in particular, the tumor growth and metastasis.

A tumor patient treated with the EAG1 antibodies of the invention has a lower level of tumor growth and metastasis compared to the level of tumor growth and metastasis of tumors in tumor patients treated with control antibodies. Control antibodies that may be used include antibodies of the same isotype as the anti-EAG1 antibodies tested and further, may not have the ability to bind to Eag1 tumor antigen.

B. Treatment with EAG1 Antibody Conjugates of the Invention

For targeted tumor therapy with EAG1 antibody conjugates of the invention, human patients or animals exhibiting tumors are injected over a certain amount of time with an effective amount of EAG1 antibody conjugate of the invention. For example, the EAG1 antibody conjugate administered is maytansine-EAG1 antibody conjugate (or MMEA-EAG1 antibody conjuagate) or radioisotope-EAG1 antibody conjugate. At periodic times during the treatment, the human patients or animals are monitored to determine whether their tumors progress, in particular, tumor growth and metastasis.

A human patient or animal exhibiting tumors and undergoing treatment with either maytansine-EAG1 antibody or radioisotope-EAG1 antibody conjugates has a lower level of tumor growth and metastasis when compared to a control patient or animal exhibiting tumors and undergoing treatment with control antibody conjugates, such as control maytansine-antibody or control radioisotope-antibody. Control maytansine-antibodies that may be used include conjugates comprising maytansine linked to antibodies of the same isotype of the EAG1 antibodies of the invention, but more specifically, not having the ability to bind to EAG1 tumor antigen. Control radioisotope-antibodies that may be used include conjugates comprising radioisotope linked to antibodies of the same isotype of the EAG1 antibodies of the invention, but more specifically, not having the ability to bind to EAG1 tumor antigen.

Example 12

Production of Recombinant Humanized Anti-EAG1 Antibody HU-IMAB3

For production and purification of hu-ImAb3 a CHOK1 monoclonal cell line expressing humanized anti-EAG1 antibody hu-ImAb3 has been generated. Therefore, 300 000 CHO K1 cells/well were seeded in a 6-well culture dish in DMEM/F12 medium containing 10% FCS 24 h. For transfection, 1 µg of each vector KK56humpTracer (hu-ImAb3 light chain) and 1 µg LK56humpcDNA3(hu-ImAb3 heavy chain), in a total volume of 500 µl Opti-MEM (Gibco, Cat.No. 31985-047), were incubated with 10 µl Lipofectamine 2000 transfection reagent (Invitrogen, Cat.No. 11668-019) for 20 min at room temperature.

CHOK1 cells were washed twice with Opti-MEM and 1.5 ml Opti-MEM was added to each well. The transfection mix was carefully added to each well and incubated for 4 h at 37° C. in 5% $CO_2$. Next, the transfection medium was removed and 2 ml DMEM/F12 medium containing 10% FCS was added to the cells. After 24 h incubation at 37° C. in 5% $CO_2$ transfected cells were plated in three different dilution factors on 15 cm plates and selected with Zeozin (0.5 mg/ml) and G418 (1 mg/ml). Medium (containing antibiotics) was changed every second day. Single clones were picked by pipetting 20 µl of cells on a single 12-well plate.

Monoclonal cell lines were cultivated and further selected until cells could be plated on two 6-wells. In each case one well was used for further cultivation whereas the other one was used for testing for hu-ImAb3 expression.

Therefore, $2.5 \times 10^6$ cells were plated on a 10 cm dish. After 24 hours the medium was removed, 5 ml DMEM/F12 containing 5% low IgG was added and each monoclonal cell line was incubated for 48 h at 37° C. in 5% $CO_2$. 2 ml supernatant was removed, centrifuged and used for immunoprecipitation with 40 µl Protein A/G-Sepharose (1:1). Immunoprecipitates were washed and analysed on a 10% SDS-Page. Expression of hu-ImAb3 was detected using a secondary anti-human Peroxidase-conjugated antibody detection system (FIG. 11).

For production of hu-ImAb3, the monoclonal cell line CHOhu-ImAb3 clone 5 was cultivated using an INTEGRA CELLine 1000 system.

Therefore, $4 \times 10^7$ cells were incubated with 12 ml Cytodex microcarrier beads in DMEM/F12 supplemented with 10% low IgG FCS in a final volume of 15 ml. 25 ml DMEM/F12 were added to the nutrition-compartment of the CELLine 1000 to wet the membrane. CHOhu-ImAb3 cl.5 cells were pipetted to the cell-compartment and incubated for 90 min, with gentle shaking every ca. 10 min to allow the cells to adhere to the beads. 500 ml DMEM/F12 supplemented with 10% FCS was filled into the nutrient-compartment. 7 days later cells were removed and the medium in the nutrition-compartment was changed. After centrifugation, cells and beads were resuspended and re-transferred to the cell-compartment. The centrifuged supernatant containing hu-ImAb3 was transferred into a fresh tube and kept at −20° C. Cell supernatant was harvested every fourth day.

For purification of the hu-ImAb3 antibody cell supernatants were centrifuged and sterile filtrated. The antibody was purified using the Äkta Explorer System (rProteinA-Sepharose FF; binding buffer: 20 mM $NaPO_4$ pH8.8; elution buffer: 0.1M Glycine; 0.15M NaCl pH3.3)

Antibody was dialyzed (PBS), sterile filtrated, endotoxin tested and the concentration was determined by BCA-Test.

Example 13

Colony Formation Assay (Soft Agar Assay)

Soft agar assays were conducted in order to investigate the ability of the anti-EAG1 antibodies of the invention to inhibit anchorage independent cell growth. The soft agar colony formation assay is a standard in vitro assay to test for transformed cells, as only such transformed cells can grow in soft agar.

Figure 12A:
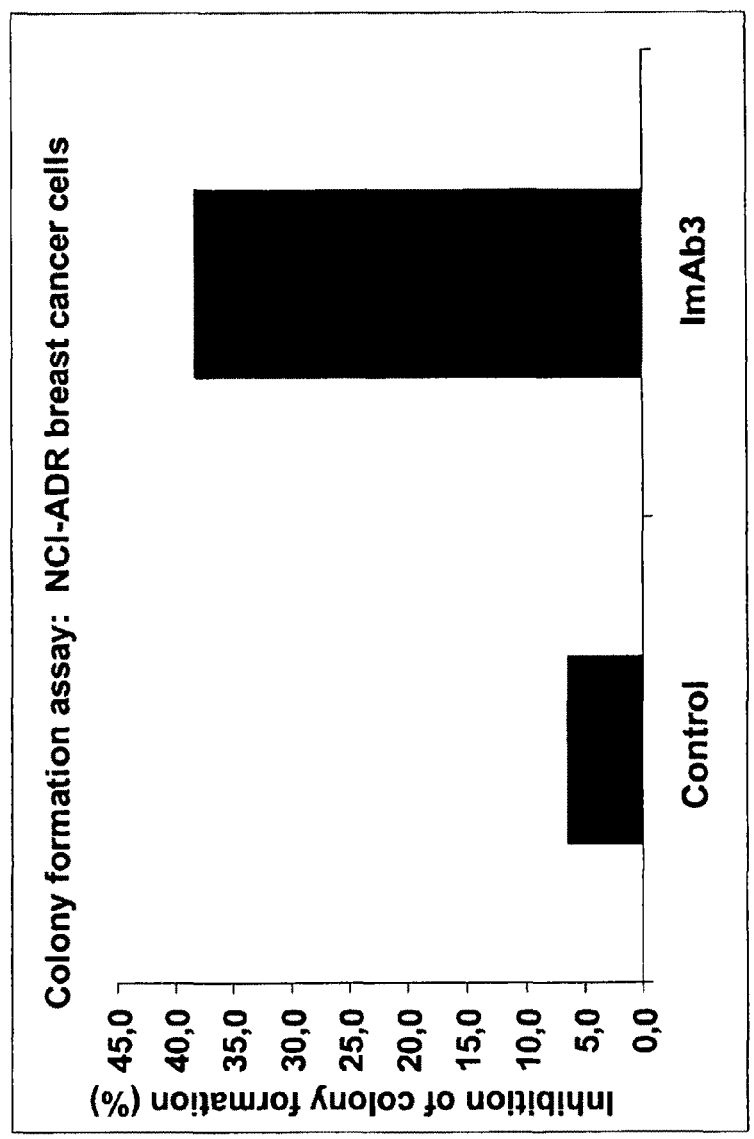
Figure 12B:
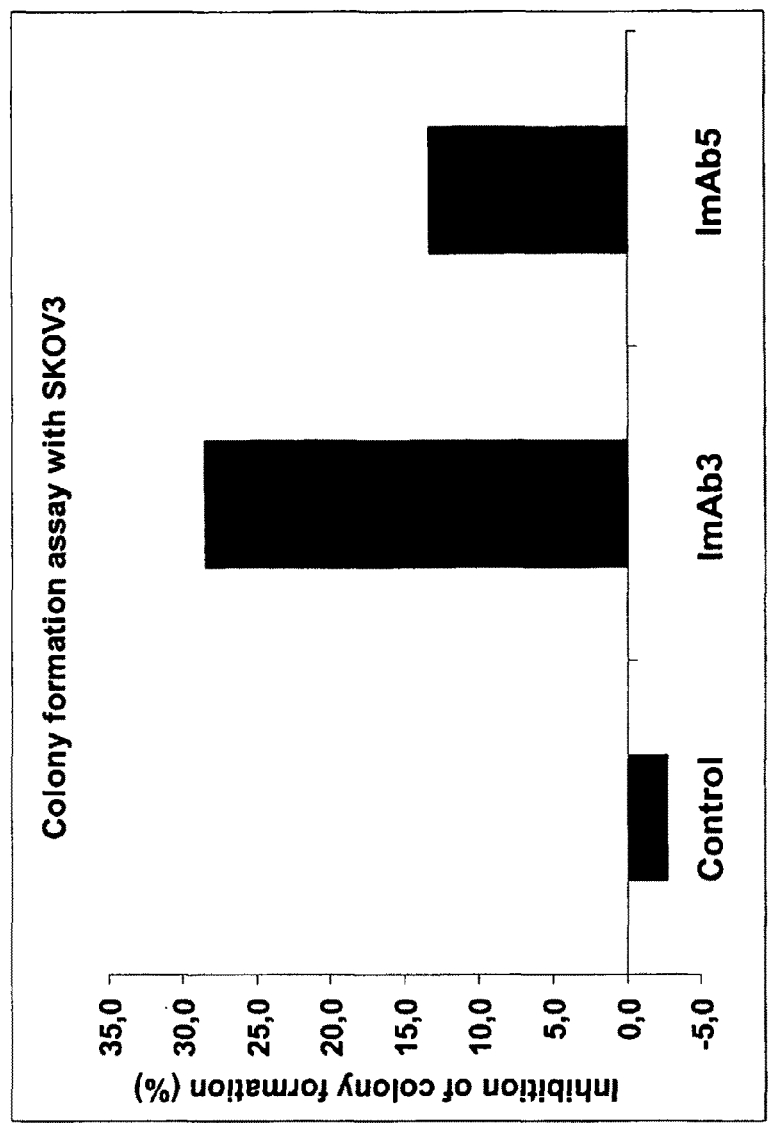
Figure 12C:
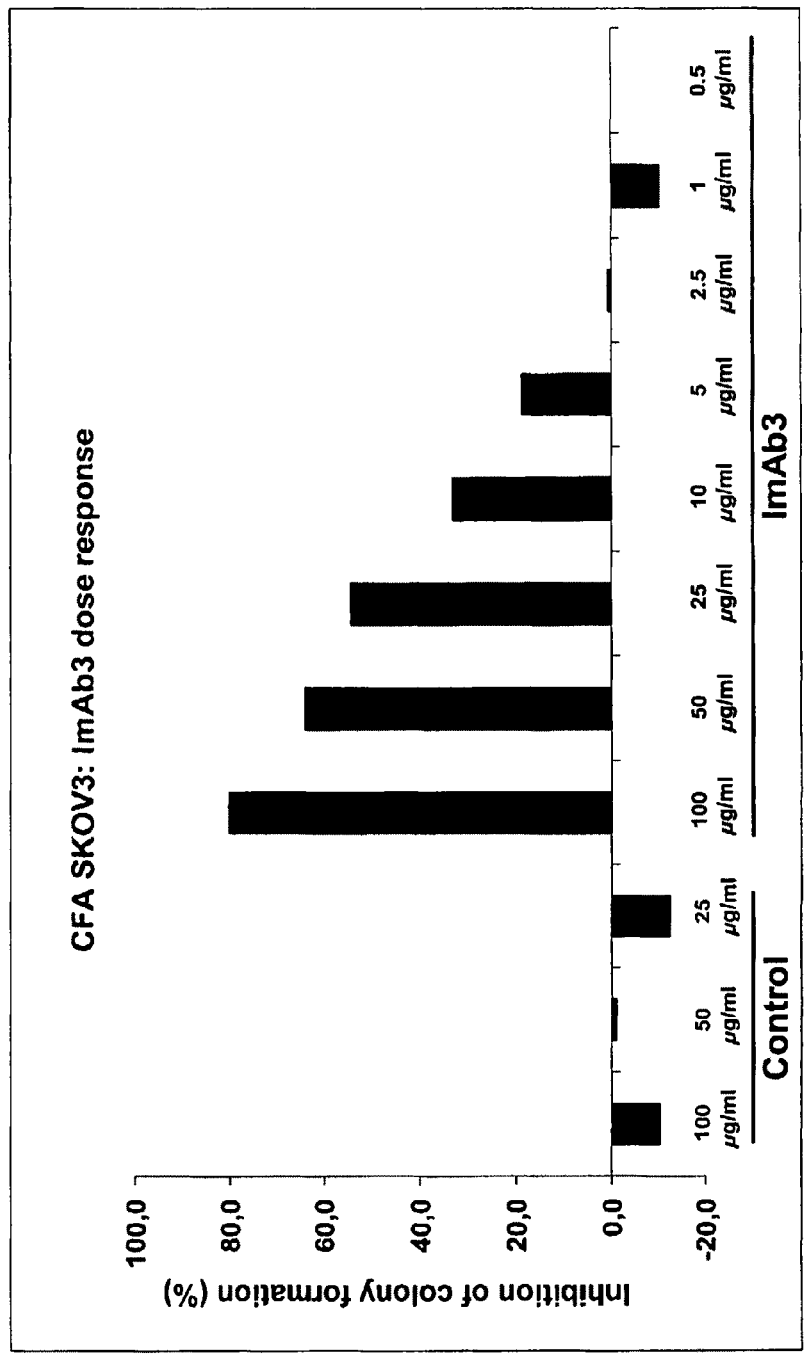
Figure 12E:
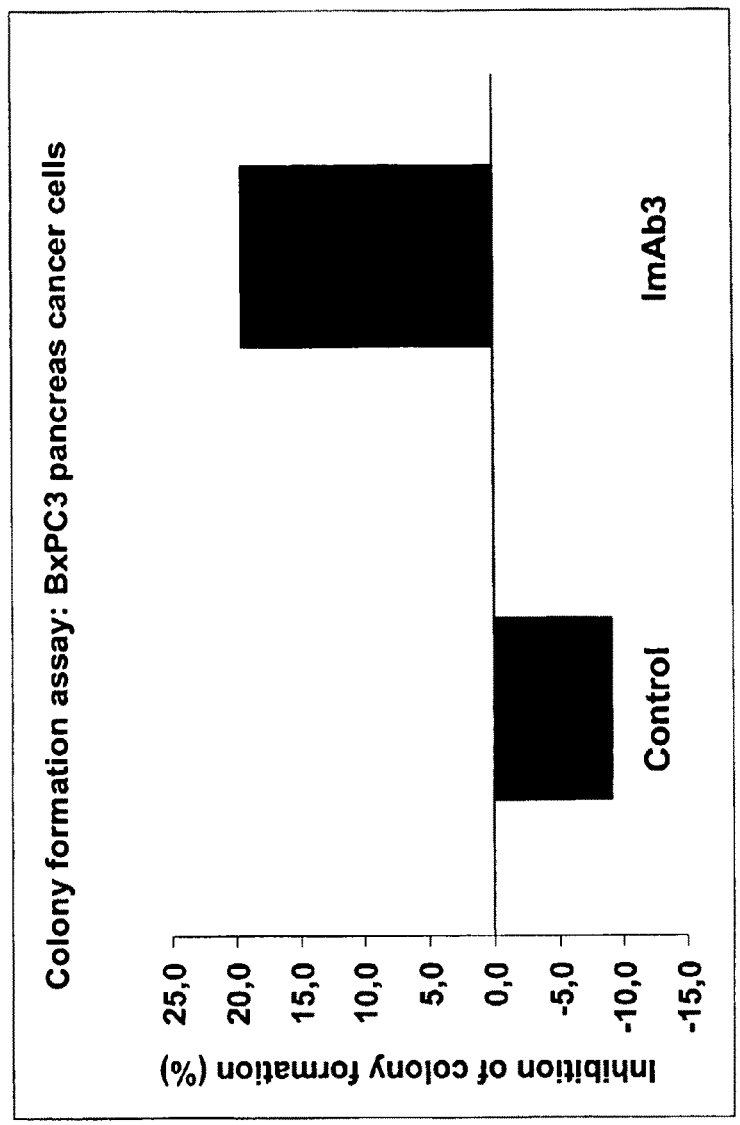
Figure 12F:
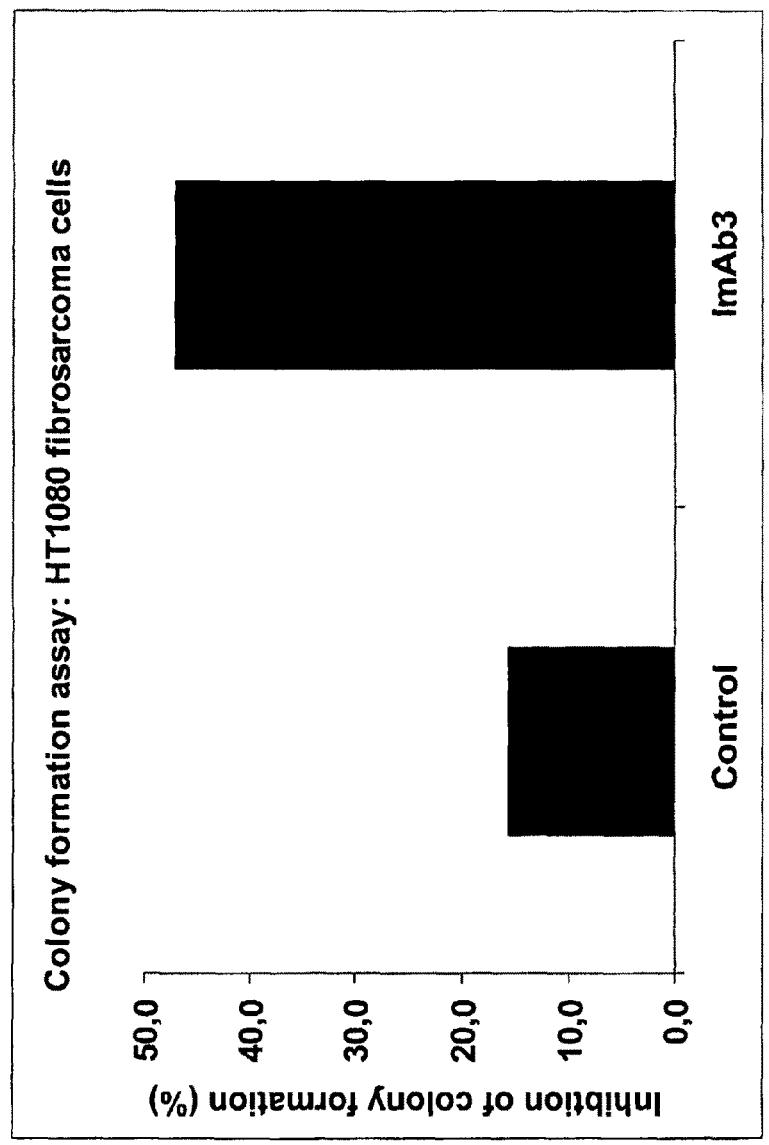
Figure 12G:
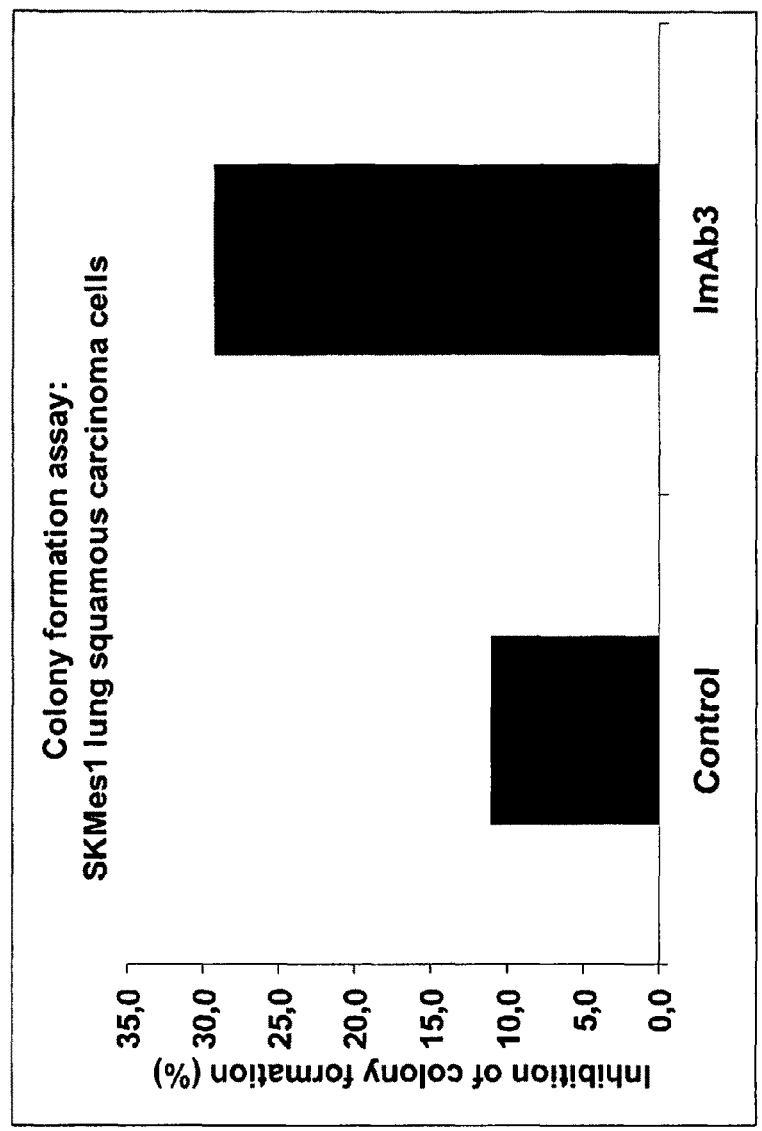

750 to 1000 cells (depending on the cell line) were preincubated with the indicated antibodies at 15 µg/ml in IMDM medium (Gibco) containing 0.1% to 0.5% FCS (depending on the cell line) for 75 min. Next the cells were resuspended in 0.25% to 0.3% Difco noble agar containing 0.1% to 0.5% FCS (depending on the cell line). The cell suspension was plated on a 0.5% to 0.6% agarose underlayer containing 20% FCS in triplicate in a 96-well plate. Colonies were allowed to form for 7 to 12 days and were then stained with 50 µl MTT (0.5 mg/ml in PBS) for 8 h to 12 h. FIGS. 12a-i show the results of these experiments performed with anti-EAG1 antibodies of the invention. These results demonstrate that mouse ImAb3 of the invention inhibit anchorage independent cell growth of NCl-ADR breast cancer cells (FIG. 12a), SKOV3 ovary carcinoma cells (FIGS. 12b,c), HT144 melanoma cells (FIG. 12d), BX-PC3 pancreas cancer cells (FIG. 12e), HT1080 fibrosacrcoma cells (FIG. 12f) and SKMes1 lung squamous carcinoma cells (FIG. 12g). In addition, FIG. 12b demonstrates that also anti-EAG1 antibody ImAb5 reduces colony formation of SKOV3 ovary carcinoma cells. The numbers and the size of colonies were analyzed using the Scanalyzer HTS camera system (LemnaTec, Wuerselen) including the software SAW Version 4.0.

Example 14

Inhibition of SKOV3 Cell Proliferation by Mouse Anti-EAG1 Antibody IMAB3 OF the Invention In vitro experiments were conducted in order to determine the ability of anti-EAG-antibodies of the invention to inhibit cancer cell proliferation. 1000 SKOV3 cells were seeded on 96-well plates in 100 µl/well medium (DMEM 4500 mg/ml glucose) supplemented with 10% FCS. After 24 h, cells were washed with PBS and incubated for 24 h in 60 µl/well medium containing 0.5% FCS. At next cells were treated in quadruplicates with 15 µg/ml anti-Eag1 monoclonal antibody ImAb3 or the corresponding control antibody (mouse IgG2b) diluted in 40 µl/well. Cells were incubated at 37° C. in 5% $CO_2$ for 3 days. In order to assess proliferation and cell viability, 20 µl CellTiter 96® $AQ_{ueous}$ One Solution reagent (Promega) containing the tetrazolium salt MTS and the electron coupling reagent phenazine methosulfate (PMS) was added to each well and incubated at 37° C. for various periods ranging from 10 min up to 3 hours. The quantity of the formazan product was measured by the amount of 590 nm absorbance using an ELISA plate reader. The results as indicated in FIG. 13 show that the antibody of the invention inhibits human cancer cell proliferation and/or viability.

Example 15

Anti-EAG Antibody IMAB3 Inhibits Human Breast Carcinoma Growth in Female SCID Mice In order to determine, if anti-EAG1 antibodies of the invention interfere with tumor growth of human breast cancer cells in SCID mice, $10^7$ MDA-MB-435s cells were implanted subcuanteously in female SCID mice. Tumors were grown on the back of the animal. Treatments began when tumors were measurable; approximately 7 days post implantation. Prior to first treatment, mice were randomized and statistical tests were performed to assure uniformity in starting tumor volumes (mean, median and standard deviation) across treatment groups. After randomization, ten out of twelve mice per group that were initially implanted with MDA-MB-435s cells, were used for the actual study. One group received the monoclonal murine anti-EAG1 antibody ImAb3 and the second group received the vehicle PBS as a control. Treatment started at the day of randomization with a loading dose for the anti-EAG1 antibody ImAb3 of 58 mg/kg followed by 20 mg/kg intraperitoneal injections once a week. The control group received the vehicle PBS with the same treatment schedule. Animals were treated for 96 days (13 weeks).

Tumor measurements and animal weights were taken twice weekly for duration of the study. Mean group tumor volumes were calculated by addition of the individual tumor volumes divided by the number of mice in the group. Data summarized in FIG. 14 demonstrate that administration of the anti-EAG1 antibody ImAb3 resulted in reduction of human breast carcinoma growth in immunocompromized mice.

Example 16

Inhibition of Anchorage Independent Cell Growth by Human Anti-EAG1 Antibody Imab3 in Combination with a Second Therapeutic Monoclonal Antibody or an Anti-Neoplastic Agent The monotherapy of hyperproliferative diseases with antibodies or other anti-neoplastic agents may often be hampered through problems such as, on the one hand, the development of resistance to drugs, and on the other hand, a change in the antigenicity of cells that would render them unreactive with the antibody. These problems might be evaded by using anti-EAG1 antibodies of the invention in combination with another therapeutic antibody, such as an antibody directed against a receptor tyrosine kinase, or other anti-neoplastic agents. Said combined treatment is also advantageous because it combines two anti-cancer agents, each operating via a different mechanism of action to yield a cytotoxic response to prevent or treat hyper-proliferative diseases.

Surprisingly it was found that combined treatment of anti-EAG1 antibody ImAb3 with the anti-EGFR antibody Erbitux (Cetuximab; Merck) results in a stronger reduction of the anchorage independent growth of human cancer cells than the use of the novel monoclonal antibody or EGFR antibody alone.

To test the efficacy of ImAb3 in combination with Erbitux on inhibition of anchorage independent cell growth of ovary carcinoma cells, 1000 SKOV3 cells were preincubated with 7.5 µg/ml ImAb3 or control antibody (mouse IgG2b) in IMDM medium containing 0.5% FCS for 75 min. After this preincubation 7.5 µg/ml Erbitux was added and cells were resuspended in 0.25% Difco noble agar (0.5% FCS). The cells were then plated on a 0.5% Difco noble agar underlayer containing 20% FCS in triplicate in a 96-well plate.

To test the efficacy of ImAb3 in combination with Erbitux on inhibition of anchorage independent cell growth of pancreas carcinoma cells, 1500 BxPC3 cells were preincubated with 15 µg/ml ImAb3 or control antibody in IMDM medium containing 0.5% FCS for 75 min. After this preincubation step 15 µg/ml Erbitux was added and cells were resuspendend in 0.25% Difco noble agar (0.5% FCS) and plated on a 0.5% agar underlayer containing 20% FCS in triplicate in a 96-well plate.

After 8 days incubation at 37° C., 5% $CO_2$ colonies were stained with 50 µl MTT (0.5 mg/ml in PBS) over night. The numbers and the size of colonies were analyzed using the Scanalyzer HTS camera system (LemnaTec) including the software SAW Version 4.0. FIGS. 15a and 15b demonstrate that combined treatment of anti-EAG1 antibody ImAb3 with the anti-EGFR antibody Erbitux efficiently inhibits the growth of ovary (SKOV3) and pancreas (BxPC3) tumor cells.

Furthermore the efficacy of ImAb3 in combination with the chemotherapeutic agents Taxol or Cisplatin on inhibition of anchorage independent cell growth was tested. Therefore 1000 SKOV3 cells were preincubated with ImAb3 or control antibody (mouse IgG2b) at 5.5 µg/ml (in case of the combination with Taxol) or 7.5 µg/ml (in case of the combination with Cisplatin) in IMDM medium containing 0.5% FCS for 75 min. After the preincubation of the cells with ImAb3 or control antibody the chemotherapeutic agents Taxol (3 nM) or Cisplatin (500 nM) were added and cells were resuspended in 0.25% Difco noble agar (0.5% FCS). Cells were plated on a 0.5% Difco noble agar underlayer containing 20% FCS in triplicate in a 96-well plate and incubated for 8 days.

In order to analyze the combined effect of ImAb3 and Cisplatin on anchorage independent cell growth of human melanoma cells, 1000 HT144 cells were preincubated with 30 µg/ml anti-EAG1 antibody ImAb3 or control antibody (mouse IgG2b) in IMDM medium containing 0.5% FCS for 75 min. Next 500 nM Cisplatin was added and cells were resuspended in 0.3% Difco noble agar (0.5% FCS) and plated on a 0.6% Difco noble agar underlayer containing 20% FCS in triplicate in a 96-well plate and incubated for 8 days.

Figure 15C:
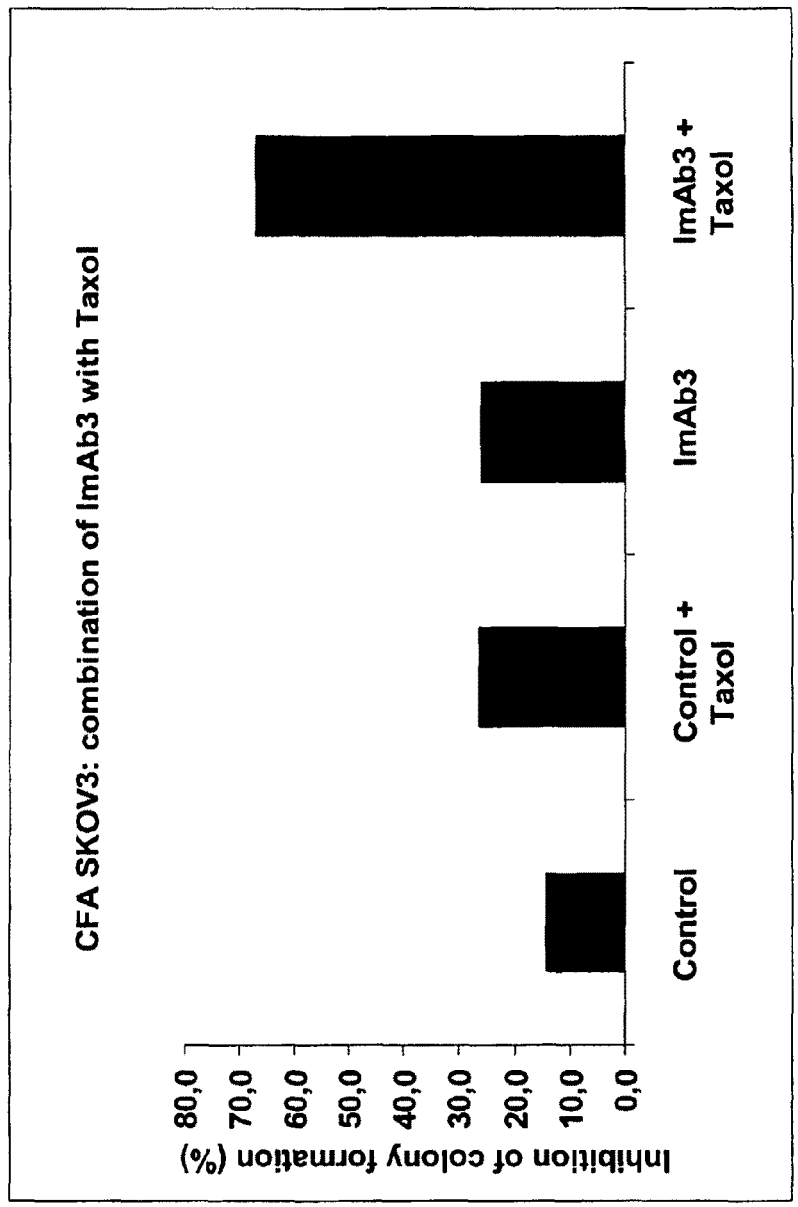
Figure 15D:
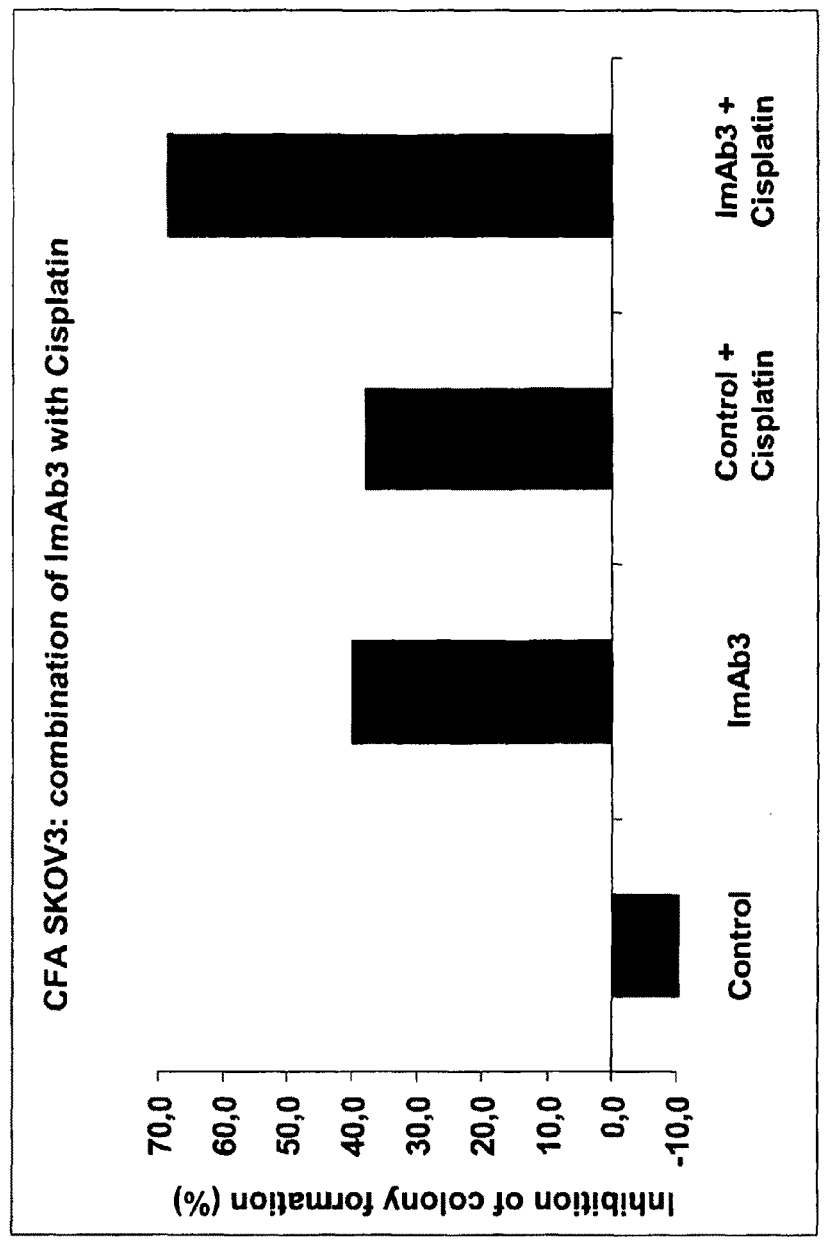

FIG. 15c demonstrates that combined treatment of SKOV3 ovary carcinoma cells with anti-EAG1 antibody ImAb3 and the anti-neoplastic agent Taxol results in a stronger reduction of the anchorage independent growth of human cancer cells than the use of the novel monoclonal antibody or Taxol alone. Furthermore it is shown in FIGS. 15d and that treatment of human ovary carcinoma as well as melanoma cells with a combination of the anti-EAG1 antibody ImAb3 and the chemotherapeutic agent Cisplatin results in a stronger reduction of the anchorage independent growth of human cancer cells than the use of the novel monoclonal antibody or Cisplatin alone. The numbers and the size of colonies were analyzed using the Scanalyzer HTS camera system (LemnaTec) including the software SAW Version 4.0.

Example 17

Inhibition of SKOV3 Cell Proliferation by Mouse Anti-EAG1 Antibody ImAb3 of the Invention in Combination With the Anti-Neoplastic Agent Taxol In order to determine the effect of a combined-treatment of anti-EAG1 antibodies of the invention with the potent anti-neoplastic agent Taxol on cell proliferation, in vitro cell proliferation assays were conducted using both anti-cancer agents in combination.

Therefore 750 SKOV3 cells were seeded on 96-well plates in 100 µl/well medium (DMEM 4500 mg/ml glucose) supplemented with 10% FCS overnight. Cells were washed with PBS and starved for 24 h in 60 µl/well medium containing 0.5% FCS. Cells were treated in quadruplicates with 30 µg/ml anti-Eag1 monoclonal antibody ImAb3, PBS or 1 nM Taxol diluted in 20 µl/well as indicated in FIG. 16 at 37° C. in 5% $CO_2$ for 1 h. After this pre-incubation step, 1 nM Taxol, 30 µg/ml ImAb3 or DMSO were added in 20 µl/well as indicated in FIG. 16 and cells were then incubated at 37° C. in 5% $CO_2$ for 3 days. In order to assess proliferation and cell viability 20 µl CellTiter 96® $AQ_{ueous}$ One Solution reagent (Promega) containing the tetrazolium salt MTS and the electron coupling reagent phenazine methosulfate (PMS) was added to each well and incubated at 37° C. for various periods ranging from 10 min up to 3 hours. The quantity of the formazan product was measured by the amount of 590 nm absorbance using an ELISA plate reader. The results as indicated in FIG. 16 show that combined treatment of anti-EAG1 antibody ImAb3 with the potent anti-neoplastic agent Taxol efficiently inhibits the growth of human ovary carcinoma cells. In addition it is demonstrated that the order of treatment (pre-incubation of cells with Taxol followed by ImAb3 or pre-incubation with ImAb3 followed by Taxol) has no influence on the inhibitory effect on cell proliferation of SKOV3 cells by combined treatment of ImAb3 with Taxol.

Example 18

Inhibition of Human Cancer Cell Proliferation by Human Anti-EAG1 Antibodies of the Invention Conjugated to the Immunotoxin Saporin In order to evaluate the specific suitability and efficacy of anti-Eag1 antibodies of the invention for conjugation as primary immunotoxin, in vitro cell proliferation assays were performed with anti-EAG1 antibodies of the invention conjugated to saporin, a ribosome-inactivating protein from the seeds of the plant *Saponaria officinalis*.

Conjugation of the anti-Eag1 antibody ImAb3 to saporin (ImAb3-SAP) via disulfide linkage and purification of the conjugated antibody ImAb3-SAP was performed by Advanced Targeting Systems (San Diego, Calif., USA).

To test the ability of the saporin-conjugated anti-EAG1 antibody ImAb3-SAP to interfere with cancer cell proliferation, 1000 cancer cells/well were seeded on 96-well plates in 100 µl culture medium (depending on the cell line) supplemented with 10% FCS. After 24 h, cells were washed with PBS and incubated for 24 h in 60 µl/well medium containing 10% FCS. Cells were treated in quadruplicates with 1 µg/ml saporin-conjugated anti-Eag1 monoclonal antibody ImAb3-SAP or control IgG-SAP diluted in 40 µl/well. Cells were then incubated at 37° C. in 5% $CO_2$ for 3 days. In order to assess proliferation and cell viability 20 µl/well CellTiter 96® $AQ_{ueous}$ One Solution reagent (Promega) containing the tetrazolium salt MTS and the electron coupling reagent phenazine methosulfate (PMS) was added to each well and incubated at 37° C. for various periods ranging from 10 min up to 3 hours. The quantity of the formazan product was measured by the amount of 590 nm absorbance using an ELISA plate reader.

The results demonstrate that saporin-conjugated ImAb3-SAP efficiently inhibits cell proliferation in the melanoma cell lines HT144, RPMI7951, C8161 and SkMel2 (FIG. 17a), in ovary carcinoma cell lines SKOV3 and IGROV1, the pancreas carcinoma cell line BxPC3 and the fibrosarcoma cell line HT1080 (FIG. 17b) and in the breast carcinoma cell lines T47D, NCI-ADR and the colon carcinoma cell line SW480 (FIG. 17c). Therefore, the anti-EAG1 antibodies of the invention are suitable for conjugation as primary immunotoxin and were shown to be a very efficient agent to inhibit growth of human cancer cells.

Example 19

Functional Inhibition of EAG1 Currents by Antibodies Of the Invention

To characterize effective affinity and specificity of the antibodies, block of Eag1 currents by ImAb3 in transfected HEK293 cells was tested in the whole cell configuration of the patch clamp technique. Currents were elicited by the depicted (FIG. 18a) pulse protocol (depolarization to +40 mV from a holding potential of −80 mV). Once a stable current level had been achieved, the antibody was applied to the bath chamber at a concentration of 300 nM, (approx 45 µg/ml). As a control, we used the related antibody ImAb4, which showed no effect on current amplitudes at the same concentration. The effect of ImAb3 was completely abolished by incubation of the antibody with excess peptide harbouring the sequence of the epitope for ImAb3. The antibody and the peptide were incubated (1:1 representing approximately 50 times molar excess of the peptide) at room temperature for 1 h and the mixture was used as described for the antibody alone. Use of a peptide with the epitope sequence for ImAb4 did not affect the action of ImAb3.

To test for the specificity of this inhibition, the effect of ImAb3 on HERG currents was also tested in transfected HEK293 cells. Currents were elicited by a depolarization to +40 mV from a holding potential of −80 mV. HERG shows typically very fast inactivation and a slow deactivation that allows measuring current amplitudes in the tail current upon repolarization of the membrane. Addition of ImAb3 (N=6) did not affect current amplitude over a certain extent of current rundown observed also in the absence of added antibody (FIG. 18 b).

Example 20

Localization of Implanted Tumor Cells Using Near-Infrared Labeled Antibodies of the Invention FIG. 19 shows a pseudo-color image showing near-infrared fluorescence intensity (A) and lifetime (B) on a mouse carrying and Eag1-expressing tumor after IV injection of specific anti-Eag1 antibody labeled with AlexaFluo 680. The positive lymph node (arrow) had not been clinically evident. Measurements of lifetime allow the determination of the specificity of the signal. Only the colored areas were scanned in each case.

MDA-MB-435S cells ($10^7$) were implanted subcutaneously into the flank of female SCID mice. Antibody ImAb4 (500 μg) was incubated with AlexaFluo 680 anti mouse secondary antibody at room temperature for 1 h. 100 μg of the resulting labeled antibody were injected into the tail vein of the mouse. 24 hours thereafter, the mouse was anesthetized and scanned using the eXplore Optix 2 system (General Electric Co). After a whole body, low-resolution scan, the areas with positive signals were scanned at high resolution (longer exposure time). The location of the positive signals was confirmed by necropsy. To avoid manipulation of the antibody, a chimeric protein between a single chain antibody and DsRed2 has been generated, as well as a single chain antibody carrying a polylysine sequence to allow high efficiency labeling with near-infrared dyes (e.g. Cy5.5).

REFERENCES

Ouadid-Ahidouch H, Le Bourhis X, Roudbaraki M, Toillon R A, Delcourt P, Prevarskaya N. Changes in the K+ current-density of MCF-7 cells during progression through the cell cycle: possible involvement of a h-ether-a-gogo K+ channel Receptors Channels. 2001; 7(5):345-56.

Meyer R, Schonherr R, Gavrilova-Ruch O, Wohlrab W, Heinemann S H. Identification of ether a go-go and calcium-activated potassium channels in human melanoma cells. J Membr Biol. 1999 Sep. 15; 171(2):107-15.

Bianchi L, Wible B, Arcangeli A, Taglialatela M, Morra F, Castaldo P, Crociani O, Rosati B, Faravelli L, Olivotto M, Wanke E. herg encodes a K+ current highly conserved in tumors of different histogenesis: a selective advantage for cancer cells? Cancer Res. 1998 Feb. 15; 58(4):815-22.

Kohler G, Milstein C. Continuous cultures of fused cells secreting antibody of predefined specificity. Nature. 1975 Aug. 7; 256(5517):495-7.

Schier R, Marks J D. Efficient in vitro affinity maturation of phage antibodies using BIAcore guided selections. Hum Antibodies Hybridomas. 1996; 7(3):97-105.

Malmborg A C, Borrebaeck C A. BIAcore as a tool in antibody engineering. J Immunol Methods. 1995 Jun. 14; 183 (1):7-13.

Le Mouellic H, Lallemand Y, Brulet P. Targeted replacement of the homeobox gene Hox-3.1 by the *Escherichia coli* lacZ in mouse chimeric embryos. Proc Natl Acad Sci U S A. 1990 June; 87(12):4712-6.

Mandler R, Wu C, Sausville E A, Roettinger A J, Newman D J, Ho D K, King C R, Yang D, Lippman M E, Landolfi N F, Dadachova E, Brechbiel M W, Waldmann T A. Immunoconjugates of geldanamycin and anti-HER2 monoclonal antibodies: antiproliferative activity on human breast carcinoma cell lines. J Natl Cancer Inst. 2000 Oct. 4; 92(19): 1573-81.

Sambrook, Molecular Cloning A Laboratory Manual, Cold Spring Harbor Laboratory (2001, Third Edition)

Doronina A O, Toki B E, Torgov M Y, Mendelsohn B A, Cerveny C G, Chace D F, DeBlanc R L, Gearing R P, Bovee T D, Siegall C B, Francisco J A, Wahl, A F, Meyer D L, Senter P D. Development of potent monoclonal auristatin conjugates for cancer therapy. Nat Biotechnol 2003 Jul. 21 (7):778-784.

The invention claimed is:

1. An isolated antibody, antibody fragment or derivative thereof comprising light chain variable ($V_L$) region complimentarity determining regions 1, 2, and 3 (CDR1, CDR2, and CDR3), and heavy chain variable ($V_H$) region CDR1, CDR2, and CDR3, the CDRs being present in each of said variable chains in CDR1, CDR2, CDR3 order and having the amino acid sequences of SEQ ID NOs: 166, 167, 168, 169, 170, and 171, respectively, wherein the antibody, antibody fragment or derivative thereof specifically binds to at least one epitope of the extracellular or intracellular domain of the mammalian ether-a-go-go 1 (EAG1) ion channel and does not bind to the mammalian EAG2 channel.

2. The antibody according to claim 1, wherein said antibody is a monoclonal antibody.

3. The antibody fragment or derivative thereof according to claim 1, wherein said antibody fragment thereof is a Fab-fragment, a F(ab')$_2$-fragment, or a Fv-fragment, and wherein said antibody derivative thereof is a single-chain antibody, a chimeric antibody, a CDR-grafted antibody, a bivalent antibody-construct, a humanized antibody, a human antibody, a synthetic antibody, a multispecific antibody, a diabody, or a chemically-modified Fab-fragment, F(ab')$_2$-fragment, Fv-fragment, single-chain antibody, chimeric antibody, CDR-grafted antibody, bivalent antibody-construct, humanized antibody, human antibody, synthetic antibody, multispecific antibody, or diabody.

4. The antibody or antibody derivative thereof according to claim 1, wherein said antibody or antibody derivative thereof comprises a light chain selected from the group consisting of SEQ ID NOs: 6, 10, 18, 26 and 30, and a heavy chain selected from the group consisting of SEQ ID NOs: 8, 12, 20, 28 and 32.

5. The antibody, antibody fragment or derivative thereof according to claim 1, wherein said antibody, fragment or derivative thereof is coupled to a labeling group.

6. A pharmaceutical composition comprising the antibody, antibody fragment or derivative thereof as defined in any one of claims 1, 2, 3, 4, and 5.

7. The pharmaceutical composition of claim 6, further comprising at least one anti-neoplastic agent.

8. A diagnostic composition comprising the antibody, antibody fragment or derivative thereof as defined in any one of claims 1, 2, 3, 4, and 5, and optionally, a pharmaceutically acceptable carrier.

9. A kit comprising the antibody, antibody fragment or derivative thereof of any one of claims 1, 2, 3, 4, and 5.

10. A method of assessing for the presence of EAG1 expressing cells comprising contacting a cell or tissue suspected of carrying EAG1 on its surface with the antibody, antibody fragment, or derivative thereof of any of claims 1, 2, 3, 4 or 5.

11. A method of blocking EAG1 function comprising contacting cells or a tissue suspected of carrying EAG1 on their/its surface with the antibody, antibody fragment or derivative thereof of any one of claims 1, 2, 3, 4 and 5.

12. The method of claim 10, wherein said contacting is performed in vitro.

13. The method of claim 10, wherein said contacting is performed in vivo.

14. The method of claim 11, wherein said contacting is performed in vitro.

15. The method of claim 11, wherein said contacting is performed in vivo.

* * * * *

UNITED STATES PATENT AND TRADEMARK OFFICE
CERTIFICATE OF CORRECTION

PATENT NO. : 7,910,100 B2
APPLICATION NO. : 11/664345
DATED : March 22, 2011
INVENTOR(S) : Walter Stühmer et al.

Page 1 of 1

It is certified that error appears in the above-identified patent and that said Letters Patent is hereby corrected as shown below:

In title page, item (73), please delete "Max-Planck-Gesellschaft zur Förderung der Wissen, Munich, (DE)" and insert -- Max-Planck-Gesellschaft zur Förderung der Wissenschaften e.V., Munich, (DE); U3 Pharma AG, Martinsfied (DE) -- therefore.

Signed and Sealed this
Ninth Day of August, 2011

David J. Kappos
*Director of the United States Patent and Trademark Office*